(12) United States Patent
Brustad et al.

(10) Patent No.: US 12,357,374 B2
(45) Date of Patent: Jul. 15, 2025

(54) ELECTROSURGICAL INSTRUMENTS AND CONNECTIONS THERETO

(71) Applicant: Applied Medical Resources Corporation, Rancho Santa Margarita, CA (US)

(72) Inventors: John Brustad, Rancho Santa Margarita, CA (US); Zoran Falkenstein, Rancho Santa Margarita, CA (US); Benjamin Linville-Engler, Irvine, CA (US); Matthew Wixey, San Jose, CA (US); Gary Johnson, Rancho Santa Margarita, CA (US); Patrick Elliott, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 31 days.

(21) Appl. No.: 18/544,022

(22) Filed: Dec. 18, 2023

(65) Prior Publication Data
US 2024/0122640 A1  Apr. 18, 2024

Related U.S. Application Data

(63) Continuation of application No. 17/135,520, filed on Dec. 28, 2020, now Pat. No. 11,864,823, which is a
(Continued)

(51) Int. Cl.
*A61B 18/00* (2006.01)
*A61B 18/12* (2006.01)
(Continued)

(52) U.S. Cl.
CPC .. *A61B 18/1445* (2013.01); *A61B 2017/2903* (2013.01); *A61B 2017/2932* (2013.01);
(Continued)

(58) Field of Classification Search
None
See application file for complete search history.

(56) References Cited

U.S. PATENT DOCUMENTS

| 371,664 A | 10/1887 | Brannan et al. |
| 702,472 A | 6/1902 | Pignolet |
(Continued)

FOREIGN PATENT DOCUMENTS

| DE | 4024636 A1 | 2/1992 |
| DE | 4024636 C2 | 12/1992 |
(Continued)

OTHER PUBLICATIONS

European Patent Office, Extended European Search Report for European Application No. EP 22212171.7, dated Mar. 21, 2023, 7 pgs.
(Continued)

*Primary Examiner* — Linda C Dvorak
*Assistant Examiner* — Nicholas S Borsch
(74) *Attorney, Agent, or Firm* — Patrick Ikehara

(57) ABSTRACT

An electrosurgical instrument includes jaws having an electrode configuration utilized to electrically modify tissue in contact with one or more electrodes. The instrument is removably connectable to an electrosurgical unit via an electrosurgical connector extending from the instrument and a receptacle on the electrosurgical unit. The electrosurgical instrument is rotatable without disrupting electrical connection to the electrodes of the jaws. One or more of the electrodes is retractable. The electrosurgical unit and instrument optimally seals and/or cuts tissue based on identifying the tissue and monitoring the modification of the tissue by the application of radio frequency energy.

18 Claims, 60 Drawing Sheets

Related U.S. Application Data continuation of application No. 15/936,914, filed on Mar. 27, 2018, now Pat. No. 10,874,452, which is a continuation of application No. 15/136,652, filed on Apr. 22, 2016, now Pat. No. 9,962,222, which is a continuation of application No. 13/366,487, filed on Feb. 6, 2012, now Pat. No. 9,320,563, which is a continuation of application No. PCT/US2011/054661, filed on Oct. 3, 2011.

(60) Provisional application No. 61/389,012, filed on Oct. 1, 2010.

(51) Int. Cl.
*A61B 18/14* (2006.01)
*A61B 17/29* (2006.01)

(52) U.S. Cl.
CPC .............. *A61B 2018/00178* (2013.01); *A61B 2018/00196* (2013.01); *A61B 2018/00601* (2013.01); *A61B 2018/00607* (2013.01); *A61B 2018/0063* (2013.01); *A61B 2018/00642* (2013.01); *A61B 2018/00708* (2013.01); *A61B 2018/00827* (2013.01); *A61B 2018/00869* (2013.01); *A61B 2018/00892* (2013.01); *A61B 2018/1412* (2013.01); *A61B 2018/1432* (2013.01)

(56) References Cited

U.S. PATENT DOCUMENTS

| | | | |
|---|---|---|---|
| 728,883 | A | 5/1903 | Downes |
| 1,586,645 | A | 6/1926 | Bierman |
| 1,935,289 | A | 4/1933 | Evans |
| 2,002,594 | A | 5/1935 | Wappler et al. |
| 2,031,682 | A | 2/1936 | Wappler et al. |
| 2,113,246 | A | 4/1938 | Wappler |
| 2,176,479 | A | 10/1939 | Willis |
| 2,306,156 | A | 4/1941 | Grubel |
| 2,632,661 | A | 3/1953 | Cristofv |
| 2,827,056 | A | 3/1958 | Degelman |
| 3,085,566 | A | 4/1963 | Tolles |
| 3,459,187 | A | 8/1969 | Pallotta |
| 3,494,363 | A | 2/1970 | Jackson |
| 3,588,710 | A | 6/1971 | Masters |
| 3,651,811 | A | 3/1972 | Hildebrandt et al. |
| 3,685,518 | A | 8/1972 | Beuerle et al. |
| 3,780,416 | A | 12/1973 | Rider |
| 3,826,263 | A | 7/1974 | Cage |
| 3,911,766 | A | 10/1975 | Fridolph |
| 3,920,021 | A | 11/1975 | Hiltebrandt |
| 3,938,527 | A | 2/1976 | Rioux |
| 3,963,030 | A | 6/1976 | Newton |
| 3,970,088 | A | 7/1976 | Morrison |
| 3,980,085 | A | 9/1976 | Ikuno |
| 3,987,795 | A | 10/1976 | Morrison |
| 4,030,501 | A | 6/1977 | Archibald |
| 4,041,952 | A | 8/1977 | Morrison, Jr. et al. |
| 4,043,342 | A | 8/1977 | Morrison |
| 4,060,088 | A | 11/1977 | Morrison, Jr. et al. |
| 4,074,718 | A | 2/1978 | Morrison, Jr. |
| 4,089,336 | A | 6/1978 | Cage |
| 4,092,986 | A | 6/1978 | Schneiderman |
| 4,094,320 | A | 6/1978 | Newton et al. |
| 4,114,623 | A | 9/1978 | Meinke |
| 4,126,137 | A | 11/1978 | Archibald |
| 4,154,240 | A | 5/1979 | Ikuno |
| 4,171,700 | A | 10/1979 | Farin |
| 4,181,131 | A | 1/1980 | Ogui |
| 4,231,372 | A | 1/1980 | Newton |
| 4,188,927 | A | 2/1980 | Harris |
| 4,196,734 | A | 4/1980 | Harris |
| 4,198,957 | A | 4/1980 | Cage et al. |
| 4,198,960 | A | 4/1980 | Utsugi |
| 4,200,104 | A | 4/1980 | Harris |
| 4,237,887 | A | 12/1980 | Gonser |
| 4,244,371 | A | 1/1981 | Farin |
| 4,325,374 | A | 4/1982 | Komya |
| 4,331,149 | A | 5/1982 | Gonser |
| 4,338,940 | A | 7/1982 | Ikuno |
| 4,352,156 | A | 9/1982 | Gyugyi |
| 4,370,980 | A | 2/1983 | Lottick |
| 4,416,276 | A | 11/1983 | Newton |
| 4,416,277 | A | 11/1983 | Newton et al. |
| 4,427,014 | A | 1/1984 | Bel |
| 4,429,694 | A | 2/1984 | McGreevy |
| 4,463,759 | A | 8/1984 | Garito et al. |
| 4,487,489 | A | 12/1984 | Takamatsu |
| 4,514,619 | A | 4/1985 | Kugelman |
| 4,522,206 | A | 6/1985 | Whipple et al. |
| 4,552,143 | A | 11/1985 | Lottick |
| 4,569,131 | A | 2/1986 | Faulk et al. |
| 4,569,345 | A | 2/1986 | Manes et al. |
| 4,590,934 | A | 5/1986 | Malis et al. |
| 4,599,553 | A | 7/1986 | Brennen et al. |
| 4,630,218 | A | 12/1986 | Hurley |
| 4,632,109 | A | 12/1986 | Paterson |
| 4,644,950 | A | 2/1987 | Valli |
| 4,651,280 | A | 3/1987 | Chang et al. |
| 4,655,216 | A | 4/1987 | Tischer |
| 4,657,018 | A | 4/1987 | Hakky |
| 4,658,815 | A | 4/1987 | Farin et al. |
| 4,658,819 | A | 4/1987 | Harris et al. |
| 4,658,820 | A | 4/1987 | Klicek |
| 4,674,498 | A | 6/1987 | Stasz |
| 4,685,459 | A | 8/1987 | Koch et al. |
| 4,699,146 | A | 10/1987 | Sieverding |
| 4,712,545 | A | 12/1987 | Honkanen |
| 4,716,897 | A | 1/1988 | Noguchi et al. |
| 4,727,874 | A | 3/1988 | Bowers |
| 4,739,759 | A | 4/1988 | Rexroth et al. |
| 4,741,334 | A | 5/1988 | Irnich |
| 4,752,864 | A | 6/1988 | Clappier |
| 4,754,757 | A | 7/1988 | Feucht |
| 4,788,977 | A | 12/1988 | Farin et al. |
| 4,802,476 | A | 2/1989 | Noerenberg et al. |
| 4,818,954 | A | 4/1989 | Flachenecker |
| 4,827,927 | A | 5/1989 | Newton |
| 4,848,335 | A | 7/1989 | Manes |
| 4,850,353 | A | 7/1989 | Stasz et al. |
| 4,860,745 | A | 8/1989 | Farin et al. |
| 4,862,889 | A | 9/1989 | Feucht |
| 4,862,890 | A | 9/1989 | Stasz et al. |
| 4,872,456 | A | 10/1989 | Hasson |
| 4,887,612 | A | 12/1989 | Esser et al. |
| 4,889,722 | A | 12/1989 | Sheffield et al. |
| 4,903,696 | A | 2/1990 | Stasz et al. |
| 4,905,691 | A | 3/1990 | Rydell |
| 4,922,903 | A | 5/1990 | Welch et al. |
| 4,936,281 | A | 6/1990 | Stasz |
| 4,937,254 | A | 6/1990 | Sheffield et al. |
| 4,938,761 | A | 7/1990 | Ensslin |
| 4,942,313 | A | 7/1990 | Kinzel |
| 4,958,539 | A | 9/1990 | Stasz et al. |
| 4,969,067 | A | 11/1990 | Farin |
| 4,969,885 | A | 11/1990 | Farin |
| 4,976,711 | A | 12/1990 | Parins et al. |
| 5,007,908 | A | 4/1991 | Rydell |
| 5,013,312 | A | 5/1991 | Parins et al. |
| 5,015,227 | A | 5/1991 | Broadwin et al. |
| 5,016,521 | A | 5/1991 | Haka |
| 5,026,370 | A | 6/1991 | Lottick |
| 5,026,371 | A | 6/1991 | Rydell et al. |
| 5,036,696 | A | 7/1991 | Rydell |
| 5,038,109 | A | 8/1991 | Goble et al. |
| 5,047,026 | A | 9/1991 | Rydell |
| 5,047,027 | A | 9/1991 | Rydell |
| 5,052,402 | A | 10/1991 | Bencini et al. |
| 5,057,107 | A | 10/1991 | Parins et al. |
| 5,061,269 | A | 10/1991 | Muller |
| 5,062,031 | A | 10/1991 | Flachenecker et al. |
| 5,071,419 | A | 12/1991 | Rydell et al. |

(56) References Cited

U.S. PATENT DOCUMENTS

| | | |
|---|---|---|
| 5,078,717 A | 1/1992 | Parins et al. |
| 5,083,565 A | 1/1992 | Parins |
| 5,085,659 A | 2/1992 | Rydell |
| 5,087,257 A | 2/1992 | Farin et al. |
| 5,098,431 A | 3/1992 | Rydell |
| 5,116,332 A | 5/1992 | Lottick |
| 5,125,928 A | 5/1992 | Parins et al. |
| 5,122,137 A | 6/1992 | Lennox |
| 5,127,412 A | 7/1992 | Cosmetto et al. |
| 5,151,102 A | 9/1992 | Kamiyama et al. |
| 5,158,561 A | 10/1992 | Rydell et al. |
| 5,160,343 A | 11/1992 | Brancel et al. |
| 5,167,658 A | 12/1992 | Ensslin |
| 5,171,255 A | 12/1992 | Rydell |
| 5,171,311 A | 12/1992 | Rydell |
| 5,190,517 A | 3/1993 | Klicek et al. |
| 5,190,541 A | 3/1993 | Abele et al. |
| 5,192,280 A | 3/1993 | Parins |
| 5,197,963 A | 3/1993 | Parins |
| 5,197,964 A | 3/1993 | Parins |
| 5,201,732 A | 4/1993 | Parins et al. |
| 5,217,457 A | 6/1993 | Delahuerga et al. |
| 5,217,458 A | 6/1993 | Parins |
| 5,234,427 A | 8/1993 | Ohtorno et al. |
| 5,244,462 A | 9/1993 | Delahuerga et al. |
| 5,246,440 A | 9/1993 | Van Noord |
| 5,250,047 A | 10/1993 | Rydell |
| 5,250,056 A | 10/1993 | Hasson |
| 5,254,126 A | 10/1993 | Filipi et al. |
| 5,256,149 A | 10/1993 | Banik et al. |
| 5,258,006 A | 11/1993 | Rydell et al. |
| 5,267,997 A | 12/1993 | Farin et al. |
| 5,269,780 A | 12/1993 | Roos |
| 5,273,524 A | 12/1993 | Fox et al. |
| 5,281,216 A | 1/1994 | Klicek |
| 5,282,799 A | 2/1994 | Rydell |
| 5,286,255 A | 2/1994 | Weber |
| 5,290,286 A | 3/1994 | Parins |
| 5,300,070 A | 4/1994 | Gentella et al. |
| 5,304,190 A | 4/1994 | Reckelhoff et al. |
| 5,307,976 A * | 5/1994 | Olson ............. A61B 17/07207 227/175.3 |
| 5,312,329 A | 5/1994 | Beaty et al. |
| 5,314,424 A | 5/1994 | Nicholas |
| 5,318,563 A | 6/1994 | Malis et al. |
| 5,322,055 A | 6/1994 | Davison et al. |
| 5,324,289 A | 6/1994 | Eggers |
| 5,330,471 A | 7/1994 | Eggers |
| 5,334,183 A | 8/1994 | Wuchtnich |
| 5,338,317 A | 8/1994 | Hasson et al. |
| 5,341,815 A | 8/1994 | Cofone et al. |
| 5,342,359 A | 8/1994 | Rydell |
| 5,342,381 A | 8/1994 | Tidemand |
| 5,352,222 A | 10/1994 | Rydell |
| 5,352,223 A | 10/1994 | McBrayer et al. |
| 5,354,313 A | 10/1994 | Boebel |
| 5,356,408 A | 10/1994 | Rydell |
| 5,370,645 A | 12/1994 | Klicek et al. |
| 5,372,124 A | 12/1994 | Takayama et al. |
| 5,372,596 A | 12/1994 | Klicek et al. |
| 5,374,277 A | 12/1994 | Hassler |
| 5,382,247 A | 1/1995 | Cimino et al. |
| 5,383,880 A | 1/1995 | Hoven |
| 5,383,922 A | 1/1995 | Zipes et al. |
| 5,387,196 A | 2/1995 | Green et al. |
| 5,387,197 A | 2/1995 | Smith et al. |
| 5,389,104 A | 2/1995 | Hahnen et al. |
| 5,389,849 A | 2/1995 | Asano et al. |
| 5,391,166 A | 2/1995 | Eggers |
| 5,392,917 A | 2/1995 | Alpern et al. |
| 5,400,267 A | 3/1995 | Denen |
| 5,403,312 A | 4/1995 | Yates et al. |
| 5,403,342 A | 4/1995 | Tovey et al. |
| 5,405,344 A | 4/1995 | Willaimson et al. |
| 5,409,498 A | 4/1995 | Braddock et al. |
| 5,417,687 A | 5/1995 | Nardella et al. |
| 5,422,567 A | 6/1995 | Matsunaga |
| 5,423,808 A | 6/1995 | Edwards et al. |
| 5,423,810 A | 6/1995 | Gobie et al. |
| 5,431,638 A | 7/1995 | Hennig et al. |
| 5,431,649 A | 7/1995 | Mulier et al. |
| 5,431,674 A | 7/1995 | Basile et al. |
| 5,432,459 A | 7/1995 | Thompson et al. |
| 5,436,566 A | 7/1995 | Thompson et al. |
| 5,437,664 A | 8/1995 | Cohen et al. |
| 5,438,302 A | 8/1995 | Goble |
| 5,443,463 A | 8/1995 | Stern et al. |
| 5,445,142 A | 8/1995 | Hassler, Jr. |
| 5,445,638 A | 8/1995 | Rydell et al. |
| 5,447,513 A | 9/1995 | Davison et al. |
| 5,449,355 A | 9/1995 | Rhum et al. |
| 5,456,684 A | 10/1995 | Schmidt et al. |
| 5,458,598 A | 10/1995 | Feinberg et al. |
| 5,460,182 A | 10/1995 | Goodman et al. |
| 5,462,546 A | 10/1995 | Rydell |
| 5,464,144 A | 11/1995 | Guy et al. |
| 5,472,439 A | 12/1995 | Hurd |
| 5,472,443 A | 12/1995 | Cordis et al. |
| 5,472,451 A | 12/1995 | Freitas et al. |
| 5,474,057 A | 12/1995 | Makower et al. |
| 5,476,479 A | 12/1995 | Green et al. |
| 5,478,351 A | 12/1995 | Meade et al. |
| 5,486,185 A | 1/1996 | Freitas et al. |
| 5,496,312 A | 3/1996 | Klick |
| 5,496,317 A | 3/1996 | Goble et al. |
| 5,499,992 A | 3/1996 | Meade et al. |
| 5,499,998 A | 3/1996 | Meade et al. |
| 5,503,320 A | 4/1996 | Webster et al. |
| 5,507,773 A | 4/1996 | Hutema et al. |
| 5,509,916 A | 4/1996 | Taylor et al. |
| 5,514,129 A | 5/1996 | Smith |
| 5,514,134 A | 5/1996 | Rydell et al. |
| 5,518,164 A | 5/1996 | Hooven |
| 5,527,313 A | 6/1996 | Scott et al. |
| 5,527,330 A | 6/1996 | Tovey |
| 5,531,744 A | 7/1996 | Nardella et al. |
| 5,540,681 A | 7/1996 | Strul et al. |
| 5,540,684 A | 7/1996 | Hassler et al. |
| 5,540,685 A | 7/1996 | Parins et al. |
| 5,541,376 A | 7/1996 | Ladtkow et al. |
| 5,551,945 A | 9/1996 | Yabe et al. |
| 5,558,429 A | 9/1996 | Cain |
| 5,558,671 A | 9/1996 | Yates |
| 5,562,699 A | 10/1996 | Heimberger et al. |
| 5,562,700 A | 10/1996 | Huitema et al. |
| 5,571,100 A | 11/1996 | Goble et al. |
| 5,571,121 A | 11/1996 | Heifetz |
| 5,573,533 A | 11/1996 | Struf |
| 5,573,534 A | 11/1996 | Stone |
| 5,573,535 A | 11/1996 | Viklund |
| 5,575,805 A | 11/1996 | Li |
| 5,576,789 A | 11/1996 | Bell et al. |
| 5,584,830 A | 12/1996 | Ladd et al. |
| 5,599,344 A | 2/1997 | Paterson |
| 5,599,350 A | 2/1997 | Schulze et al. |
| 5,603,711 A | 2/1997 | Parins et al. |
| D378,611 S | 3/1997 | Croley |
| 5,607,391 A | 3/1997 | Klinger et al. |
| 5,609,151 A | 3/1997 | Mulier et al. |
| 5,609,560 A | 3/1997 | Ichikawa et al. |
| 5,609,573 A | 3/1997 | Sandock |
| 5,611,709 A | 3/1997 | McAnulty |
| 5,613,966 A | 3/1997 | Makower et al. |
| 5,620,415 A | 4/1997 | Lucey et al. |
| 5,620,447 A | 4/1997 | Smith et al. |
| 5,624,452 A | 4/1997 | Yates |
| 5,626,575 A | 5/1997 | Crenner |
| 5,626,607 A | 5/1997 | Malecki et al. |
| 5,626,608 A | 5/1997 | Cuny et al. |
| 5,627,584 A | 5/1997 | Nishikori et al. |
| 5,633,578 A | 5/1997 | Eggers et al. |
| 5,645,540 A | 7/1997 | Henniges et al. |
| 5,647,869 A | 7/1997 | Gobie et al. |
| 5,651,780 A | 7/1997 | Jackson et al. |

(56) References Cited

U.S. PATENT DOCUMENTS

| | | |
|---|---|---|
| 5,658,279 A | 8/1997 | Nardella et al. |
| 5,658,281 A | 8/1997 | Heard |
| 5,665,100 A | 9/1997 | Yoon |
| 5,666,105 A | 9/1997 | Furnish et al. |
| 5,667,517 A | 9/1997 | Hooven |
| 5,669,907 A | 9/1997 | Platt, Jr. et al. |
| 5,673,424 A | 9/1997 | Sawamura |
| 5,674,184 A | 10/1997 | Hassler, Jr. |
| 5,674,220 A | 10/1997 | Fox et al. |
| 5,683,349 A | 11/1997 | Makower et al. |
| 5,688,270 A | 11/1997 | Yates et al. |
| 5,693,045 A | 12/1997 | Eggers |
| 5,693,051 A | 12/1997 | Schulze et al. |
| 5,695,494 A | 12/1997 | Becker |
| 5,697,281 A | 12/1997 | Eggers et al. |
| 5,697,909 A | 12/1997 | Eggers et al. |
| 5,700,261 A | 12/1997 | Brinkerhoff |
| 5,702,386 A | 12/1997 | Stern et al. |
| 5,702,387 A | 12/1997 | Arts et al. |
| 5,703,390 A | 12/1997 | Austin et al. |
| 5,707,369 A | 1/1998 | Vaitekunas et al. |
| 5,709,680 A | 1/1998 | Yates et al. |
| 5,713,128 A | 2/1998 | Schrenk et al. |
| 5,713,895 A | 2/1998 | Lontine et al. |
| 5,713,896 A | 2/1998 | Nardella |
| 5,720,293 A | 2/1998 | Quinn et al. |
| 5,720,742 A | 2/1998 | Zacharias |
| 5,720,744 A | 2/1998 | Eggleston et al. |
| 5,720,745 A | 2/1998 | Farin et al. |
| 5,722,975 A | 3/1998 | Edwards et al. |
| 5,725,524 A | 3/1998 | Mulier et al. |
| 5,772,659 A | 3/1998 | Gluth |
| 5,735,848 A | 4/1998 | Yates et al. |
| 5,735,849 A | 4/1998 | Baden et al. |
| 5,743,456 A | 4/1998 | Jones et al. |
| 5,743,906 A | 4/1998 | Parins et al. |
| 5,746,210 A | 5/1998 | Benaron et al. |
| 5,746,740 A | 5/1998 | Nicholas |
| 5,746,759 A | 5/1998 | Meade et al. |
| 5,752,519 A | 5/1998 | Benaron et al. |
| 5,755,717 A | 5/1998 | Yates et al. |
| 5,759,185 A | 6/1998 | Grinberg |
| 5,762,609 A | 6/1998 | Benaron et al. |
| 5,766,167 A | 6/1998 | Eggers et al. |
| 5,769,791 A | 6/1998 | Benaron et al. |
| 5,769,841 A | 6/1998 | Odell et al. |
| 5,772,697 A | 6/1998 | Goldberger et al. |
| 5,776,092 A | 7/1998 | Farin et al. |
| 5,776,129 A | 7/1998 | Mersch |
| 5,776,155 A | 7/1998 | Beaupre et al. |
| 5,782,397 A | 7/1998 | Koukline |
| 5,785,658 A | 7/1998 | Benaron et al. |
| 5,792,139 A | 8/1998 | Chambers et al. |
| 5,792,178 A | 8/1998 | Welch et al. |
| 5,797,906 A | 8/1998 | Rhum et al. |
| 5,797,938 A | 8/1998 | Paraschac et al. |
| 5,797,941 A | 8/1998 | Schulze |
| 5,800,449 A | 9/1998 | Wales |
| 5,807,261 A | 9/1998 | Benaron et al. |
| 5,807,393 A | 9/1998 | Williamson, IV et al. |
| 5,807,395 A | 9/1998 | Muller et al. |
| 5,810,806 A | 9/1998 | Ritchart et al. |
| 5,810,811 A | 9/1998 | Yates et al. |
| 5,810,859 A | 9/1998 | Dimatteo et al. |
| 5,817,091 A | 10/1998 | Nardella et al. |
| 5,817,093 A | 10/1998 | Williamson, IV et al. |
| 5,817,119 A | 10/1998 | Klieman et al. |
| 5,827,271 A | 10/1998 | Buysse et al. |
| 5,827,279 A | 10/1998 | Hughett et al. |
| 5,827,299 A | 10/1998 | Thomason et al. |
| 5,830,231 A | 11/1998 | Geiges, Jr. |
| 5,833,690 A | 11/1998 | Yates et al. |
| 5,836,942 A | 11/1998 | Netherly et al. |
| 5,836,943 A | 11/1998 | Miller, III |
| 5,846,194 A | 12/1998 | Wasson et al. |
| 5,849,020 A | 12/1998 | Long et al. |
| 5,853,412 A | 12/1998 | Mayenbergr |
| 5,860,975 A | 1/1999 | Goble et al. |
| 5,873,873 A | 2/1999 | Smith et al. |
| 5,876,398 A | 3/1999 | Muller et al. |
| 5,876,401 A | 3/1999 | Schulze et al. |
| 5,885,277 A | 3/1999 | Korth |
| 5,891,095 A | 4/1999 | Eggers et al. |
| 5,891,141 A | 4/1999 | Rydell |
| 5,891,142 A | 4/1999 | Eggers et al. |
| 5,893,835 A | 4/1999 | Witt et al. |
| 5,893,873 A | 4/1999 | Rader et al. |
| 5,897,490 A | 4/1999 | Fox et al. |
| 5,897,523 A | 4/1999 | Wright et al. |
| 5,897,553 A | 4/1999 | Muller et al. |
| 5,897,569 A | 4/1999 | Kellogg et al. |
| 5,902,264 A | 5/1999 | Toso et al. |
| 5,902,301 A | 5/1999 | Olig |
| 5,904,709 A | 5/1999 | Arndt et al. |
| 5,906,613 A | 5/1999 | Mulier et al. |
| 5,910,152 A | 6/1999 | Bays |
| 5,928,137 A | 7/1999 | Green |
| 5,928,255 A | 7/1999 | Meade et al. |
| 5,928,256 A | 7/1999 | Riza |
| 5,908,402 A | 8/1999 | Blythe |
| 5,931,836 A | 8/1999 | Hatta et al. |
| 5,935,126 A | 8/1999 | Riza |
| 5,938,633 A | 8/1999 | Beaupre |
| 5,944,715 A | 8/1999 | Goble et al. |
| 5,944,718 A | 8/1999 | Austin et al. |
| 5,944,737 A | 8/1999 | Tsonton et al. |
| 5,947,284 A | 9/1999 | Foster |
| 5,947,984 A | 9/1999 | Whipple |
| 5,951,552 A | 9/1999 | Long et al. |
| 5,954,736 A | 9/1999 | Bishop et al. |
| 5,954,746 A | 9/1999 | Holthaus et al. |
| 5,957,943 A | 9/1999 | Vaitekunas |
| 5,961,514 A | 10/1999 | Long et al. |
| 5,968,062 A | 10/1999 | Thomas et al. |
| 5,968,074 A | 10/1999 | Prestel |
| 5,976,077 A | 11/1999 | Wittens et al. |
| 5,976,128 A | 11/1999 | Schilling et al. |
| 5,980,510 A | 11/1999 | Tsonton et al. |
| 5,980,516 A | 11/1999 | Mulier et al. |
| 5,987,346 A | 11/1999 | Benaron et al. |
| 5,993,380 A | 11/1999 | Yabe et al. |
| 5,993,447 A | 11/1999 | Blewett et al. |
| 5,995,875 A | 11/1999 | Blewett et al. |
| 5,997,533 A | 12/1999 | Kuhns |
| 6,003,517 A | 12/1999 | Sheffield et al. |
| 6,004,319 A | 12/1999 | Goble et al. |
| 6,004,335 A | 12/1999 | Vaitekunas et al. |
| 6,010,499 A | 1/2000 | Cobb |
| 6,010,516 A | 1/2000 | Hulka |
| 6,013,076 A | 1/2000 | Goble et al. |
| 6,015,406 A | 1/2000 | Goble et al. |
| 6,016,809 A | 1/2000 | Mulier et al. |
| D420,741 S | 2/2000 | Croley |
| 6,024,741 A | 2/2000 | Williamson, IV et al. |
| 6,024,744 A | 2/2000 | Kese et al. |
| 6,027,501 A | 2/2000 | Goble et al. |
| 6,027,622 A | 2/2000 | Palmer |
| 6,030,384 A | 2/2000 | Nezhat |
| 6,030,402 A | 2/2000 | Thompson et al. |
| 6,033,399 A | 3/2000 | Gines |
| 6,033,404 A | 3/2000 | Melzer et al. |
| 6,036,657 A | 3/2000 | Milliman et al. |
| 6,039,733 A | 3/2000 | Buysse et al. |
| 6,039,734 A | 3/2000 | Goble et al. |
| 6,039,736 A | 3/2000 | Platt, Jr. |
| 6,050,996 A | 4/2000 | Schmaltz et al. |
| 6,051,010 A | 4/2000 | Dimatteo et al. |
| 6,053,172 A | 4/2000 | Hovda et al. |
| 6,053,914 A | 4/2000 | Eggers et al. |
| 6,056,746 A | 5/2000 | Gobie et al. |
| 6,063,050 A | 5/2000 | Manna et al. |
| 6,063,075 A | 5/2000 | Mohori |
| 6,063,081 A | 5/2000 | Mulier et al. |
| 6,063,086 A | 5/2000 | Benecke et al. |

(56) References Cited

U.S. PATENT DOCUMENTS

| | | |
|---|---|---|
| 6,066,139 A | 5/2000 | Ryan et al. |
| 6,068,627 A | 5/2000 | Orszulak et al. |
| 6,068,647 A | 5/2000 | Witt et al. |
| 6,070,444 A | 6/2000 | Lontine et al. |
| 6,074,386 A | 6/2000 | Goble et al. |
| RE36,795 E | 7/2000 | Rydell |
| 6,083,191 A | 7/2000 | Rose |
| 6,086,586 A | 7/2000 | Hooven |
| 6,090,106 A | 7/2000 | Goble et al. |
| 6,090,120 A | 7/2000 | Wright et al. |
| 6,092,722 A | 7/2000 | Heinrichs et al. |
| 6,093,186 A | 7/2000 | Goble |
| 6,096,037 A | 8/2000 | Mulier et al. |
| 6,102,909 A | 8/2000 | Chen et al. |
| 6,106,521 A | 8/2000 | Blewett et al. |
| 6,109,268 A | 8/2000 | Thapliyal et al. |
| 6,110,171 A | 8/2000 | Rydell |
| 6,113,591 A | 9/2000 | Whayne et al. |
| 6,113,594 A | 9/2000 | Savage |
| 6,113,596 A | 9/2000 | Hooven et al. |
| 6,113,598 A | 9/2000 | Baker |
| 6,117,152 A | 9/2000 | Hultema |
| 6,120,501 A | 9/2000 | Long et al. |
| H1904 H | 10/2000 | Yates |
| 6,132,429 A | 10/2000 | Baker |
| 6,135,998 A | 10/2000 | Palanker |
| 6,139,519 A | 10/2000 | Blythe |
| 6,139,547 A | 10/2000 | Lontine et al. |
| 6,142,992 A | 11/2000 | Cheng et al. |
| 6,152,923 A | 11/2000 | Ryan |
| 6,159,146 A | 12/2000 | El Gazayerli |
| 6,162,235 A | 12/2000 | Vaitekunas |
| 6,165,175 A | 12/2000 | Wampler et al. |
| 6,168,605 B1 | 1/2001 | Measamer et al. |
| 6,171,304 B1 | 1/2001 | Netherly et al. |
| 6,174,308 B1 | 1/2001 | Goble et al. |
| 6,174,309 B1 | 1/2001 | Wrublewski et al. |
| 6,179,834 B1 | 1/2001 | Buysse et al. |
| 6,186,147 B1 | 2/2001 | Cobb |
| 6,187,003 B1 | 2/2001 | Buysse et al. |
| 6,187,026 B1 | 2/2001 | Devlin et al. |
| 6,190,383 B1 | 2/2001 | Schmaltz et al. |
| 6,190,385 B1 | 2/2001 | Tom et al. |
| 6,190,386 B1 | 2/2001 | Rydell |
| 6,193,129 B1 | 2/2001 | Bittner et al. |
| 6,193,653 B1 | 2/2001 | Evans et al. |
| 6,193,713 B1 | 2/2001 | Geistert et al. |
| 6,197,026 B1 | 3/2001 | Farin et al. |
| 6,203,541 B1 | 3/2001 | Keppel |
| 6,206,823 B1 | 3/2001 | Kolata et al. |
| 6,206,844 B1 | 3/2001 | Reichel et al. |
| 6,206,875 B1 | 3/2001 | Long et al. |
| 6,206,877 B1 | 3/2001 | Kese et al. |
| 6,210,403 B1 | 4/2001 | Klicek |
| 6,210,405 B1 | 4/2001 | Goble et al. |
| 6,214,003 B1 | 4/2001 | Morgan et al. |
| 6,214,023 B1 | 4/2001 | Whipple et al. |
| 6,228,023 B1 | 5/2001 | Zaslavsky et al. |
| 6,228,055 B1 | 5/2001 | Foerster et al. |
| 6,228,080 B1 | 5/2001 | Gines |
| 6,228,081 B1 | 5/2001 | Goble |
| 6,228,083 B1 | 5/2001 | Lands et al. |
| 6,234,178 B1 | 5/2001 | Gobie et al. |
| 6,237,604 B1 | 5/2001 | Burnside et al. |
| 6,238,366 B1 | 5/2001 | Savage et al. |
| 6,238,392 B1 | 5/2001 | Gary |
| 6,238,393 B1 | 5/2001 | Mulier et al. |
| 6,242,741 B1 | 6/2001 | Miller et al. |
| 6,246,912 B1 | 6/2001 | Sluijter et al. |
| 6,251,106 B1 | 6/2001 | Becker et al. |
| 6,251,110 B1 | 6/2001 | Wampler |
| 6,254,623 B1 | 7/2001 | Haibel et al. |
| 6,257,241 B1 | 7/2001 | Wampler |
| 6,258,085 B1 | 7/2001 | Eggleston |
| 6,261,286 B1 | 7/2001 | Goble et al. |
| 6,267,761 B1 | 7/2001 | Ryan |
| 6,270,497 B1 | 8/2001 | Sekino et al. |
| 6,273,862 B1 | 8/2001 | Privitera et al. |
| 6,277,114 B1 | 8/2001 | Bullivant et al. |
| 6,277,115 B1 | 8/2001 | Saadat |
| 6,277,117 B1 | 8/2001 | Tetzlaff et al. |
| 6,280,398 B1 | 8/2001 | Ritchart et al. |
| 6,280,407 B1 | 8/2001 | Manna et al. |
| 6,280,441 B1 | 8/2001 | Ryan |
| 6,283,963 B1 | 9/2001 | Regula |
| 6,287,344 B1 | 9/2001 | Wampler |
| 6,293,942 B1 | 9/2001 | Goble et al. |
| 6,293,945 B1 | 9/2001 | Parins et al. |
| 6,296,637 B1 | 10/2001 | Thorne et al. |
| 6,296,640 B1 | 10/2001 | Wampler et al. |
| 6,298,650 B1 | 10/2001 | Kirwan, Jr. |
| 6,302,903 B1 | 10/2001 | Mulier et al. |
| 6,306,131 B1 | 10/2001 | Hareyama et al. |
| 6,306,134 B1 | 10/2001 | Goble et al. |
| 6,308,089 B1 | 10/2001 | von der Ruhr et al. |
| 6,309,400 B2 | 10/2001 | Beaupre |
| 6,312,426 B1 | 11/2001 | Goldberg et al. |
| 6,315,777 B1 | 11/2001 | Comben |
| 6,319,221 B1 | 11/2001 | Savage et al. |
| 6,322,494 B1 | 11/2001 | Bullivant et al. |
| 6,322,549 B1 | 11/2001 | Eggers et al. |
| 6,322,561 B1 | 11/2001 | Eggers et al. |
| 6,325,795 B1 | 12/2001 | Lindemann et al. |
| 6,325,799 B1 | 12/2001 | Goble |
| 6,325,811 B1 | 12/2001 | Messerly |
| 6,328,736 B1 | 12/2001 | Mulier et al. |
| 6,328,751 B1 | 12/2001 | Beaupre |
| 6,331,181 B1 | 12/2001 | Tierney et al. |
| 6,334,068 B1 | 12/2001 | Hacker |
| 6,334,861 B1 | 1/2002 | Chandler et al. |
| 6,336,926 B1 | 1/2002 | Goble et al. |
| 6,341,807 B2 | 1/2002 | Cetnar |
| 6,348,051 B1 | 2/2002 | Farin et al. |
| 6,371,967 B1 | 2/2002 | Long et al. |
| 6,352,532 B1 | 3/2002 | Kramer et al. |
| 6,352,536 B1 | 3/2002 | Buysse et al. |
| 6,358,248 B1 | 3/2002 | Mulier et al. |
| 6,358,249 B1 | 3/2002 | Chen et al. |
| 6,358,267 B1 | 3/2002 | Murakami |
| 6,361,534 B1 | 3/2002 | Chen et al. |
| 6,364,877 B1 | 4/2002 | Gobie et al. |
| 6,364,879 B1 | 4/2002 | Chen et al. |
| D457,958 S | 5/2002 | Dycus |
| 6,383,183 B1 | 5/2002 | Sekino et al. |
| 6,387,092 B1 | 5/2002 | Burnside et al. |
| 6,387,109 B1 | 5/2002 | Davison et al. |
| 6,391,024 B1 | 5/2002 | Sun et al. |
| 6,391,025 B1 | 5/2002 | Weinstein et al. |
| 6,398,779 B1 | 6/2002 | Buysse |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,747 B1 | 6/2002 | Lindemann et al. |
| 6,402,748 B1 | 6/2002 | Schoenman et al. |
| 6,406,475 B1 | 6/2002 | Wenzler et al. |
| 6,409,722 B1 | 6/2002 | Hoey et al. |
| 6,409,724 B1 | 6/2002 | Penny et al. |
| 6,409,728 B1 | 6/2002 | Ehr et al. |
| 6,416,486 B1 | 7/2002 | Wampler |
| 6,416,509 B1 | 7/2002 | Goble et al. |
| 6,423,057 B1 | 7/2002 | He et al. |
| 6,423,082 B1 | 7/2002 | Houser et al. |
| 6,432,118 B1 | 8/2002 | Messerly |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,968 B1 | 9/2002 | Holthaus et al. |
| 6,443,970 B1 | 9/2002 | Schulze |
| 6,451,013 B1 | 9/2002 | Bays et al. |
| 6,451,018 B1 | 9/2002 | Lands et al. |
| 6,454,764 B1 | 9/2002 | Fleenor et al. |
| 6,454,781 B1 | 9/2002 | Witt et al. |
| 6,454,782 B1 | 9/2002 | Schwemberger |

(56) References Cited

U.S. PATENT DOCUMENTS

| | | |
|---|---|---|
| 6,458,078 B1 | 10/2002 | Luedtke et al. |
| 6,458,128 B1 | 10/2002 | Schulze |
| 6,458,130 B1 | 10/2002 | Frazier et al. |
| 6,458,142 B1 | 10/2002 | Faller et al. |
| 6,461,352 B2 | 10/2002 | Morgan et al. |
| 6,464,689 B1 | 10/2002 | Qin et al. |
| 6,464,702 B2 | 10/2002 | Schulze et al. |
| 6,464,704 B2 | 10/2002 | Schmaltz et al. |
| 6,468,275 B1 | 10/2002 | Wampler et al. |
| 6,468,286 B2 | 10/2002 | Mastri et al. |
| 6,472,442 B1 | 10/2002 | Masubuchi |
| 6,475,217 B1 | 11/2002 | Platt |
| 6,478,030 B1 | 11/2002 | Shaceton et al. |
| 6,482,202 B1 | 11/2002 | Gobie et al. |
| 6,485,490 B2 | 11/2002 | Wampler et al. |
| 6,488,507 B1 | 12/2002 | Stoloff et al. |
| 6,488,680 B1 | 12/2002 | Francischelli et al. |
| 6,491,690 B1 | 12/2002 | Goble et al. |
| 6,491,708 B2 | 12/2002 | Madan et al. |
| 6,493,589 B1 | 12/2002 | Medhkour et al. |
| 6,494,877 B2 | 12/2002 | Odell et al. |
| 6,494,902 B2 | 12/2002 | Hoey et al. |
| 6,497,705 B2 | 12/2002 | Comben |
| 6,500,176 B1 | 12/2002 | Truckal et al. |
| 6,500,188 B2 | 12/2002 | Harper et al. |
| 6,503,263 B2 | 1/2003 | Adams |
| 6,506,189 B1 | 1/2003 | Rittman et al. |
| 6,506,208 B2 | 1/2003 | Hunt et al. |
| 6,510,854 B2 | 1/2003 | Goble et al. |
| 6,511,476 B2 | 1/2003 | Hareyama |
| 6,511,480 B1 | 1/2003 | Tetzlaff et al. |
| 6,514,252 B2 | 2/2003 | Nezhat et al. |
| 6,517,536 B2 | 2/2003 | Hooven et al. |
| 6,517,538 B1 | 2/2003 | Jacob et al. |
| 6,518,163 B2 | 2/2003 | Sakuyama et al. |
| 6,526,320 B2 | 2/2003 | Mitchell |
| 6,527,771 B1 | 3/2003 | Weadock et al. |
| 6,533,784 B2 | 3/2003 | Truckal et al. |
| 6,534,770 B2 | 3/2003 | Miller et al. |
| 6,537,248 B2 | 3/2003 | Mulier et al. |
| 6,537,272 B2 | 3/2003 | Christopherson et al. |
| 6,540,695 B1 | 4/2003 | Burbank et al. |
| 6,543,456 B1 | 4/2003 | Freeman |
| 6,547,783 B1 | 4/2003 | Vilendrer et al. |
| 6,547,786 B1 | 4/2003 | Goble et al. |
| 6,554,829 B2 | 4/2003 | Schulze et al. |
| 6,558,379 B1 | 5/2003 | Batchelor et al. |
| 6,558,383 B2 | 5/2003 | Cunningham et al. |
| 6,561,983 B2 | 5/2003 | Cronin et al. |
| 6,562,037 B2 | 5/2003 | Paton et al. |
| 6,565,559 B2 | 5/2003 | Eggleston |
| 6,565,560 B1 | 5/2003 | Goble et al. |
| 6,569,105 B1 | 5/2003 | Kortenbach et al. |
| 6,569,109 B2 | 5/2003 | Sakural et al. |
| 6,572,615 B2 | 6/2003 | Schulze et al. |
| 6,579,289 B2 | 6/2003 | Schnitzier |
| 6,582,424 B2 | 6/2003 | Fleenor et al. |
| 6,582,427 B1 | 6/2003 | Goble et al. |
| 6,584,360 B2 | 6/2003 | Francischelli et al. |
| D477,408 S | 7/2003 | Bromley |
| 6,585,732 B2 | 7/2003 | Mulier et al. |
| 6,585,733 B2 | 7/2003 | Wellman |
| 6,585,735 B1 | 7/2003 | Frazier et al. |
| 6,589,200 B1 | 7/2003 | Schwemberger et al. |
| 6,591,719 B1 | 7/2003 | Poole et al. |
| 6,592,582 B2 | 7/2003 | Hess et al. |
| 6,594,518 B1 | 7/2003 | Benaron et al. |
| 6,602,227 B1 | 8/2003 | Cimino et al. |
| 6,602,249 B1 | 8/2003 | Stoddard et al. |
| 6,602,252 B2 | 8/2003 | Mollenauer |
| 6,605,036 B1 | 8/2003 | Wild |
| 6,607,529 B1 | 8/2003 | Jones et al. |
| 6,610,060 B2 | 8/2003 | Mulier et al. |
| 6,611,793 B1 | 8/2003 | Burnside et al. |
| 6,613,048 B2 | 9/2003 | Mulier et al. |
| 6,616,656 B2 | 9/2003 | Brommersma |
| 6,616,660 B1 | 9/2003 | Platt |
| 6,616,661 B2 | 9/2003 | Wellman et al. |
| 6,620,157 B1 | 9/2003 | Dabney et al. |
| 6,620,161 B2 | 9/2003 | Schulze et al. |
| 6,623,482 B2 | 9/2003 | Pendekanti et al. |
| 6,623,515 B2 | 9/2003 | Muller et al. |
| 6,626,901 B1 | 9/2003 | Treat et al. |
| 6,629,974 B2 | 10/2003 | Penny et al. |
| 6,638,274 B2 | 10/2003 | Yamamoto |
| 6,648,883 B2 | 11/2003 | Francischelli et al. |
| 6,652,514 B2 | 11/2003 | Ellman et al. |
| 6,652,521 B2 | 11/2003 | Schulze |
| 6,656,110 B1 | 12/2003 | Infon et al. |
| 6,656,175 B2 | 12/2003 | Francischelli et al. |
| 6,656,177 B2 | 12/2003 | Truckai |
| 6,656,178 B1 | 12/2003 | Hess et al. |
| 6,660,017 B2 | 12/2003 | Beaupre |
| 6,662,050 B2 | 12/2003 | Olson |
| 6,662,127 B2 | 12/2003 | Wiener et al. |
| 6,663,622 B1 | 12/2003 | Foley et al. |
| 6,663,627 B2 | 12/2003 | Francischelli et al. |
| 6,663,628 B2 | 12/2003 | Peters |
| 6,666,865 B2 | 12/2003 | Platt |
| 6,676,660 B2 | 1/2004 | Wampler et al. |
| 6,678,621 B2 | 1/2004 | Wiener et al. |
| 6,679,882 B1 | 1/2004 | Komerup |
| 6,682,527 B2 | 1/2004 | Strul |
| 6,682,528 B2 | 1/2004 | Frazier et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,692,450 B1 | 2/2004 | Coleman |
| 6,692,489 B1 | 2/2004 | Heim et al. |
| 6,695,837 B2 | 2/2004 | Howell |
| 6,695,840 B2 | 2/2004 | Schulze |
| 6,699,240 B2 | 3/2004 | Francischelli et al. |
| 6,706,038 B2 | 3/2004 | Francischelli et al. |
| 6,706,039 B2 | 3/2004 | Mulier et al. |
| 6,709,432 B2 | 3/2004 | Ferek-Petric |
| 6,696,838 B2 | 4/2004 | Wellman et al. |
| 6,723,091 B2 | 4/2004 | Goble et al. |
| 6,726,683 B1 | 4/2004 | Shaw |
| 6,726,686 B2 | 4/2004 | Buysse et al. |
| 6,733,498 B2 | 5/2004 | Paton et al. |
| 6,736,810 B2 | 5/2004 | Hoey et al. |
| 6,740,084 B2 | 5/2004 | Ryan |
| 6,740,085 B2 | 5/2004 | Hareyama et al. |
| 6,740,102 B2 | 5/2004 | Hess et al. |
| 6,743,229 B2 | 6/2004 | Buysse et al. |
| 6,752,804 B2 | 6/2004 | Simpson et al. |
| 6,755,825 B2 | 6/2004 | Schoenman et al. |
| 6,755,827 B2 | 6/2004 | Mulier et al. |
| 6,755,841 B2 | 6/2004 | Fraser et al. |
| 6,764,487 B2 | 7/2004 | Mulier et al. |
| 6,768,846 B2 | 7/2004 | Goble et al. |
| 6,770,071 B2 | 8/2004 | Woloszko et al. |
| 6,770,072 B1 | 8/2004 | Truckal et al. |
| 6,772,660 B2 | 8/2004 | Tsai et al. |
| 6,773,409 B2 | 8/2004 | Truckal et al. |
| 6,773,434 B2 | 8/2004 | Ciarrocca |
| 6,773,435 B2 | 8/2004 | Schulze et al. |
| 6,773,444 B2 | 8/2004 | Messerly |
| 6,775,575 B2 | 8/2004 | Bommannan et al. |
| 6,776,130 B2 | 8/2004 | Miyakoshi et al. |
| 6,776,780 B2 | 8/2004 | Muller et al. |
| 6,780,180 B1 | 8/2004 | Goble et al. |
| 6,786,906 B1 | 9/2004 | Cobb |
| 6,790,217 B2 | 9/2004 | Schulze et al. |
| 6,796,828 B2 | 9/2004 | Ehr et al. |
| 6,796,981 B2 | 9/2004 | Wham et al. |
| 6,807,444 B2 | 10/2004 | Tu et al. |
| 6,807,968 B2 | 10/2004 | Francischelli et al. |
| 6,808,518 B2 | 10/2004 | Wellman et al. |
| 6,808,525 B2 | 10/2004 | Latterell et al. |
| 6,814,745 B2 | 11/2004 | Prestel |
| 6,821,273 B2 | 11/2004 | Mollenauer |
| 6,827,715 B2 | 12/2004 | Francischelli et al. |
| 6,827,717 B2 | 12/2004 | Brommersma et al. |

(56) References Cited

U.S. PATENT DOCUMENTS

| | | |
|---|---|---|
| 6,827,725 B2 | 12/2004 | Batchelor et al. |
| 6,830,569 B2 | 12/2004 | Thompson et al. |
| 6,832,111 B2 | 12/2004 | Tu et al. |
| 6,832,985 B2 | 12/2004 | Irion et al. |
| 6,832,998 B2 | 12/2004 | Goble |
| 6,835,082 B2 | 12/2004 | Gonnering |
| 6,835,195 B2 | 12/2004 | Schulze et al. |
| 6,837,887 B2 | 1/2005 | Woloszko et al. |
| 6,843,789 B2 | 1/2005 | Goble |
| 6,849,073 B2 | 2/2005 | Hoy et al. |
| 6,852,112 B2 | 2/2005 | Platt |
| 6,855,142 B2 | 2/2005 | Harano et al. |
| 6,855,145 B2 | 2/2005 | Ciarrocca |
| 6,858,028 B2 | 2/2005 | Mulier et al. |
| 6,860,881 B2 | 3/2005 | Sturm |
| 6,860,894 B1 | 3/2005 | Pittman |
| 6,887,240 B1 | 5/2005 | Lands et al. |
| 6,889,694 B2 | 5/2005 | Hooven |
| 6,893,435 B2 | 5/2005 | Goble |
| 6,893,441 B2 | 5/2005 | Brommersma et al. |
| 6,899,710 B2 | 5/2005 | Hooven |
| 6,905,498 B2 | 6/2005 | Hooven |
| 6,906,497 B2 | 6/2005 | Truckai et al. |
| 6,908,420 B2 | 6/2005 | Zaoralek et al. |
| 6,908,472 B2 | 6/2005 | Wiener et al. |
| 6,911,019 B2 | 6/2005 | Mulier et al. |
| 6,913,579 B2 | 7/2005 | Truckai et al. |
| 6,916,318 B2 | 7/2005 | Francischelli et al. |
| 6,918,880 B2 | 7/2005 | Brookner et al. |
| 6,923,803 B2 | 8/2005 | Goble |
| 6,923,804 B2 | 8/2005 | Eggers et al. |
| 6,923,806 B2 | 8/2005 | Hooven et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,932,810 B2 | 8/2005 | Ryan |
| 6,932,811 B2 | 8/2005 | Hooven et al. |
| 6,937,033 B2 | 8/2005 | Boronkay et al. |
| 6,939,347 B2 | 9/2005 | Thompson |
| 6,942,660 B2 | 9/2005 | Pantera et al. |
| 6,942,662 B2 | 9/2005 | Goble et al. |
| 6,945,972 B2 | 9/2005 | Frigg et al. |
| 6,945,981 B2 | 9/2005 | Donofrio et al. |
| 6,948,503 B2 | 9/2005 | Refior et al. |
| 6,949,098 B2 | 9/2005 | Muller et al. |
| 6,958,063 B1 | 10/2005 | Soll et al. |
| 6,960,209 B2 | 11/2005 | Ciague et al. |
| 6,960,210 B2 | 11/2005 | Lands et al. |
| 6,962,587 B2 | 11/2005 | Johnson et al. |
| 6,962,589 B2 | 11/2005 | Mulier et al. |
| 6,966,907 B2 | 11/2005 | Goble |
| 6,966,909 B2 | 11/2005 | Marshall et al. |
| 6,971,988 B2 | 12/2005 | Orban et al. |
| 6,974,453 B2 | 12/2005 | Woloszko et al. |
| 6,974,464 B2 | 12/2005 | Quijano |
| 6,976,969 B2 | 12/2005 | Messerly |
| 6,979,332 B2 | 12/2005 | Adams |
| 6,984,231 B2 | 1/2006 | Goble et al. |
| 6,984,233 B2 | 1/2006 | Hooven |
| 6,984,826 B2 | 1/2006 | Miller et al. |
| 6,984,921 B1 | 1/2006 | Kosterman et al. |
| 6,989,010 B2 | 1/2006 | Francischelli et al. |
| 6,994,705 B2 | 2/2006 | Nobis et al. |
| 6,997,735 B2 | 2/2006 | Ehr et al. |
| 6,997,935 B2 | 2/2006 | Anderson et al. |
| 7,001,380 B2 | 2/2006 | Goble |
| 7,001,415 B2 | 2/2006 | Hooven |
| 7,011,657 B2 | 3/2006 | Truckai et al. |
| 7,025,764 B2 | 4/2006 | Paton et al. |
| 7,029,470 B2 | 4/2006 | Francischelli et al. |
| 7,033,351 B2 | 4/2006 | Howell |
| 7,033,354 B2 | 4/2006 | Keppel |
| 7,033,356 B2 | 4/2006 | Latterell et al. |
| 7,041,096 B2 | 5/2006 | Malis |
| 7,041,102 B2 | 5/2006 | Truckai et al. |
| 7,044,948 B2 | 5/2006 | Keppel |
| 7,044,949 B2 | 5/2006 | Orszulak |
| 7,044,950 B2 | 5/2006 | Yamamoto |
| 7,048,687 B1 | 5/2006 | Reuss et al. |
| 7,049,599 B2 | 5/2006 | Miller et al. |
| 7,052,494 B2 | 5/2006 | Goble et al. |
| 7,060,063 B2 | 6/2006 | Marion et al. |
| 7,063,699 B2 | 6/2006 | Hess et al. |
| 7,066,933 B2 | 6/2006 | Hagg |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,090,673 B2 | 8/2006 | Dycus |
| 7,094,202 B2 | 8/2006 | Nobis et al. |
| 7,094,235 B2 | 8/2006 | Francischelli |
| 7,097,644 B2 | 8/2006 | Long |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,104,834 B2 | 9/2006 | Robinson et al. |
| 7,104,989 B2 | 9/2006 | Skarda |
| 7,108,695 B2 | 9/2006 | Witt et al. |
| 7,111,769 B2 | 9/2006 | Wales et al. |
| 7,112,201 B2 | 9/2006 | Truckai et al. |
| RE39,358 E | 10/2006 | Goble |
| 7,116,157 B2 | 10/2006 | Ross |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson |
| 7,125,409 B2 | 10/2006 | Truckai et al. |
| 7,126,125 B2 | 10/2006 | Miller et al. |
| 7,131,445 B2 | 11/2006 | Amoah |
| 7,131,860 B2 | 11/2006 | Sartor |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse |
| D533,942 S | 12/2006 | Kerr et al. |
| 7,147,635 B2 | 12/2006 | Ciarrocca |
| 7,147,637 B2 | 12/2006 | Goble |
| 7,147,638 B2 | 12/2006 | Chapman et al. |
| 7,150,097 B2 | 12/2006 | Sremcich |
| 7,150,748 B2 | 12/2006 | Ebbutt |
| 7,150,749 B2 | 12/2006 | Dycus et al. |
| 7,153,300 B2 | 12/2006 | Goble |
| 7,156,843 B2 | 1/2007 | Skarda |
| 7,156,845 B2 | 1/2007 | Mulier et al. |
| 7,156,846 B2 | 1/2007 | Dycus et al. |
| 7,159,750 B2 | 1/2007 | Racenet et al. |
| 7,160,293 B2 | 1/2007 | Sturm et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,105 B2 | 1/2007 | Mulier et al. |
| 7,169,115 B2 | 1/2007 | Nobis et al. |
| 7,169,144 B2 | 1/2007 | Hoey |
| 7,169,145 B2 | 1/2007 | Isaacson |
| 7,169,146 B2 | 1/2007 | Truckai et al. |
| 7,172,591 B2 | 2/2007 | Harano et al. |
| 7,179,254 B2 | 2/2007 | Pendkanti |
| 7,179,258 B2 | 2/2007 | Buysse et al. |
| 7,182,604 B2 | 2/2007 | Ehr et al. |
| 7,186,252 B2 | 3/2007 | Nobis et al. |
| 7,186,253 B2 | 3/2007 | Truckai et al. |
| 7,187,790 B2 | 3/2007 | Sabol |
| 7,189,231 B2 | 3/2007 | Claque et al. |
| 7,189,232 B2 | 3/2007 | Scholl et al. |
| 7,189,233 B2 | 3/2007 | Truckai et al. |
| 7,191,015 B2 | 3/2007 | Lamson et al. |
| 7,195,627 B2 | 3/2007 | Amoah |

(56) References Cited

U.S. PATENT DOCUMENTS

| | | |
|---|---|---|
| 7,195,630 B2 | 3/2007 | Ciarrocca |
| 7,195,631 B2 | 3/2007 | Dumbauld |
| 7,204,835 B2 | 4/2007 | Latterell et al. |
| 7,207,471 B2 | 4/2007 | Heinrich et al. |
| 7,207,990 B2 | 4/2007 | Lands et al. |
| D541,938 S | 5/2007 | Kerr et al. |
| 7,211,081 B2 | 5/2007 | Goble |
| 7,211,084 B2 | 5/2007 | Goble |
| 7,214,224 B2 | 5/2007 | Goble |
| 7,216,001 B2 | 5/2007 | Hacker et al. |
| 7,220,260 B2 | 5/2007 | Fleming |
| 7,220,951 B2 | 5/2007 | Truckal et al. |
| 7,223,239 B2 | 5/2007 | Schulze et al. |
| 7,223,265 B2 | 5/2007 | Keppel |
| 7,226,447 B2 | 6/2007 | Uchida |
| 7,229,307 B2 | 6/2007 | Ehr et al. |
| 7,231,971 B2 | 6/2007 | McCalvin |
| 7,232,439 B2 | 6/2007 | Ciarrocca |
| 7,232,440 B2 | 6/2007 | Dumbald et al. |
| 7,235,048 B2 | 6/2007 | Rein et al. |
| 7,235,073 B2 | 6/2007 | Levine et al. |
| 7,237,708 B1 | 7/2007 | Guy |
| 7,241,296 B2 | 7/2007 | Buysse et al. |
| 7,247,141 B2 | 7/2007 | Makin et al. |
| 7,247,155 B2 | 7/2007 | Hoey et al. |
| 7,250,048 B2 | 7/2007 | Francischelli et al. |
| 7,250,051 B2 | 7/2007 | Francischelli |
| 7,235,072 B2 | 8/2007 | Sartor et al. |
| 7,252,667 B2 | 8/2007 | Moses |
| 7,255,694 B2 | 8/2007 | Keppel |
| 7,255,696 B2 | 8/2007 | Goble et al. |
| 7,255,697 B2 | 8/2007 | Dycus et al. |
| 7,259,340 B2 | 8/2007 | Blaha et al. |
| 7,261,711 B2 | 8/2007 | Mulier et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,273,483 B2 | 9/2007 | Weiner et al. |
| 7,276,068 B2 | 10/2007 | Johnson et al. |
| 7,278,994 B2 | 10/2007 | Goble |
| 7,282,048 B2 | 10/2007 | Goble et al. |
| 7,282,049 B2 | 10/2007 | Oraszulak et al. |
| 7,291,161 B2 | 11/2007 | Hooven |
| 7,297,145 B2 | 11/2007 | Woloszko et al. |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,557 B2 | 12/2007 | Wham |
| 7,309,325 B2 | 12/2007 | Mulier et al. |
| 7,309,849 B2 | 12/2007 | Truckal et al. |
| 7,311,560 B2 | 12/2007 | Ehr et al. |
| 7,311,706 B2 | 12/2007 | Schoenman et al. |
| 7,311,707 B2 | 12/2007 | Hagg et al. |
| 7,311,709 B2 | 12/2007 | Truckai et al. |
| 7,322,975 B2 | 1/2008 | Gobie et al. |
| 7,329,256 B2 | 2/2008 | Johnson et al. |
| 7,335,997 B2 | 2/2008 | Weiner |
| 7,344,532 B2 | 3/2008 | Goble et al. |
| 7,347,858 B2 | 3/2008 | Francischelli et al. |
| RE40,279 E | 4/2008 | Sluijter et al. |
| D567,943 S | 4/2008 | Moses et al. |
| 7,353,068 B2 | 4/2008 | Tanake et al. |
| 7,354,435 B2 | 4/2008 | Farin et al. |
| 7,354,440 B2 | 4/2008 | Truckal et al. |
| 7,354,443 B2 | 4/2008 | Moll et al. |
| 7,364,577 B2 | 4/2008 | Wham et al. |
| 7,364,578 B2 | 4/2008 | Francischelli et al. |
| 7,364,579 B2 | 4/2008 | Miller et al. |
| 7,367,972 B2 | 5/2008 | Francischelli et al. |
| 7,367,976 B2 | 5/2008 | Lawes et al. |
| 7,371,246 B2 | 5/2008 | Viola |
| 7,377,902 B2 | 5/2008 | Burbank et al. |
| 7,377,918 B2 | 5/2008 | Amoah |
| 7,377,920 B2 | 5/2008 | Buysse et al. |
| RE40,388 E | 6/2008 | Gines |
| 7,381,209 B2 | 6/2008 | Truckal et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,416,101 B2 | 8/2008 | Shelton |
| 7,416,437 B2 | 8/2008 | Sartor et al. |
| 7,419,487 B2 | 9/2008 | Johnson et al. |
| 7,422,139 B2 | 9/2008 | Shelton et al. |
| 7,422,588 B2 | 9/2008 | Muller et al. |
| 7,424,965 B2 | 9/2008 | Racenet et al. |
| 7,425,835 B2 | 9/2008 | Eisele |
| 7,426,415 B2 | 9/2008 | Kuhner |
| 7,431,720 B2 | 10/2008 | Pendekanti et al. |
| 7,431,721 B2 | 10/2008 | Paton et al. |
| 7,435,249 B2 | 10/2008 | Buysse et al. |
| 7,435,250 B2 | 10/2008 | Francischelli et al. |
| 7,442,167 B2 | 10/2008 | Dunki-Jacobs |
| 7,442,193 B2 | 10/2008 | Shelds |
| 7,442,194 B2 | 10/2008 | Dumbauld |
| 7,445,621 B2 | 11/2008 | Dumbauld et al. |
| 7,458,972 B2 | 12/2008 | Keppel |
| 7,464,846 B2 | 12/2008 | Shelton et al. |
| 7,470,272 B2 | 12/2008 | Muller et al. |
| 7,473,250 B2 | 1/2009 | Makin et al. |
| 7,473,253 B2 | 1/2009 | Dycus et al. |
| 7,476,233 B1 | 1/2009 | Wiener et al. |
| 7,481,808 B2 | 1/2009 | Kovfman et al. |
| 7,491,199 B2 | 2/2009 | Goble et al. |
| 7,497,858 B2 | 3/2009 | Chapelon et al. |
| 7,811,283 B2 | 10/2010 | Moses et al. |
| 7,841,765 B2 | 11/2010 | Keller |
| 8,561,615 B2 | 10/2013 | Pannell et al. |
| 8,784,417 B2 | 7/2014 | Hanna |
| 8,808,288 B2 | 8/2014 | Rescheke |
| 9,161,813 B2 | 10/2015 | Benamou |
| 2001/0037110 A1 | 11/2001 | Schmaltz |
| 2001/0039417 A1 | 11/2001 | Harano et al. |
| 2002/0052599 A1 | 5/2002 | Goble |
| 2002/0115997 A1 | 8/2002 | Truckai |
| 2002/0120262 A1 | 8/2002 | Bek |
| 2002/0120266 A1 | 8/2002 | Truckai |
| 2002/0128650 A1 | 9/2002 | McClurken |
| 2002/0151884 A1 | 10/2002 | Hoey et al. |
| 2002/0161363 A1 | 10/2002 | Fodor et al. |
| 2002/0165541 A1 | 11/2002 | Whitman |
| 2002/0188294 A1 | 12/2002 | Couture et al. |
| 2003/0004510 A1 | 1/2003 | Wham |
| 2003/0014052 A1 | 1/2003 | Buysse |
| 2003/0065327 A1 | 4/2003 | Wellman |
| 2003/0065358 A1 | 4/2003 | Frecker et al. |
| 2003/0069571 A1 | 4/2003 | Treat |
| 2003/0109871 A1 | 6/2003 | Johnson |
| 2003/0114845 A1 | 6/2003 | Paton et al. |
| 2003/0114848 A1 | 6/2003 | Cobb |
| 2003/0114851 A1 | 6/2003 | Csaba et al. |
| 2003/0125728 A1 | 7/2003 | Nezhat et al. |
| 2003/0125731 A1 | 7/2003 | Smith et al. |
| 2003/0125734 A1 | 7/2003 | Mollenauer |
| 2003/0139741 A1 | 7/2003 | Goble et al. |
| 2003/0181910 A1 | 9/2003 | Dycus |
| 2003/0199863 A1 | 10/2003 | Swanson et al. |
| 2003/0199870 A1 | 10/2003 | Truckai |
| 2003/0229344 A1 | 12/2003 | Dycus et al. |
| 2003/0236549 A1 | 12/2003 | Bonadio et al. |
| 2004/0006340 A1 | 1/2004 | Latterell |
| 2004/0068274 A1 | 4/2004 | Hoover |
| 2004/0068304 A1 | 4/2004 | Paton et al. |
| 2004/0073247 A1 | 4/2004 | Loshakove et al. |
| 2004/0082946 A1 | 4/2004 | Malis et al. |
| 2004/0092922 A1 | 5/2004 | Kadziauskas et al. |
| 2004/0122423 A1 | 6/2004 | Dycus |
| 2004/0162557 A1 | 8/2004 | Tetzlaff et al. |
| 2004/0193148 A1 | 9/2004 | Wham |
| 2004/0215127 A1 | 10/2004 | Kadziauskas et al. |
| 2004/0225288 A1 | 11/2004 | Buysse |
| 2004/0250419 A1 | 12/2004 | Sremich |
| 2005/0004564 A1 | 1/2005 | Wham et al. |

(56) References Cited

U.S. PATENT DOCUMENTS

| | | |
|---|---|---|
| 2005/0021027 A1 | 1/2005 | Shields et al. |
| 2005/0033282 A1 | 2/2005 | Hooven |
| 2005/0033352 A1 | 2/2005 | Zepf |
| 2005/0080319 A1 | 4/2005 | Dinkler II et al. |
| 2005/0090815 A1 | 4/2005 | Francischelli et al. |
| 2005/0096681 A1 | 5/2005 | Desinger et al. |
| 2005/0101951 A1 | 5/2005 | Wham |
| 2005/0107785 A1 | 5/2005 | Dycus |
| 2005/0113817 A1 | 5/2005 | Isaacson |
| 2005/0113819 A1 | 5/2005 | Wham et al. |
| 2005/0004563 A1 | 6/2005 | Racz et al. |
| 2005/0124915 A1 | 6/2005 | Eggers et al. |
| 2005/0137592 A1 | 6/2005 | Nguyen et al. |
| 2005/0149017 A1 | 7/2005 | Dycus |
| 2005/0159745 A1 | 7/2005 | Truckal |
| 2005/0165444 A1 | 7/2005 | Hart |
| 2005/0192568 A1 | 9/2005 | Truckal et al. |
| 2005/0203504 A1 | 9/2005 | Wham |
| 2005/0234447 A1 | 10/2005 | Paton et al. |
| 2005/0245918 A1 | 11/2005 | Sliwa, Jr. et al. |
| 2005/0245922 A1 | 11/2005 | Goble |
| 2006/0020265 A1 | 1/2006 | Ryan |
| 2006/0041254 A1 | 2/2006 | Francischelli et al. |
| 2006/0052777 A1 | 3/2006 | Dumbauld |
| 2006/0079678 A1 | 4/2006 | Houser |
| 2006/0079788 A1 | 4/2006 | Anderson et al. |
| 2006/0129146 A1 | 6/2006 | Dycus |
| 2006/0161190 A1 | 7/2006 | Gadberry et al. |
| 2006/0167450 A1 | 7/2006 | Johnson |
| 2006/0173453 A1 | 8/2006 | Gruh |
| 2006/0217697 A1 | 9/2006 | Lau et al. |
| 2006/0217706 A1 | 9/2006 | Lau et al. |
| 2006/0217707 A1 | 9/2006 | Daniel et al. |
| 2006/0224152 A1 | 10/2006 | Behnke et al. |
| 2006/0224158 A1 | 10/2006 | Odom |
| 2006/0247498 A1 | 11/2006 | Bonadio et al. |
| 2006/0271042 A1 | 11/2006 | Atterell et al. |
| 2007/0016185 A1 | 1/2007 | Tullis et al. |
| 2007/0043352 A1 | 2/2007 | Garrison et al. |
| 2007/0043353 A1 | 2/2007 | Dycus |
| 2007/0062017 A1 | 3/2007 | Dycus et al. |
| 2007/0088202 A1 | 4/2007 | Albrecht et al. |
| 2007/0090788 A1 | 4/2007 | Hansford et al. |
| 2007/0093800 A1 | 4/2007 | Wham et al. |
| 2007/0123847 A1 | 5/2007 | Mihori |
| 2007/0135811 A1 | 6/2007 | Hooven |
| 2007/0142833 A1 | 6/2007 | Dycus |
| 2007/0142834 A1 | 6/2007 | Dumbauld |
| 2007/0156139 A1 | 7/2007 | Schecter |
| 2007/0156140 A1 | 7/2007 | Baily |
| 2007/0167941 A1 | 7/2007 | Hamel et al. |
| 2007/0173811 A1 | 7/2007 | Couture et al. |
| 2007/0173813 A1 | 7/2007 | Odom |
| 2007/0173814 A1 | 7/2007 | Hixson et al. |
| 2007/0179499 A1 | 8/2007 | Garrison |
| 2007/0191827 A1 | 8/2007 | Lishinsky et al. |
| 2007/0191828 A1 | 8/2007 | Houser et al. |
| 2007/0203481 A1 | 8/2007 | Gregg et al. |
| 2007/0213712 A1 | 9/2007 | Buysse et al. |
| 2007/0260242 A1 | 11/2007 | Dycus et al. |
| 2007/0276363 A1 | 11/2007 | Patton et al. |
| 2007/0282195 A1 | 12/2007 | Masini et al. |
| 2007/0282320 A1 | 12/2007 | Buysse et al. |
| 2007/0282332 A1 | 12/2007 | Witt et al. |
| 2007/0287997 A1 | 12/2007 | Tolme |
| 2008/0009860 A1 | 1/2008 | Odom |
| 2008/0015563 A1 | 1/2008 | Hoey et al. |
| 2008/0015664 A1 | 1/2008 | Wham et al. |
| 2008/0030206 A1 | 2/2008 | Podhajsky et al. |
| 2008/0039831 A1 | 2/2008 | Odom et al. |
| 2008/0045947 A1 | 2/2008 | Johnson et al. |
| 2008/0058802 A1 | 3/2008 | Couture |
| 2008/0082098 A1 | 4/2008 | Tanaka et al. |
| 2008/0091189 A1 | 4/2008 | Carlton |
| 2008/0114356 A1 | 5/2008 | Johnson et al. |
| 2008/0125772 A1 | 5/2008 | Stone et al. |
| 2008/0132893 A1 | 6/2008 | D'Amelio et al. |
| 2008/0167651 A1 | 7/2008 | Tetzlaff et al. |
| 2008/0172048 A1 | 7/2008 | Martin |
| 2008/0188848 A1 | 8/2008 | Deutmeyer et al. |
| 2008/0208246 A1 | 8/2008 | Livneh |
| 2008/0215050 A1 | 9/2008 | Bakos |
| 2008/0215051 A1 | 9/2008 | Buysse et al. |
| 2008/0228179 A1 | 9/2008 | Eder et al. |
| 2008/0294222 A1 | 11/2008 | Schecter |
| 2008/0300589 A1 | 12/2008 | Paul et al. |
| 2008/0300590 A1 | 12/2008 | Horne et al. |
| 2008/0300591 A1 | 12/2008 | Darin et al. |
| 2009/0012520 A1 | 1/2009 | Hixson et al. |
| 2009/0024126 A1 | 1/2009 | Artale |
| 2009/0248007 A1 | 1/2009 | Falkenstein et al. |
| 2009/0275490 A1 | 5/2009 | Malackowski |
| 2009/0171350 A1 | 7/2009 | Dycus et al. |
| 2009/0248021 A1* | 10/2009 | McKenna .......... A61B 18/1445 606/51 |
| 2009/0248022 A1* | 10/2009 | Falkenstein ........ A61B 18/1206 606/51 |
| 2009/0270852 A1 | 10/2009 | Takashino et al. |
| 2009/0275940 A1 | 11/2009 | Malackowski et al. |
| 2012/0010614 A1 | 1/2012 | Couture |
| 2012/0059371 A1 | 3/2012 | Anderson et al. |
| 2012/0083785 A1 | 4/2012 | Roy et al. |
| 2012/0136347 A1 | 5/2012 | Brustad et al. |
| 2012/0197243 A1 | 8/2012 | Sherman et al. |
| 2012/0215220 A1 | 8/2012 | Manzo et al. |
| 2013/0018411 A1 | 1/2013 | Collings et al. |
| 2013/0046295 A1 | 2/2013 | Kerr et al. |
| 2013/0138101 A1 | 5/2013 | Kerr |
| 2013/0274743 A1 | 10/2013 | Banfalvi |
| 2013/0296843 A1 | 11/2013 | Boudreaux et al. |
| 2014/0005658 A1 | 1/2014 | Rosenbegr |
| 2014/0088583 A1 | 3/2014 | Singh |
| 2014/0214019 A1 | 7/2014 | Baxter, III et al. |
| 2016/0058492 A1 | 3/2016 | Yates et al. |

FOREIGN PATENT DOCUMENTS

| | | |
|---|---|---|
| DE | 1 2005 044918 | 2/2007 |
| EP | 315338 | 5/1989 |
| EP | 538984 | 4/1993 |
| EP | 570675 | 11/1993 |
| EP | 598202 | 5/1994 |
| EP | 0 717 967 A2 | 6/1996 |
| EP | 0 737 447 A1 | 10/1996 |
| EP | 878168 | 11/1998 |
| EP | 1054637 | 11/2000 |
| EP | 1535581 | 6/2005 |
| EP | 1545361 | 6/2005 |
| EP | 1557129 | 7/2005 |
| EP | 1634539 A1 | 3/2006 |
| EP | 1728475 | 12/2006 |
| EP | 1810628 | 7/2007 |
| EP | 1634539 B1 | 2/2008 |
| EP | 1665995 | 2/2008 |
| EP | 1946715 | 7/2008 |
| EP | 2 106 762 | 7/2009 |
| EP | 2 158 867 A1 | 8/2009 |
| EP | 2 111 812 A2 | 10/2009 |
| EP | 2 156 802 | 2/2010 |
| EP | 2 436 330 A1 | 4/2012 |
| GB | 2157175 | 10/1985 |
| GB | 2 462 453 A | 8/2008 |
| JP | 60-30946 | 2/1994 |
| JP | 83-17935 | 12/1996 |
| JP | 11-070123 | 3/1999 |
| JP | 11-070124 | 3/1999 |
| JP | 11-178833 | 7/1999 |
| JP | 2000-254135 | 9/2000 |
| JP | 2003-135481 | 5/2003 |
| JP | 2003-164463 | 6/2003 |
| JP | 2006-109945 | 4/2006 |
| JP | 2006-167403 | 6/2006 |
| JP | 2007-144201 | 6/2007 |
| JP | 2007-195980 | 8/2007 |

(56) References Cited

FOREIGN PATENT DOCUMENTS

| JP | 2007-195985 | 8/2007 |
|---|---|---|
| JP | 2008-043789 | 2/2008 |
| JP | 2008-259864 | 10/2008 |
| WO | WO93/015662 | 8/1993 |
| WO | WO97/010764 | 3/1997 |
| WO | WO99/040857 | 8/1999 |
| WO | WO01/012090 | 2/2001 |
| WO | WO04/030553 | 4/2004 |
| WO | WO04/032776 | 4/2004 |
| WO | WO04/032777 | 4/2004 |
| WO | WO2004/082495 | 9/2004 |
| WO | WO2005/004735 | 1/2005 |
| WO | WO05/053785 | 6/2005 |
| WO | WO2006/119245 | 11/2006 |
| WO | WO2006/125558 | 11/2006 |
| WO | WO07/142601 | 12/2007 |
| WO | WO08/147773 | 12/2008 |
| WO | WO 2009/065140 A1 | 5/2009 |
| WO | WO 2012/044606 A2 | 4/2012 |
| WO | WO 2012/044606 A3 | 4/2012 |
| WO | WO 2012/110996 A2 | 8/2012 |
| WO | WO 2013/030349 A1 | 3/2013 |

OTHER PUBLICATIONS

European Patent Office, Extended European Search Report for European Application No. EP 23154961.9, dated May 22, 2023, 8 pgs.
European Patent Office, Extended European Search Report for European Application No. EP 24167766.5, dated Jun. 27, 2024, 10 pgs.
"New Products" Journal of Medical Engineering and Technology, vol. 19, No. 5 (Sep./Oct. 1995), pp. 189-190.
International Preliminary Examining Authority/US, International Preliminary Report on Patentability for International Application No. PCT/US09/39046, titled "Electrosurgical System", dated Mar. 26, 2010.
International Searching Authority/US, The International Search Report and the Written Opinion for International Application No. PCT/US09/39046 titled "Electrosurgical System", mailed Jul. 27, 2009.
European Patent Office, European Search Report for European Application No. EP 10 19 2614 dated Apr. 18, 2011, titled Electrosurgical System.
European Patent Office, European Search Report for European Application No. EP 10 19 2593 dated Mar. 21, 2011, titled Electrosurgical System.
European Patent Office, Extended European Search Report for European Application No. EP 10 19 2580 dated Jul. 21, 2011.
U.S. Appl. No. 12/611,352, filed Nov. 3, 2009, titled Tissue Fusion/Welder Apparatus and Method.
U.S. Appl. No. 12/183,970 filed July 3 1, 2008, entitled Bipolar Electrosurgical Scissors.
U.S. Appl. No. 12/416,128, filed Mar. 31, 2009, entitled Electrosurgical System.
U.S. Appl. No. 12/416,668, filed Apr. 1, 2009, entitled Electrosurgical System.
U.S. Appl. No. 12/416,695, filed Apr. 1, 2009, entitled Electrosurgical System.
U.S. Appl. No. 12/416,765, filed Apr. 1, 2009, entitled Electrosurgical System.
U.S. Appl. No. 12/416,751, filed Apr. 1, 2009, entitled Electrosurgical System.
US Patent Application No. PCT/US09/39046, filed Mar. 31, 2009, entitled Electrosurgical System.
European Patent Office, The International Search Report and Written Opinion of theInternational Searching Authority for International Application No. PCT/US2011/054661. mailed Mar. 6, 2012.
International Preliminary Examining Authority, International PreliminaryReport on Patentability for International Application No. PCT/US2009/39046 dated Jan. 17, 2012.
European Patent Office, European Search Report for European Application No. EP 13 17 4814.7 dated Sep. 30, 2013, titled Electrosurgical System.
European Patent Office, Partial European Search Report for European Patent Application No. 15151398.3 dated Jun. 22, 2015.
Bertil Vallfors and Bjorn Bergdahl, Automatically controlled bipolar electrocoagulation—"COA-COMP," Neurosurg. Rev., 1984, pp. 187-190.
European Patent Office, European Search Report for European U.S. Appl. No. 12/151,288, dated Feb. 10, 2012, 8 pgs.
European Patent Office, Supplementary European Search Report for European U.S. Appl. No. 08/755,322, dated Apr. 18, 2012, 3 pgs.
European Patent Office, Supplementary European Search Report for European U.S. Appl. No. 08/755,322, dated Jun. 6, 2012, 2 pgs.
International Preliminary Examining Authority/US, International Preliminary Report on Patentability for International Application No. PCT/US2011/054661, titled "Electrosurgical Instruments and Connections Thereto," dated Apr. 2, 2013, 10 pgs.
U.S. Appl. No. 12/416,751, filed Apr. 1, 2009, entitled Electrosurgical System, now USPN 8,579,894 issued Nov. 12, 2013.
European Patent Office, Partial European Search Report for European Patent Application No. 15151398.3, dated Jun. 22, 2015, 9 pgs.
European Patent Office, European Search Report for European Patent Application No. EP 14199708.0, entitled "Electrosurgical System," dated Jul. 10, 2015, 14 pgs.
International Searching Authority/US, The International Search Report and the Written Opinion for International Application No. PCT/US2015/031452, titled "Electrosurgical Fusion Device," mailed Dec. 3, 2015, 27 pgs.
International Searching Authority/US, The International Search Report and theWritten Opinion for International Application No. PCT/US2015/066473, titled "Bipolar Electrosurgical Sealer and Divider," mailed Mar. 31, 2016, 13 pgs.
International Searching Authority/US, The International Search Report and the Written Opinion for International Application No. PCT/US15/033546, titled "Electrosurgical Seal and Dissection Systems," mailed Apr. 22, 2016, 31 pgs.
International Preliminary Examining Authority/US, International Preliminary Report on Patentability for International Application No. PCT/US2015/031452, titled "Electrosurgical System," dated Dec. 1, 2016, 21 pgs.
International Preliminary Examining Authority/US, International Preliminary Report on Patentability for International Application No. PCT/US2015/033546, titled "Electrosurgical Laparoscopic Sealer and Dissector," dated Dec. 15, 2016, 22 pgs.
International Preliminary Examining Authority/US, International Preliminary Report on Patentability for International Application No. PCT/US2015/0066473, titled "Bipolar Electrosurgical Sealer and Divider," dated Jul. 6, 2017, 10 pgs.
International Preliminary Examining Authority/US, InternationalPreliminary Report on Patentability for International Application No. PCT/US2019/049768, titled "Electrosurgical Generator Verification System," dated Mar. 18, 2021, 13 pgs.
International Preliminary Examining Authority/US, InternationalPreliminary Report on Patentability for International Application No. PCT/US2019/049807, titled "Electrosurgical Generator Control System," dated Mar. 18, 2021, 13 pgs.
International Preliminary Examining Authority/US, International PreliminaryReport on Patentability for International Application No. PCT/US2019/059909, titled "Electrosurgical System," dated May 27, 2021, 15 pgs.
European Patent Office, Extended European Search Report for European Application No. EP 21215386.0, dated May 24, 2022, 6 pgs.

* cited by examiner

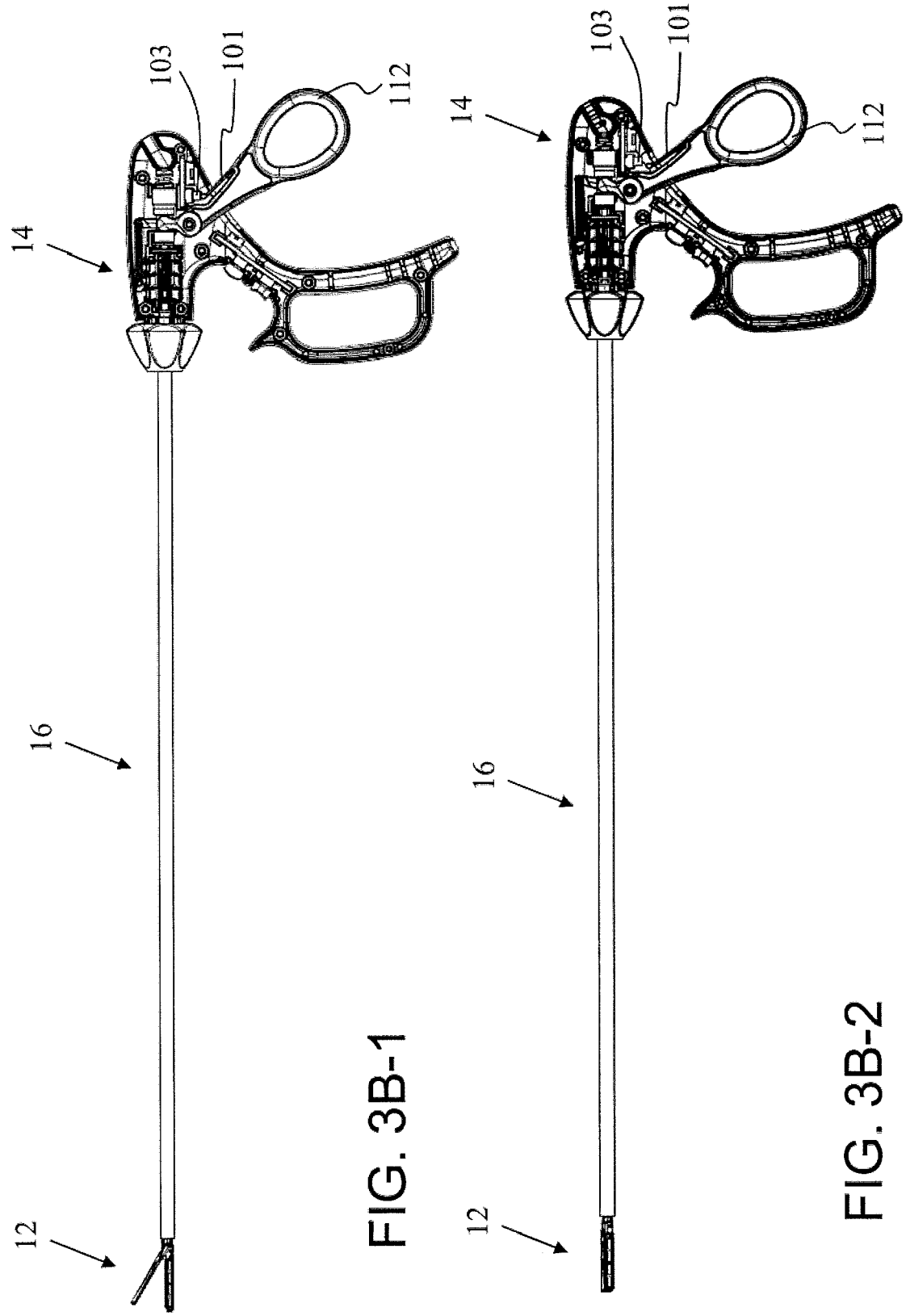

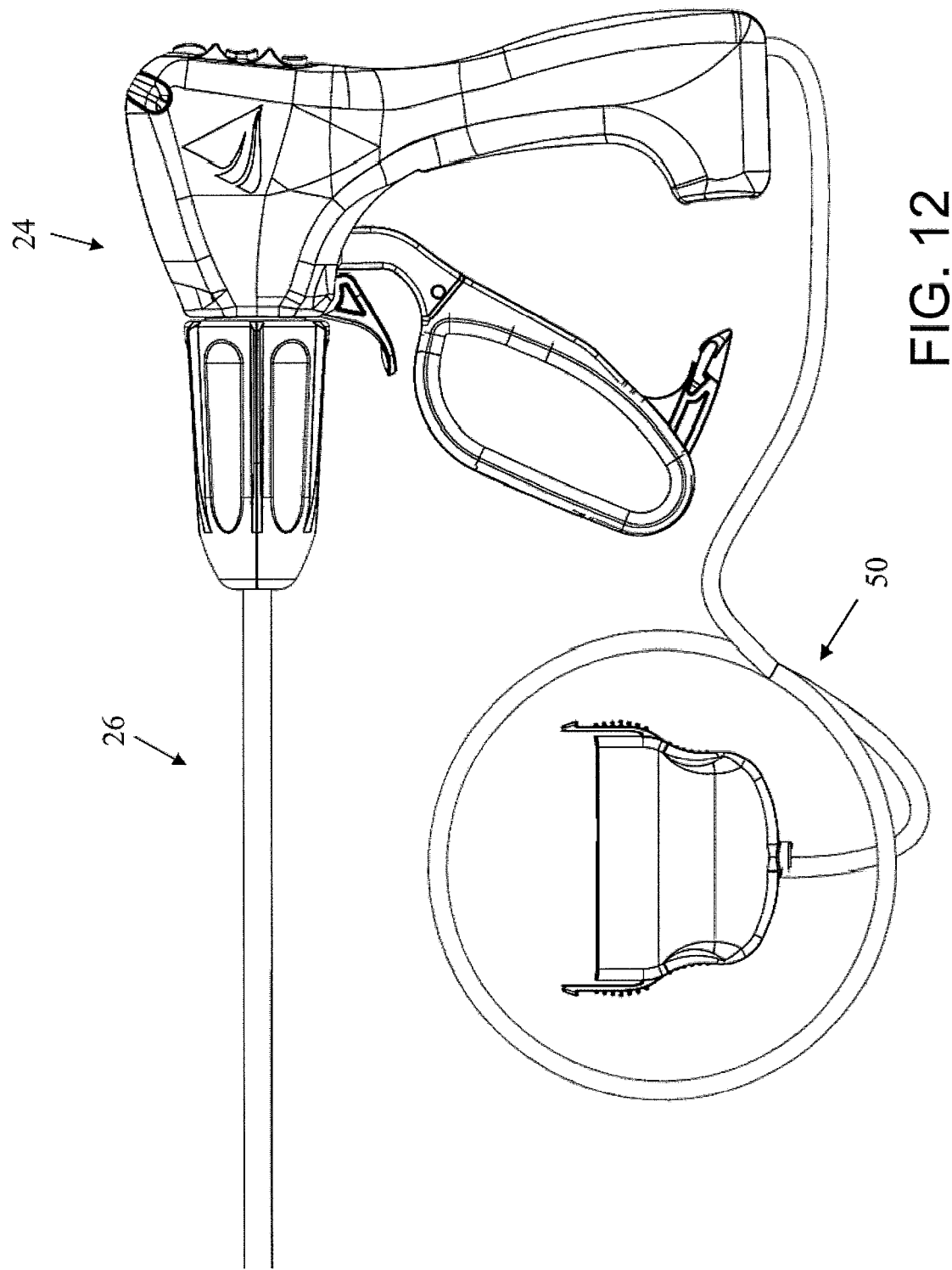

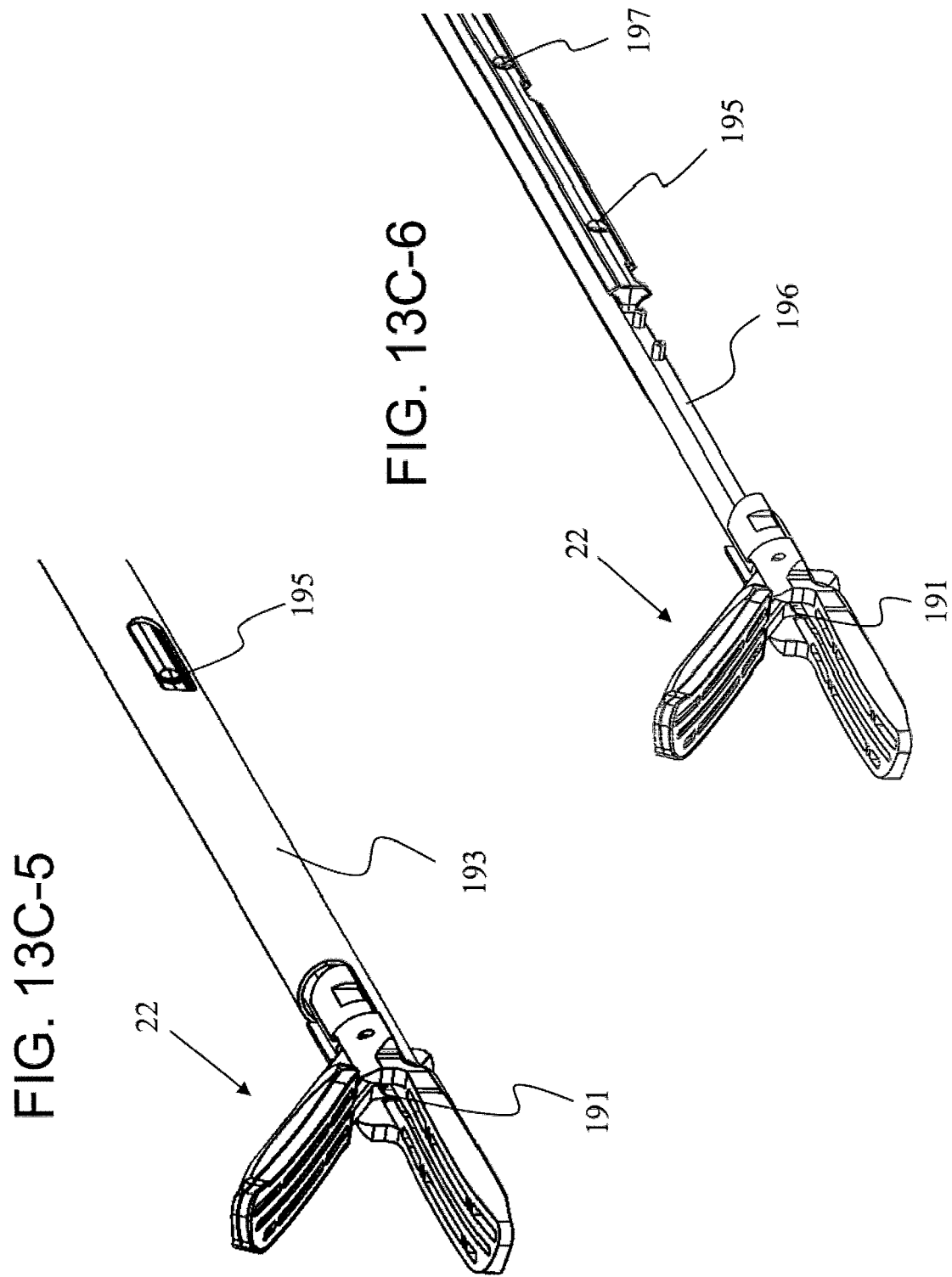

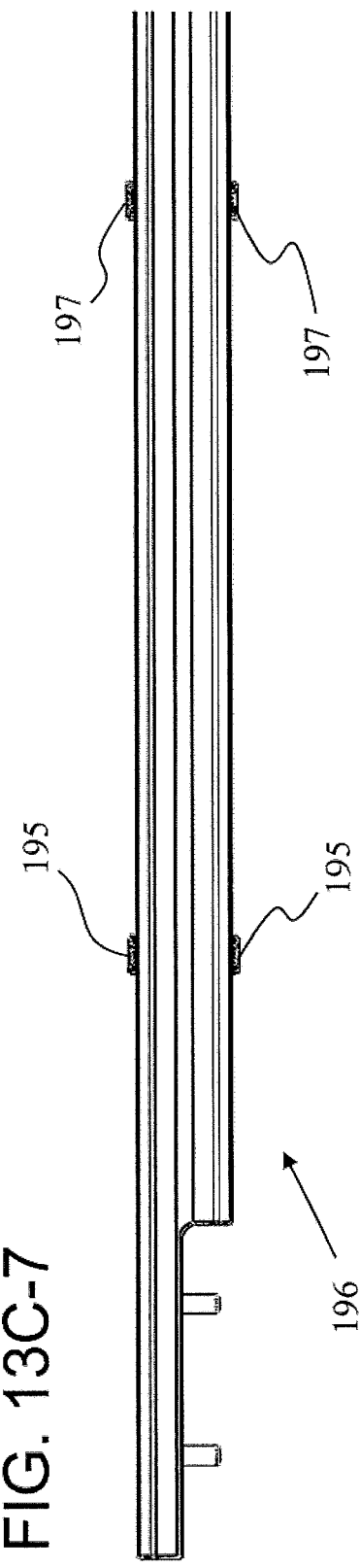
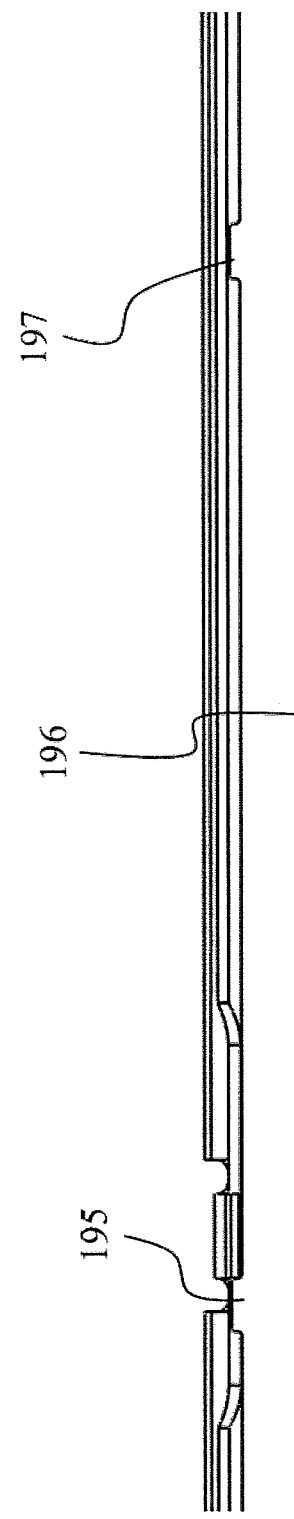
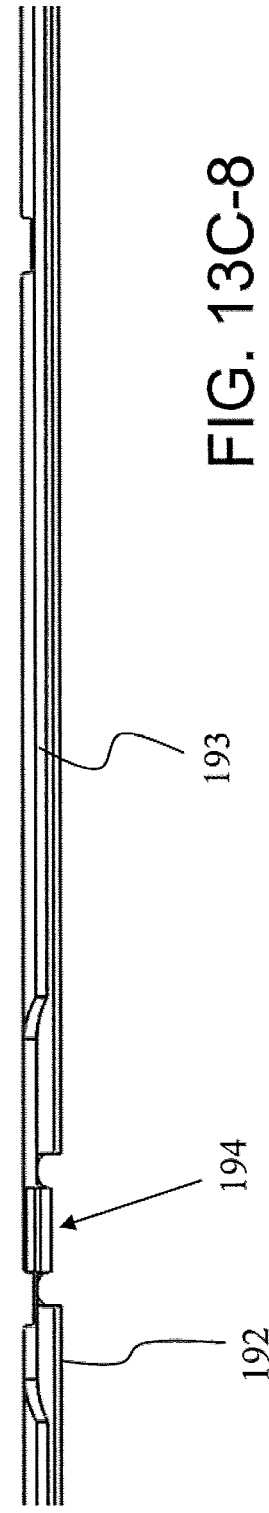
FIG. 13C-7
FIG. 13C-8

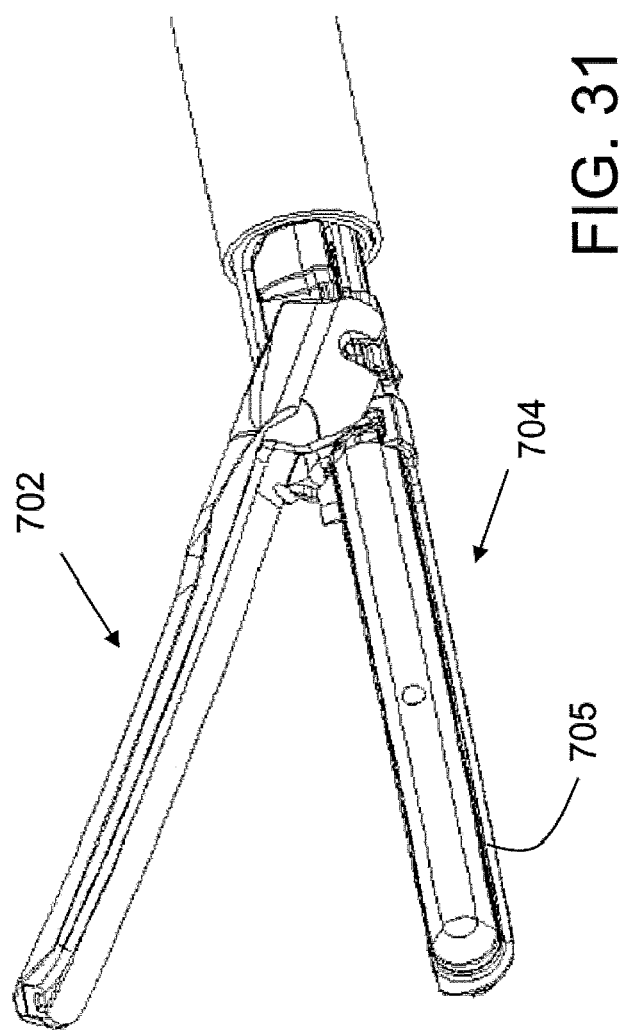

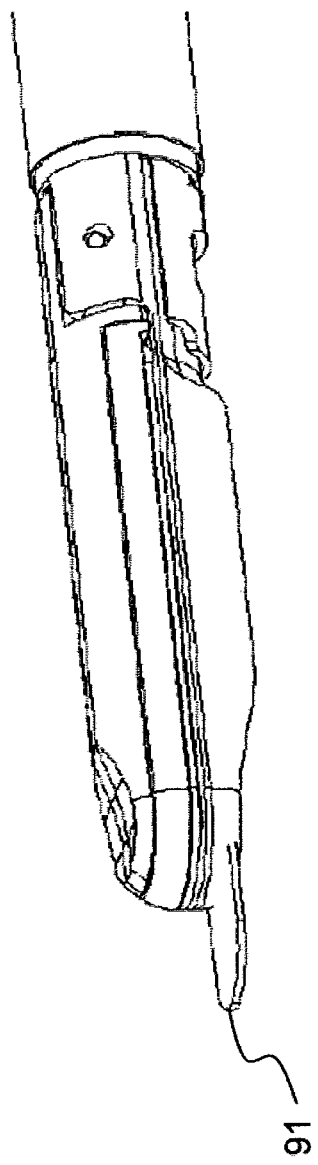
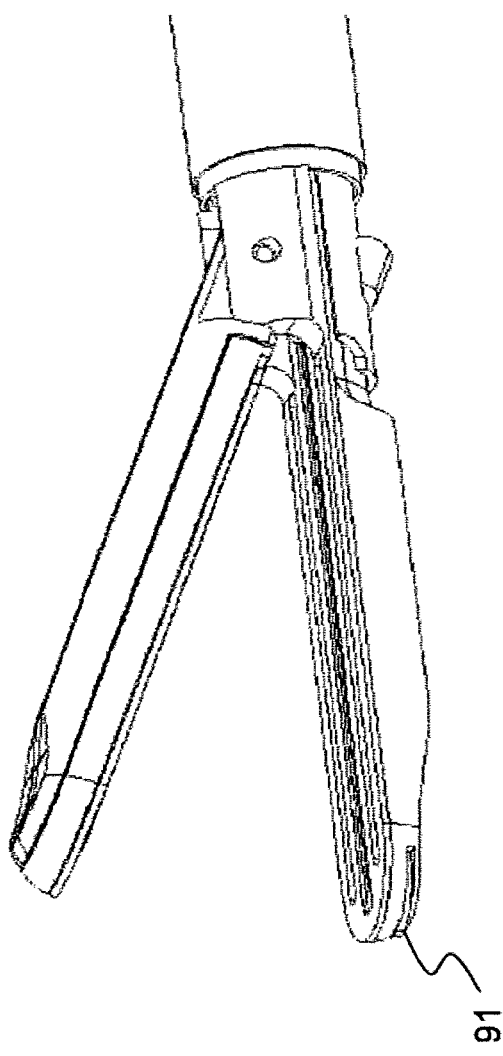
FIG. 34B
FIG. 34A

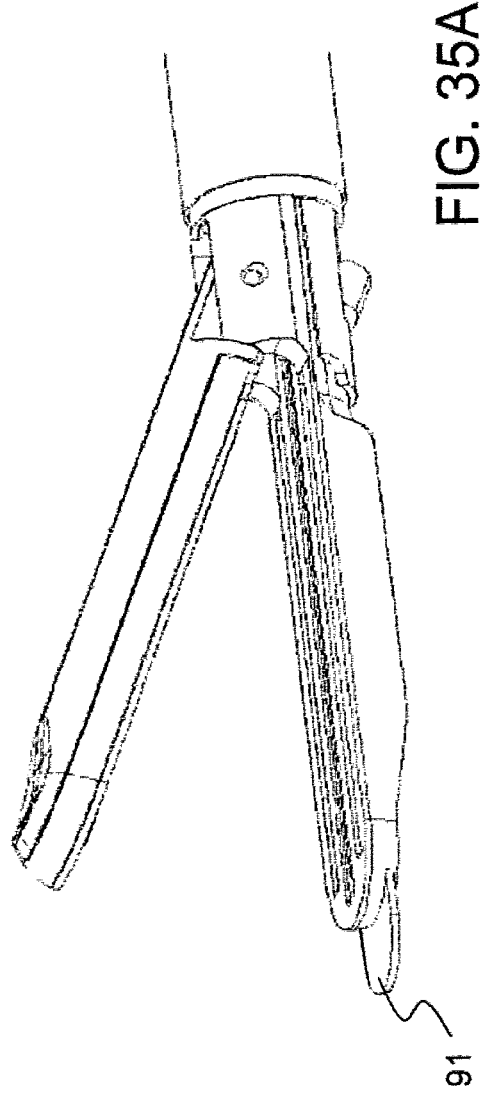
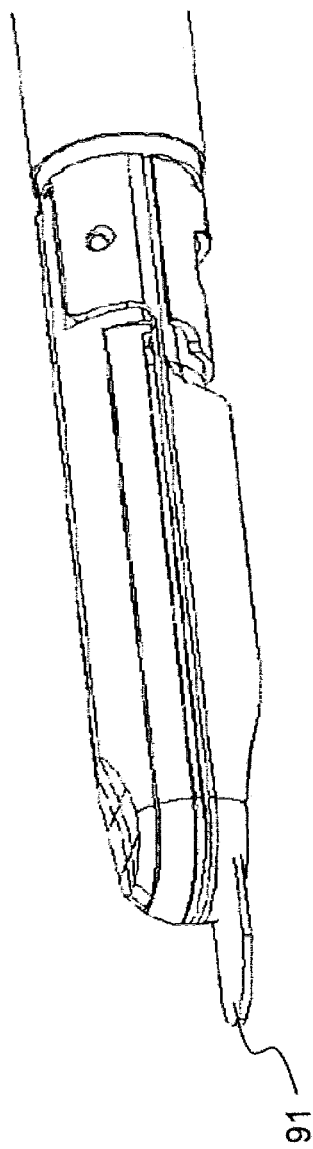
FIG. 35A
FIG. 35B

|  | A | B | C | D | E | F (Grounding Pad) |
|---|---|---|---|---|---|---|
| Bipolar | +, -, 0 | +, -, 0 | +, -, 0 | +, -, 0 | +, -, 0 |  |
| Bipolar/ Monopolar | +, -, 0 | +, -, 0 | +, -, 0 | +, -, 0 | +, -, 0 | +, 0 |
|  |  | + = Return | - = Active | 0 = Neutral |  |  |

FIG. 38

ELECTROSURGICAL INSTRUMENTS AND CONNECTIONS THERETO

CROSS-REFERENCE TO RELATED APPLICATIONS

This application is a continuation of U.S. application Ser. No. 17/135,520, filed Dec. 28, 2020, which is a continuation of U.S. application Ser. No. 15/936,914, filed Mar. 27, 2018, now U.S. Pat. No. 10,874,452, which is a continuation of U.S. application Ser. No. 15/136,652, filed Apr. 22, 2016, now U.S. Pat. No. 9,962,222, which is a continuation of U.S. Application No. 13/366,487, filed Feb. 6, 2012, now U.S. Pat. No. 9,320,563, which is a continuation of International Application No. PCT/US2011/054661, filed on Oct. 3, 2011, which claims the benefit of U.S. Provisional Application No. 61/389,012, filed on Oct. 1, 2010, the entire disclosures of which are incorporated by reference as if set forth in full herein.

BACKGROUND

The present application relates generally to electrosurgical systems and methods and more particularly to electrosurgical instruments and connections between the instruments and electrosurgical units.

Surgical procedures often involve cutting and connecting bodily tissue including organic materials, musculature, connective tissue and vascular conduits. For centuries, sharpened blades and sutures have been mainstays of cutting and reconnecting procedures. As bodily tissue, especially relatively highly vascularized tissue is cut during a surgical procedure, it tends to bleed. Thus, medical practitioners such as surgeons have long sought surgical instruments and methods that slow or reduce bleeding during surgical procedures.

More recently, electrosurgical instruments have become available that use electrical energy to perform certain surgical tasks. Typically, electrosurgical instruments are hand instruments such as graspers, scissors, tweezers, blades, needles, and other hand instruments that include one or more electrodes that are configured to be supplied with electrical energy from an electrosurgical unit including a power supply. The electrical energy can be used to coagulate, fuse, or cut tissue to which it is applied. Advantageously, unlike typical mechanical blade procedures, application of electrical energy to tissue tends to stop bleeding of the tissue.

Electrosurgical instruments typically fall within two classifications: monopolar and bipolar. In monopolar instruments, electrical energy of a certain polarity is supplied to one or more electrodes on the instrument. A separate return electrode is electrically coupled to a patient. Monopolar electrosurgical instruments can be useful in certain procedures, but can include a risk of certain types of patient injuries such as electrical burns often at least partially attributable to functioning of the return electrode. In bipolar electrosurgical instruments, one or more electrodes is electrically coupled to a source of electrical energy of a first polarity and one or more other electrodes is electrically coupled to a source of electrical energy of a second polarity opposite the first polarity. Thus, bipolar electrosurgical instruments, which operate without separate return electrodes, can deliver electrical signals to a focused tissue area with a reduced risk of patient injuries.

Even with the relatively focused surgical effects of bipolar electrosurgical instruments, however, surgical outcomes are often highly dependent on surgeon skill. For example, thermal tissue damage and necrosis can occur in instances where electrical energy is delivered for a relatively long duration or where a relatively high-powered electrical signal is delivered even for a short duration. The rate at which a tissue will achieve the desired coagulation or cutting effect upon the application of electrical energy varies based on the tissue type and can also vary based on pressure applied to the tissue by an electrosurgical instrument. However, even for a highly experienced surgeon, it can be difficult for a surgeon to assess how quickly a mass of combined tissue types grasped in an electrosurgical instrument will be fused a desirable amount.

Attempts have been made to reduce the risk of tissue damage during electrosurgical procedures. For example, previous electrosurgical systems have included generators that monitor an ohmic resistance or tissue temperature during the electrosurgical procedure, and terminated electrical energy once a predetermined point was reached. However, these systems have had shortcomings in that they have not provided consistent results at determining tissue coagulation, fusion, or cutting endpoints for varied tissue types or combined tissue masses. These systems can also fail to provide consistent electrosurgical results among use of different instruments having different instrument and electrode geometries. Typically, even where the change is a relatively minor upgrade to instrument geometry during a product's lifespan, the electrosurgical unit must be recalibrated for each instrument type to be used, a costly, time consuming procedure which can undesirably remove an electrosurgical unit from service.

SUMMARY

Generally, electrosurgical instrument, units and connections between them are provided. Various embodiments described with various instruments, units and/or connections can be interchangeable or applicable as provided below. In one embodiment, an electrosurgical instrument is provided and comprises a first jaw and a second jaw opposing the first jaw and is coupled to the first jaw to capture tissue between the first and second jaws. A first electrode is connected to the first jaw and extendable from a first position within the first jaw to a second position outside the first jaw. The first electrode is electrically connected to a stationary electrode positioned on the first or the second jaw.

In another embodiment, an electrosurgical unit comprising a radio frequency (RF) amplifier is provided. The RF amplifier is configured to supply RF energy to coagulate and cut tissue and the RF amplifier supplies RF energy to tissue that is not sufficient to completely coagulate tissue prior to the supplying of RF energy to cut tissue.

In another embodiment, an electrosurgical instrument is provided and comprises a first jaw and a second jaw opposing the first jaws and coupled to the first jaw to capture tissue between the first and second jaws. First, second, third and fourth electrodes are disposed on the first jaw and a fifth electrode is disposed on the second jaw.

In yet another embodiment, an electrosurgical instrument is provided and comprises a first jaw and a second jaw opposing the first jaws and coupled to the first jaw to capture tissue between the first and second jaws. A first electrode is connected to the first jaw and a movable cutter is connected to the first or second jaw. The instrument also comprises an actuator having a stationary handle and a movable trigger connected to at least one of the first and second jaws to move the jaws between spaced and proximate positions, an elongate shaft connected to the actuator and the first or second jaws, and a blade trigger connected to a blade shaft connected to the movable cutter disposed within the elongate shaft and movable along a longitudinal axis. The instrument also comprises a first stop limiting distal travel of the blade shaft along the longitudinal axis.

In one embodiment, an electrosurgical instrument comprises a first jaw and a second jaw opposing the first jaws and coupled to the first jaw to capture tissue between the first and second jaws. A first electrode is connected to the first jaw and an actuator comprises a rotatable elongate shaft connected to the actuator and the first or second jaws; at least one conductive connection surrounds a portion of the rotatable elongate shaft within the actuator; and at least one stationary contact is disposed within the actuator and electrically connectable to the at least one conductive connection, the at least one conductive ring electrically connected to the first electrode.

BRIEF DESCRIPTION OF THE DRAWINGS

The present inventions may be understood by reference to the following description, taken in connection with the accompanying drawings in which the reference numerals designate like parts throughout the figures thereof.

FIG. 3A-1 is a side view of an interior of an actuator of an electrosurgical instrument in accordance with various embodiments of the invention.

FIG. 3A-2 is a side view of an interior of an actuator of an electrosurgical instrument in accordance with various embodiments of the invention with some components removed to facilitate viewing.

FIG. 3A-3 is a perspective view of conductive connectors of an electrosurgical instrument in accordance with various embodiments of the invention.

FIG. 3A-4 is a perspective view of an interior of an actuator of an electrosurgical instrument in accordance with various embodiments of the invention.

FIG. 3A-5 is a perspective view of a conductive ring of an electrosurgical instrument in accordance with various embodiments of the invention.

FIG. 3A-6 is a perspective view of an interior of an actuator of an electrosurgical instrument in accordance with various embodiments of the invention.

FIG. 3A-7 is a perspective view of a contact brush of an electrosurgical instrument in accordance with various embodiments of the invention.

FIG. 3A-8 is a perspective view of a rotary connector with an exemplary single wire in accordance with various embodiments of the invention.

FIGS. 3B-1 to 3B-2 illustrate side views of an interior of an actuator of an electrosurgical instrument at different stages of actuation in accordance with various embodiments of the invention.

FIG. 5 is a focused view of one of the jaws of an electrosurgical instrument in accordance with various embodiments of the invention.

FIG. 6 is a side view of jaws of an electrosurgical instrument in accordance with various embodiments of the invention.

FIG. 7 is a perspective view of jaws of an electrosurgical instrument in accordance with various embodiments of the invention.

FIG. 8 is a focused view of one of the jaws of an electrosurgical instrument in accordance with various embodiments of the invention.

FIG. 12 is a side view of an electrosurgical instrument with portions of an associated coupler to connect to an electrosurgical unit in accordance with various embodiments of the invention.

FIGS. 13B-1 to 13B-3 illustrate side views of an interior of an actuator of an electrosurgical instrument at different stages of actuation in accordance with various embodiments of the invention.

FIG. 13C-1 illustrates a perspective view of jaws and a shaft of an electrosurgical instrument in accordance with various embodiments of the invention with a portion of the shaft removed (not shown).

FIG. 13C-2 illustrates a cross-sectional view of a cover tube of an electrosurgical instrument in accordance with various embodiments of the invention.

FIG. 13C-3 illustrates a perspective view of a cover tube of an electrosurgical instrument in accordance with various embodiments of the invention.

FIG. 13C-4 illustrates a side view of a cover tube of an electrosurgical instrument in accordance with various embodiments of the invention.

FIG. 13C-5 illustrates a perspective view of jaws and a shaft of an electrosurgical instrument in accordance with various embodiments of the invention with a portion of the shaft removed (not shown).

FIG. 13C-6 illustrates a perspective view of jaws and a blade shaft of an electrosurgical instrument in accordance with various embodiments of the invention.

FIG. 13C-7 illustrates a side view of a blade shaft of an electrosurgical instrument in accordance with various embodiments of the invention.

FIG. 13C-8 illustrates a cross-sectional view of a shaft of an electrosurgical instrument in accordance with various embodiments of the invention.

FIG. 31 is a perspective view of jaws of an electrosurgical instrument in accordance with various embodiments of the invention.

FIGS. 34A-B are perspective views of jaws of an electrosurgical instrument in accordance with various embodiments of the invention.

FIGS. 35A-B are perspective views of jaws of an electrosurgical instrument in accordance with various embodiments of the invention.

FIG. 38 is an exemplary chart illustrating electrode configurations in accordance with various embodiments of the invention.

FIG. 39A-1 is a perspective view of a monopolar pad and an electrosurgical unit in accordance with various embodiments of the invention.

FIG. 39A-2 is a close-up perspective view of a monopolar port of an electrosurgical unit in accordance with various embodiments of the invention.

DETAILED DESCRIPTION

Figure 1:
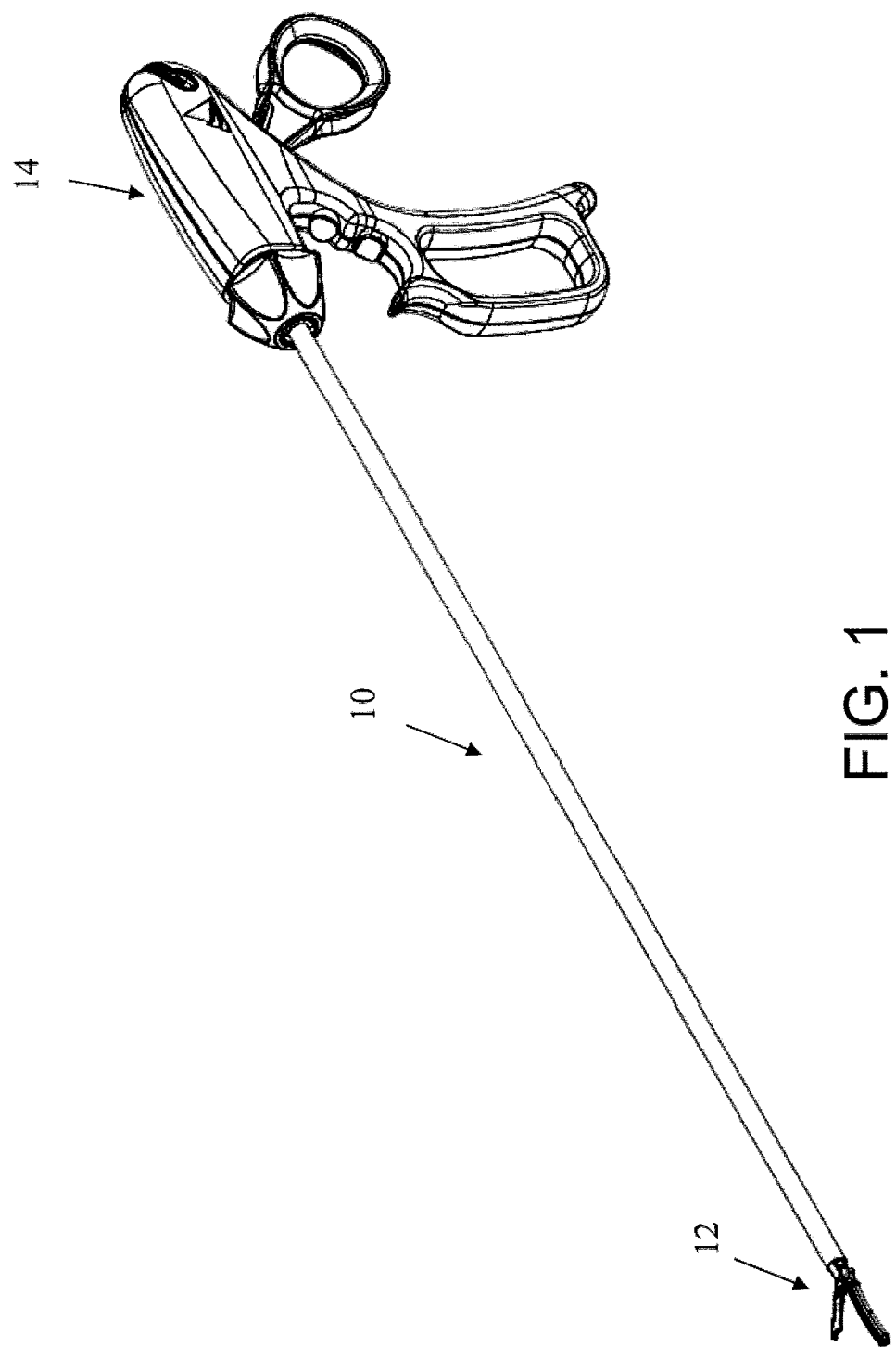
FIG. 1 is a perspective view of an embodiment of an electrosurgical instrument in accordance with various embodiments of the invention.
Figure 2A:
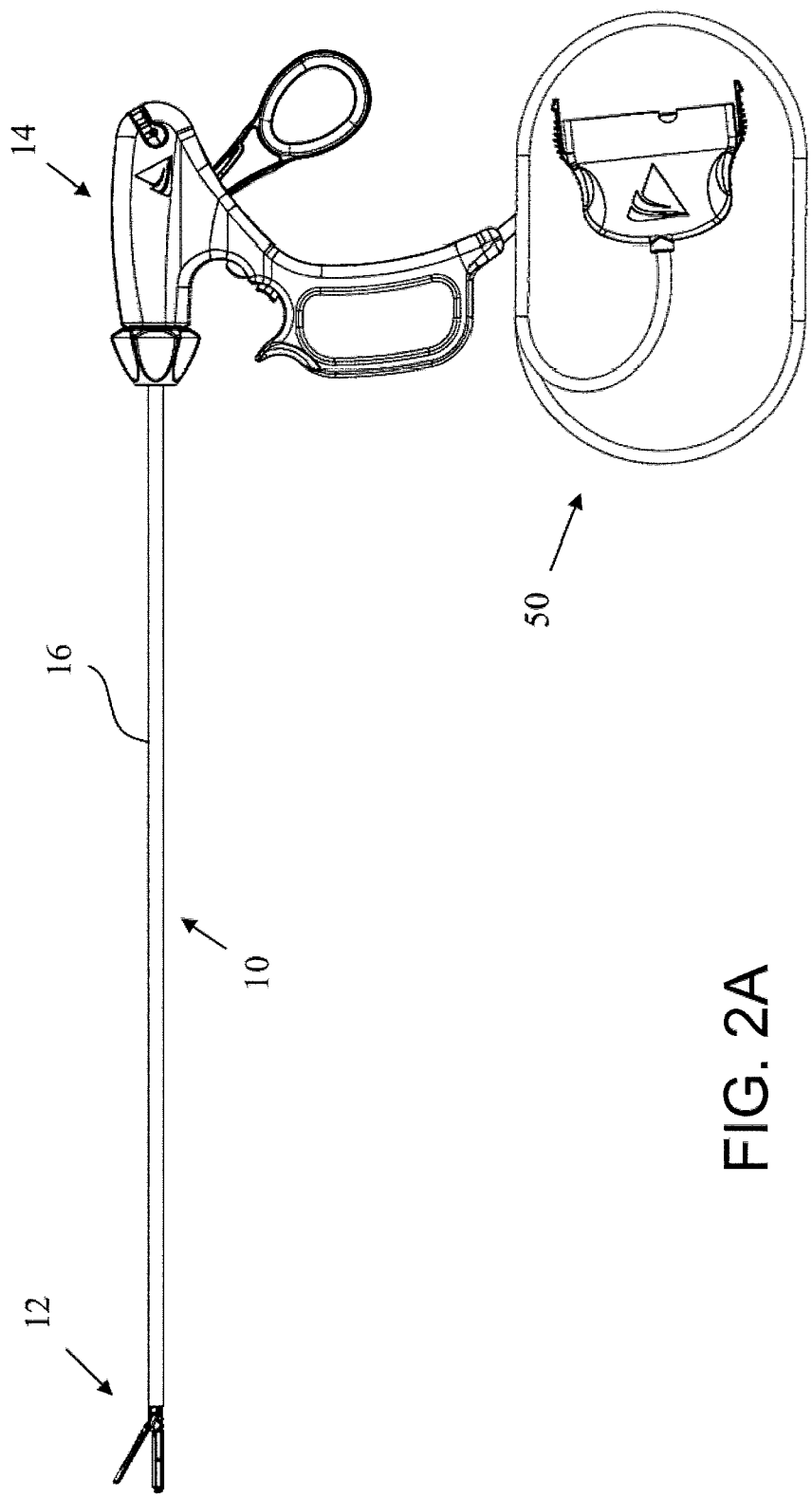
FIG. 2A is a side view of an electrosurgical instrument with an associated coupler to connect to an electrosurgical unit in accordance with various embodiments of the invention.
Figure 2B:
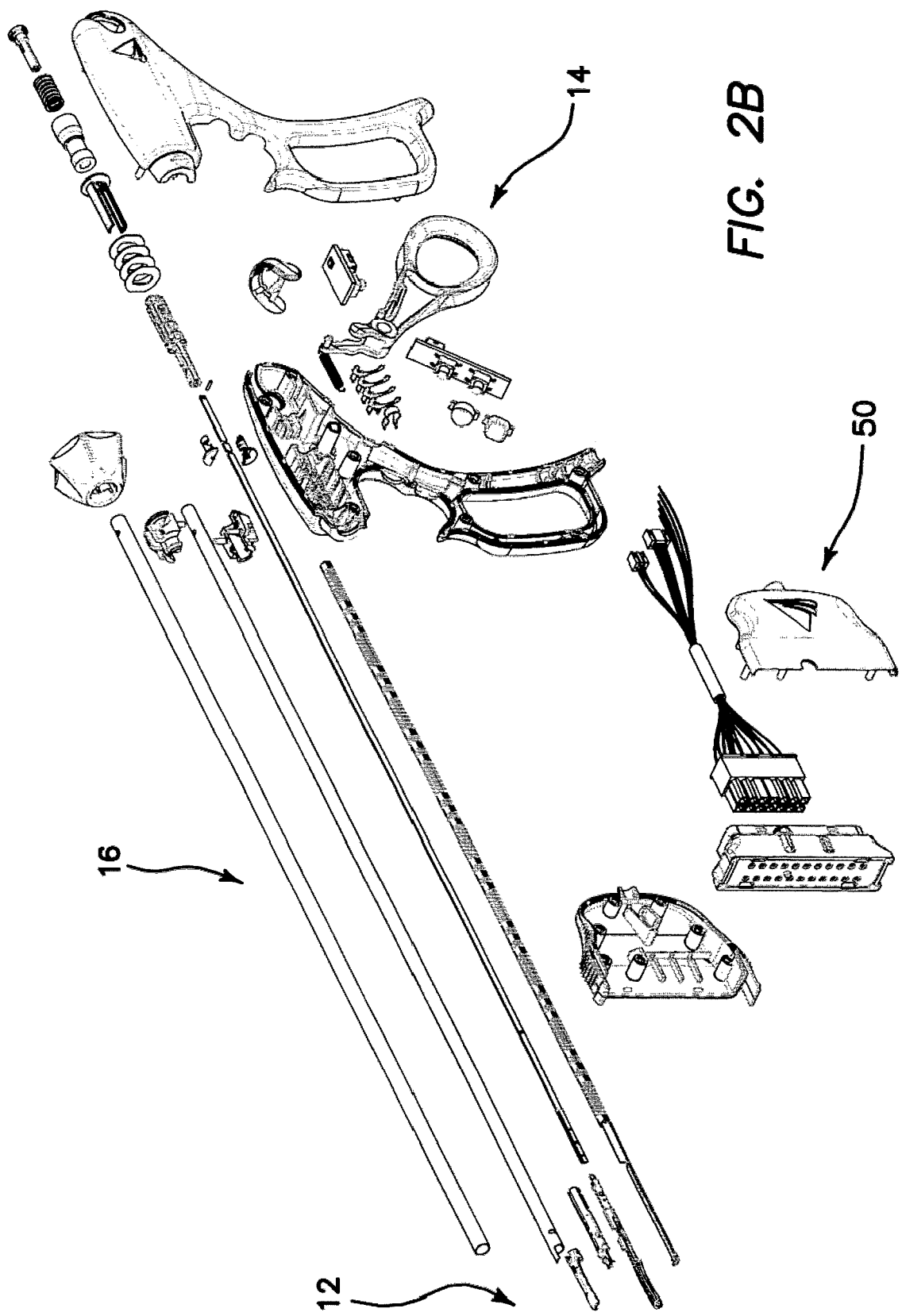
FIG. 2B is a dissembled view of an electrosurgical instrument with an associated coupler to connect to an electrosurgical unit in accordance with various embodiments of the invention.
Figures 1, 3A:
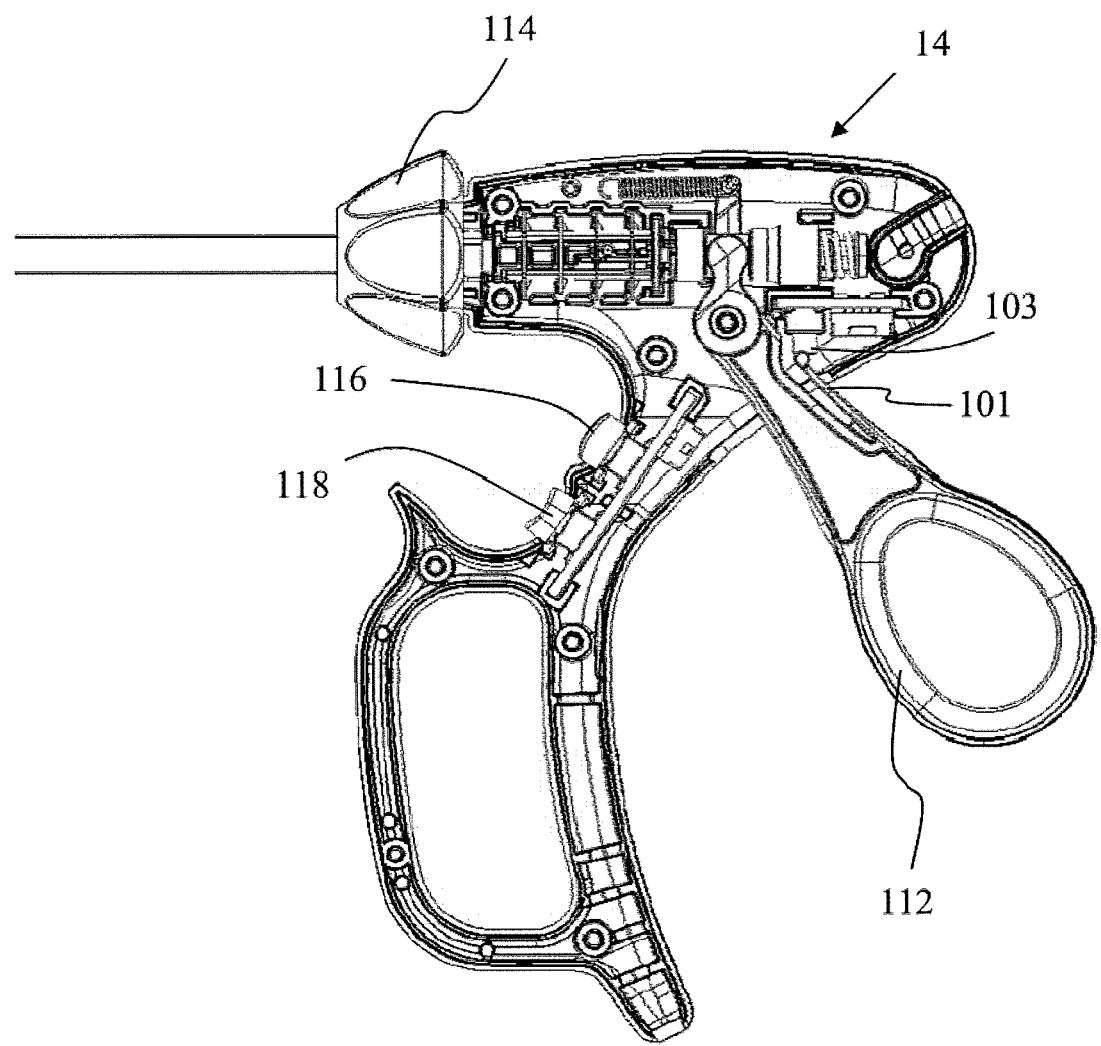
Figures 2, 3A:
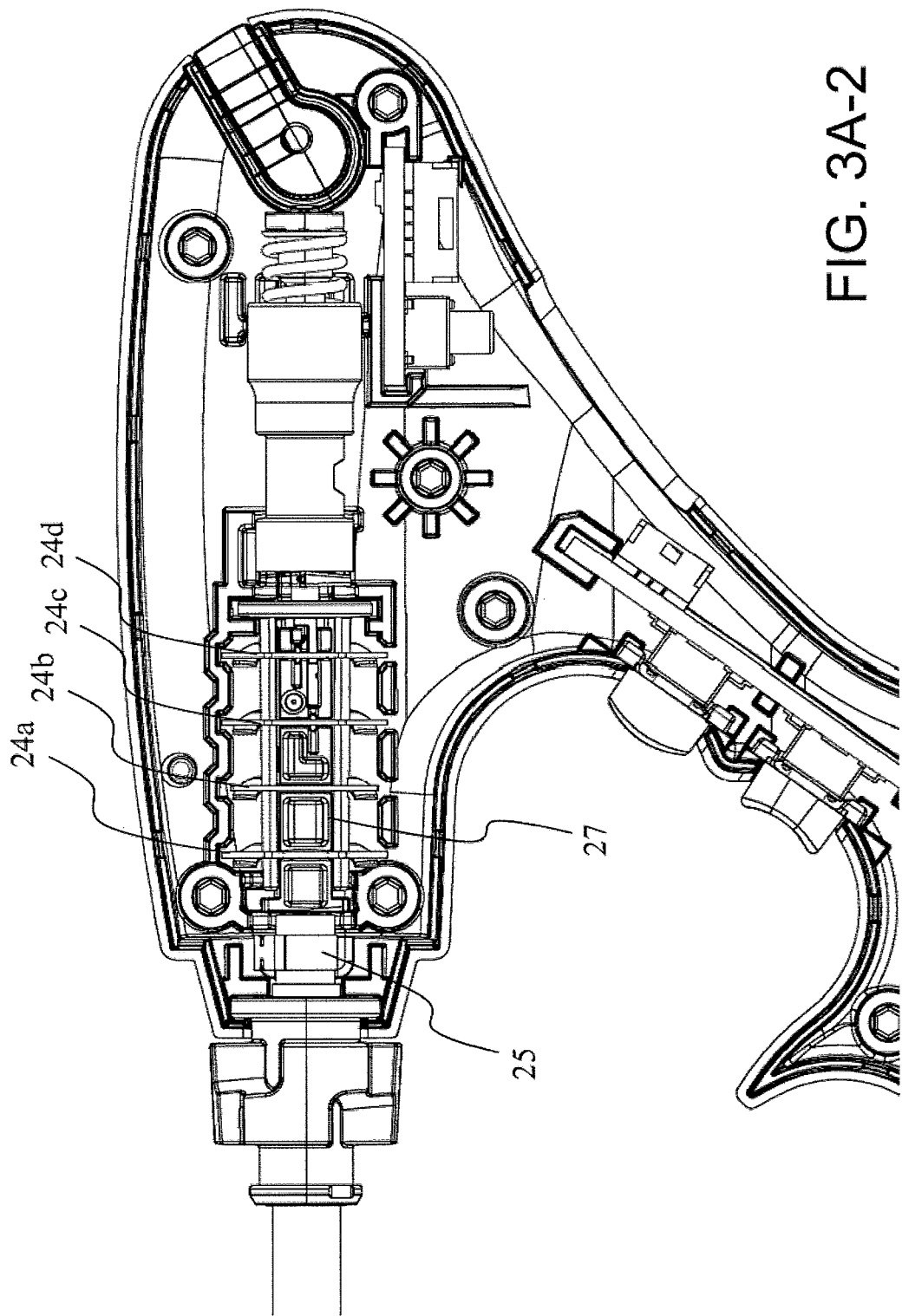
Figures 3, 3A:
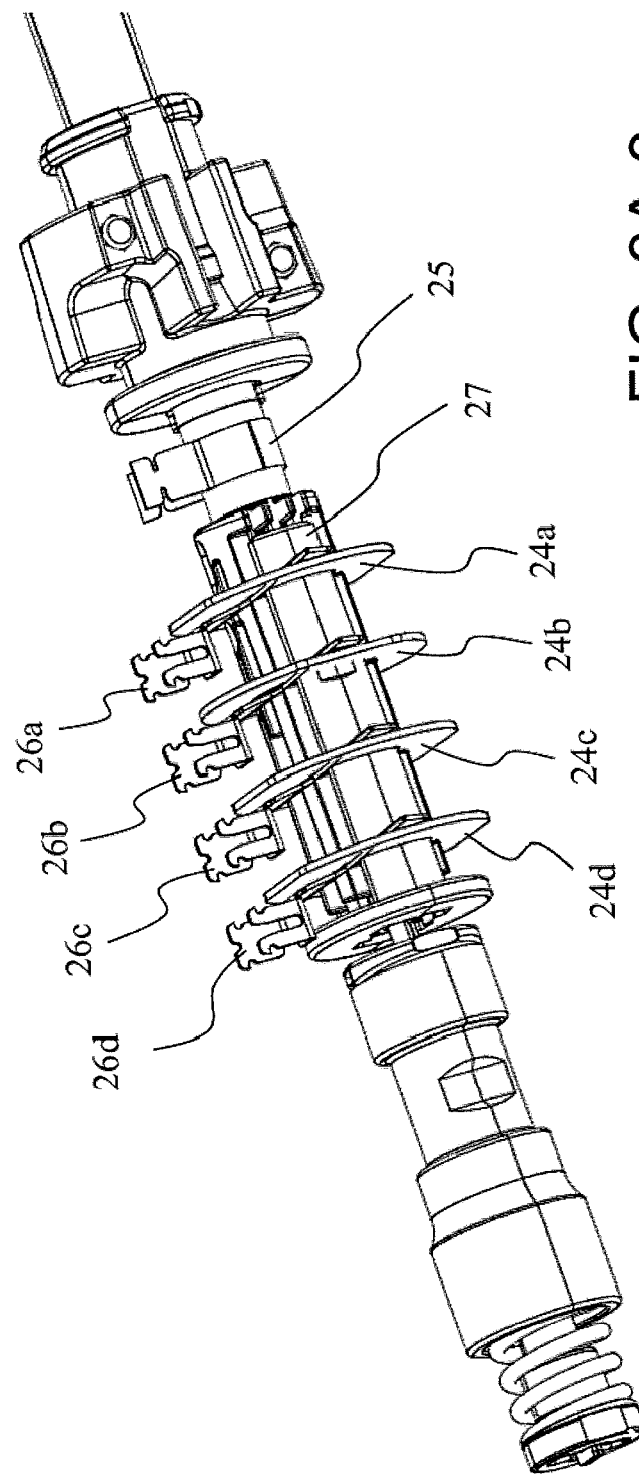
Figures 3, 3A, 4, 5:
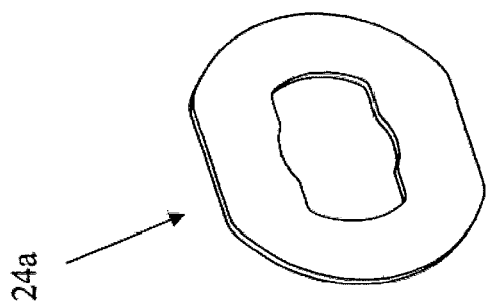
Figures 3, 3A, 4:
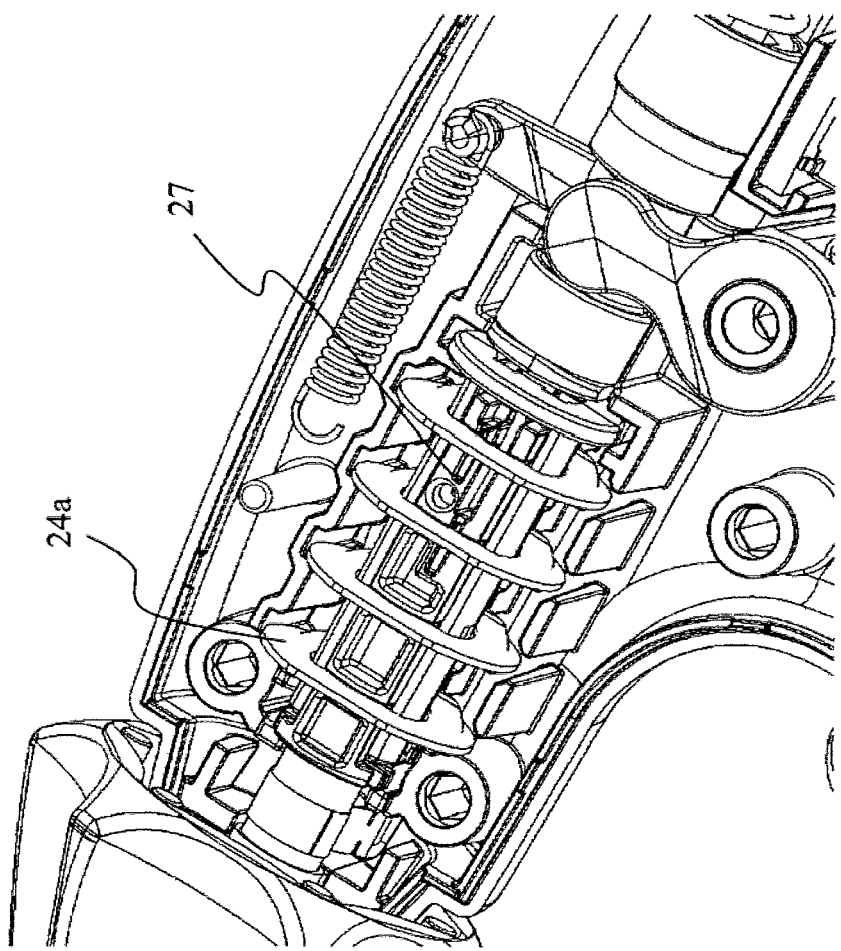
Figures 3, 3A, 4, 5, 6, 7:
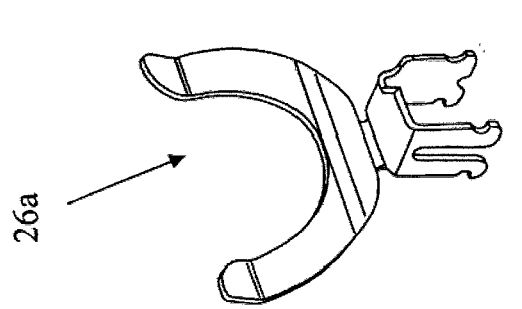
Figures 3, 3A, 4, 5, 6:
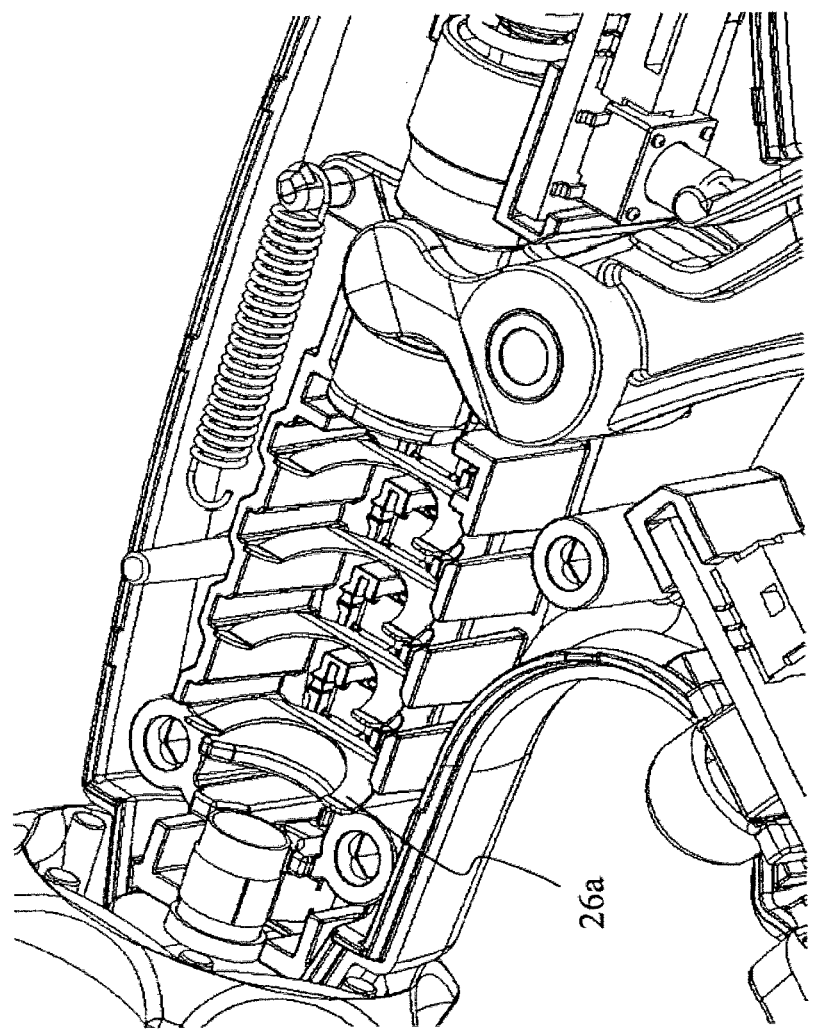
Figures 3, 3A, 4, 5, 6, 7, 8:
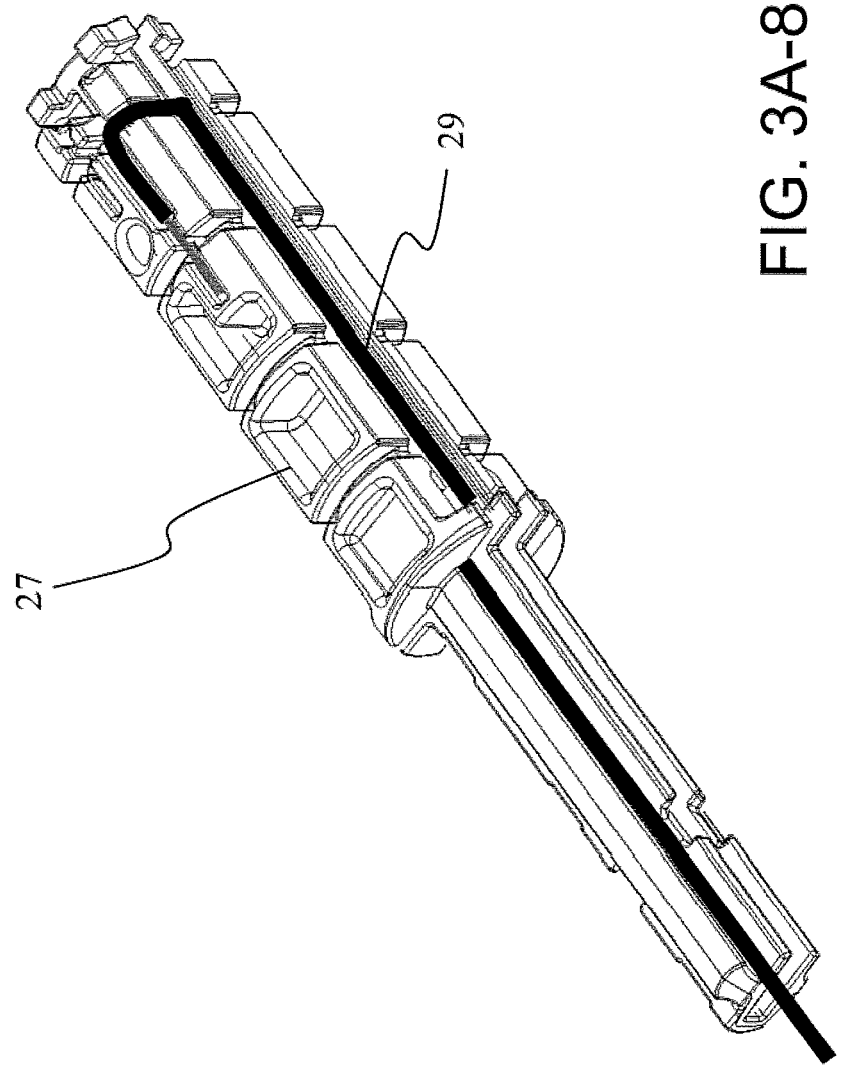
Figure 4C:
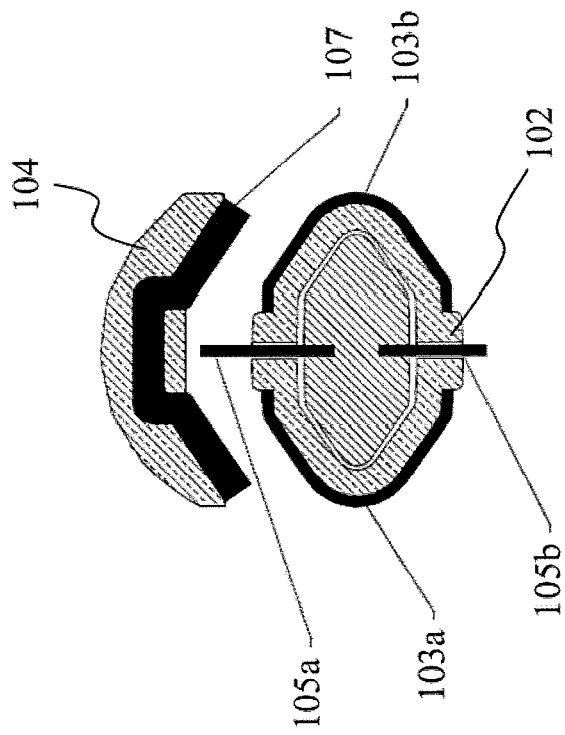
FIG. 4C illustrates a cross-sectional view of jaws of an electrosurgical instrument in accordance with various embodiments of the invention.
Figure 4A:
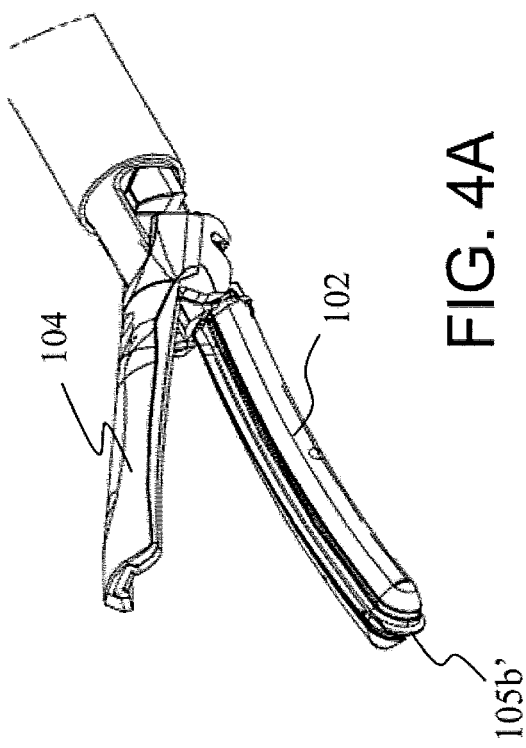
FIG. 4A illustrates a perspective view of jaws of an electrosurgical instrument in accordance with various embodiments of the invention.
Figure 4B:
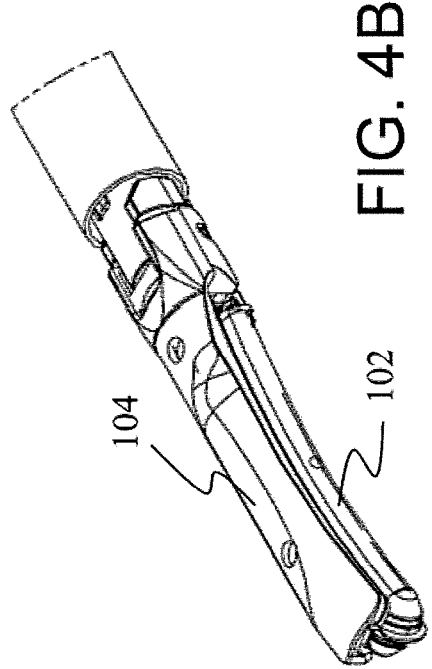
FIG. 4B illustrates a perspective view of jaws of an electrosurgical instrument in accordance with various embodiments of the invention.
Figure 5:
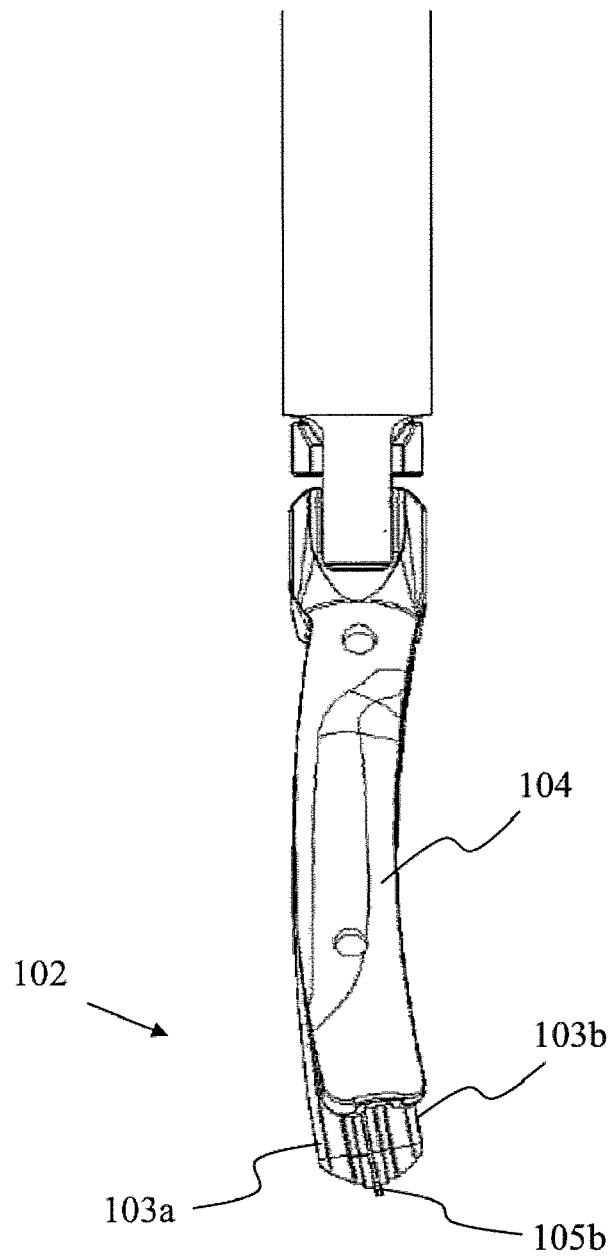
Figure 6:
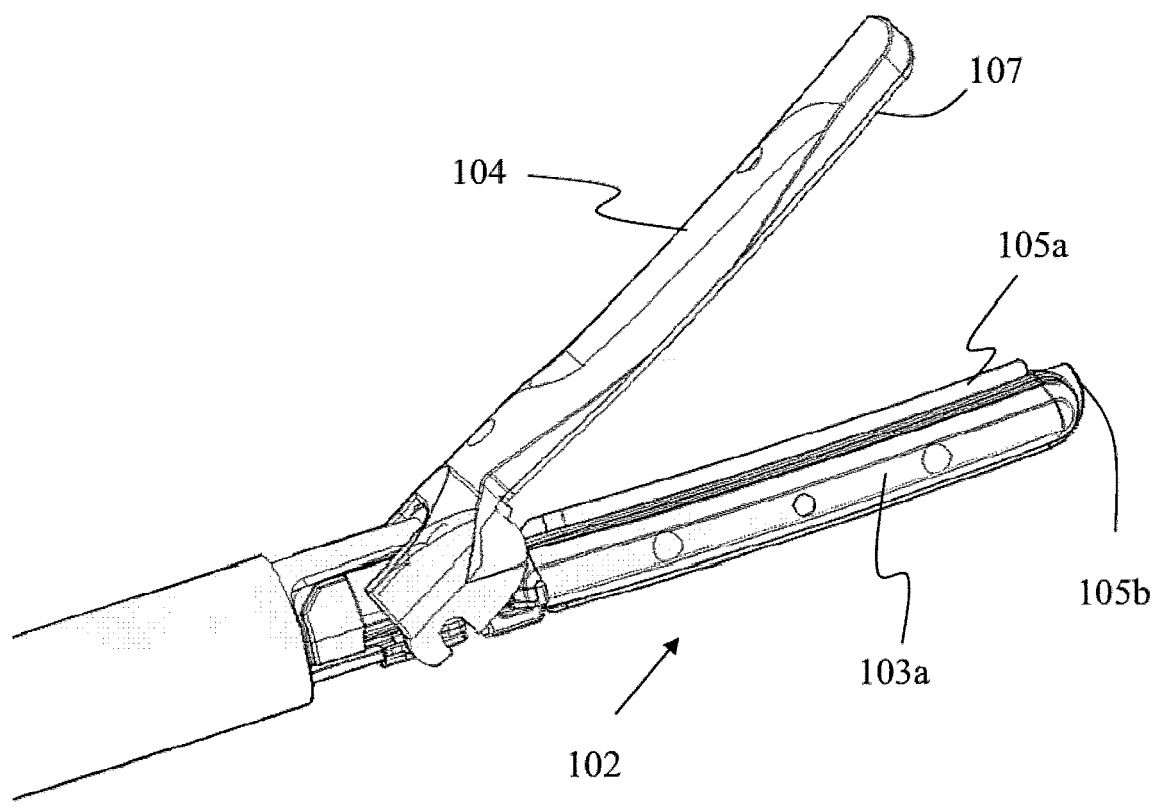
Figure 7:
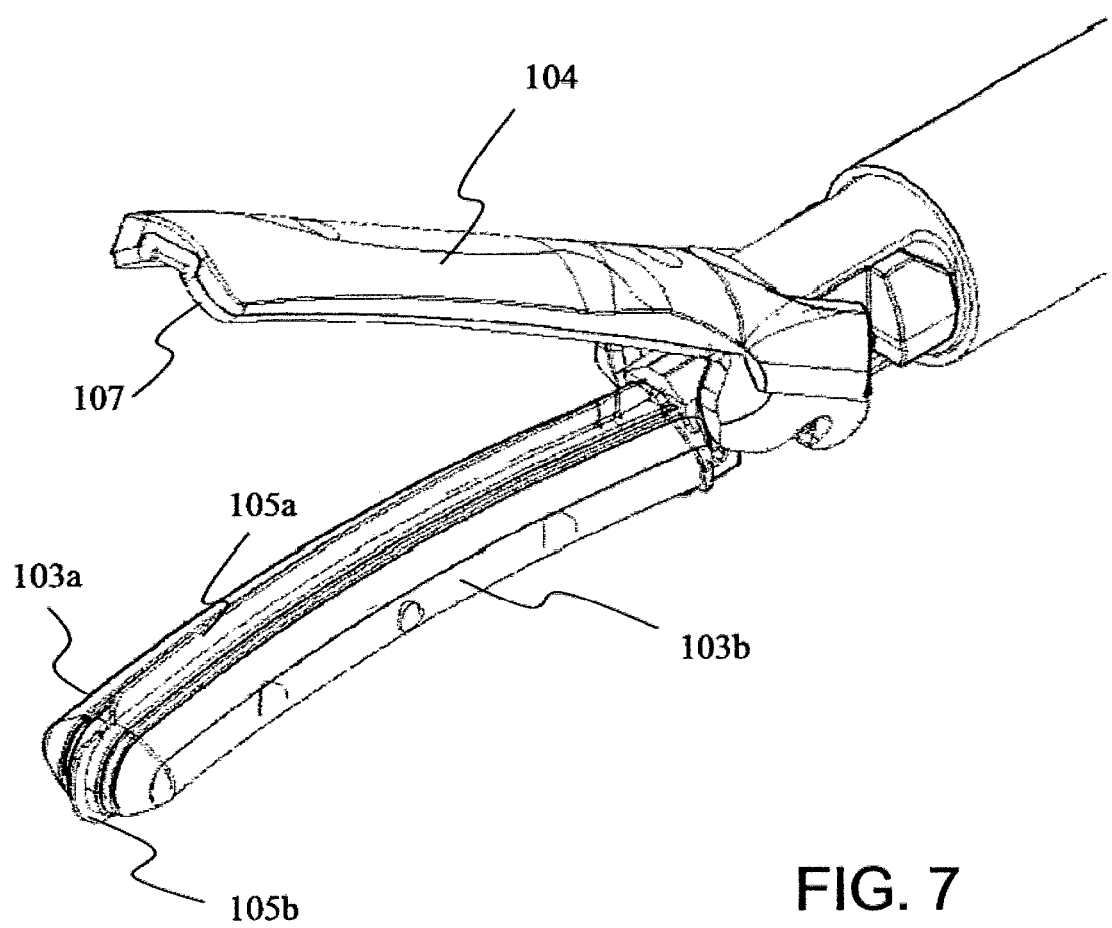
Figure 8:
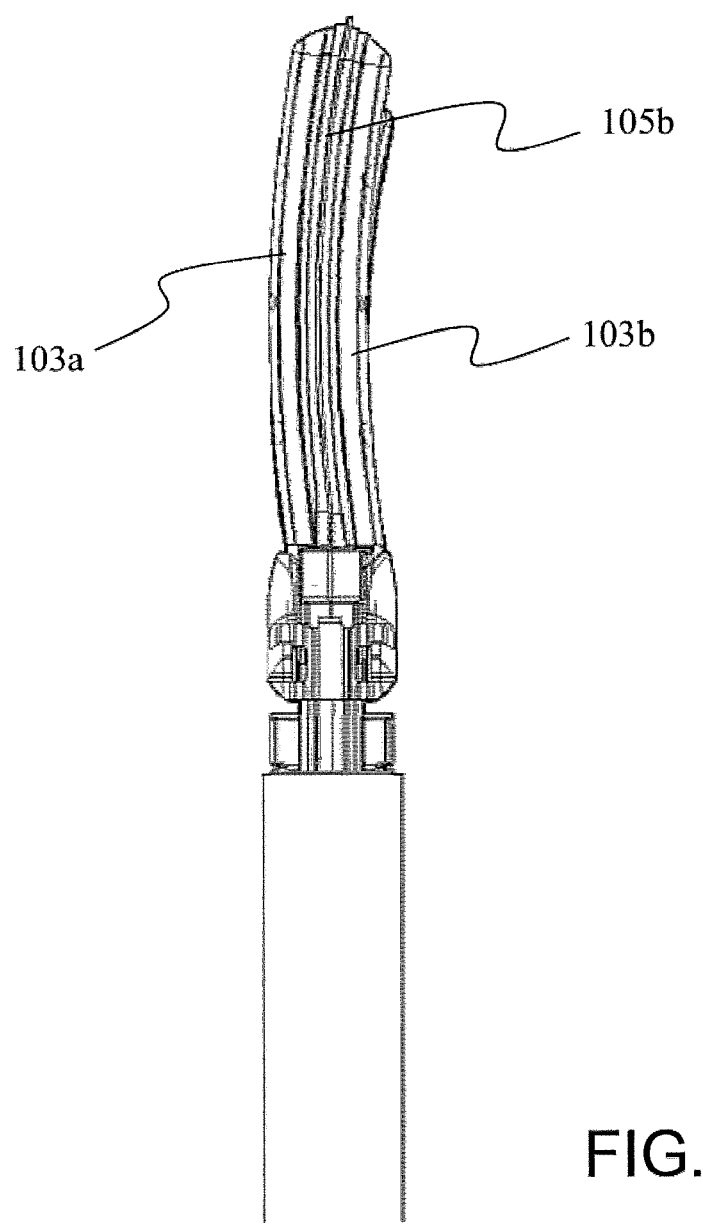
Figure 9:
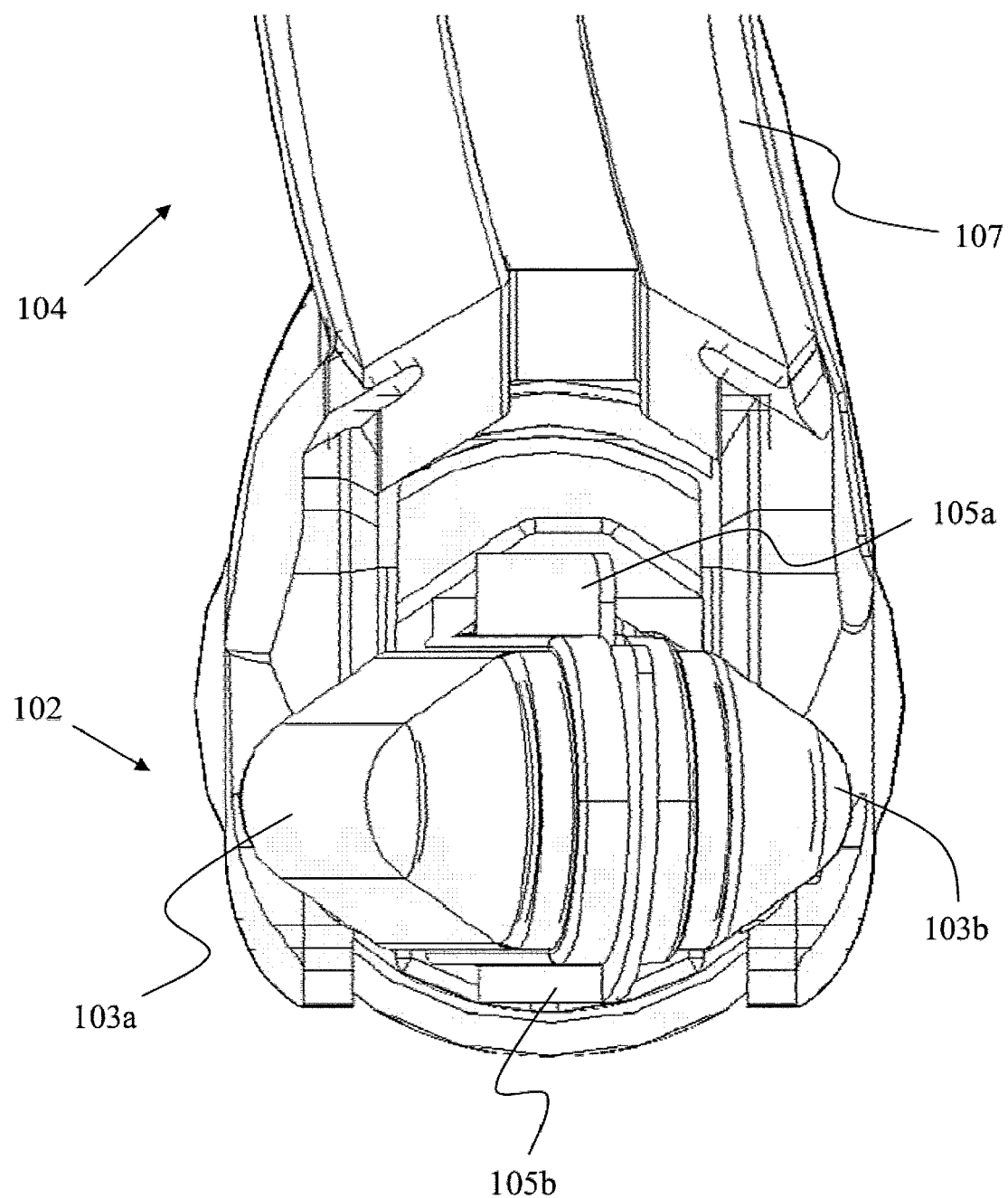
FIG. 9 is a front view of jaws of an electrosurgical instrument in accordance with various embodiments of the invention.
Figure 10:
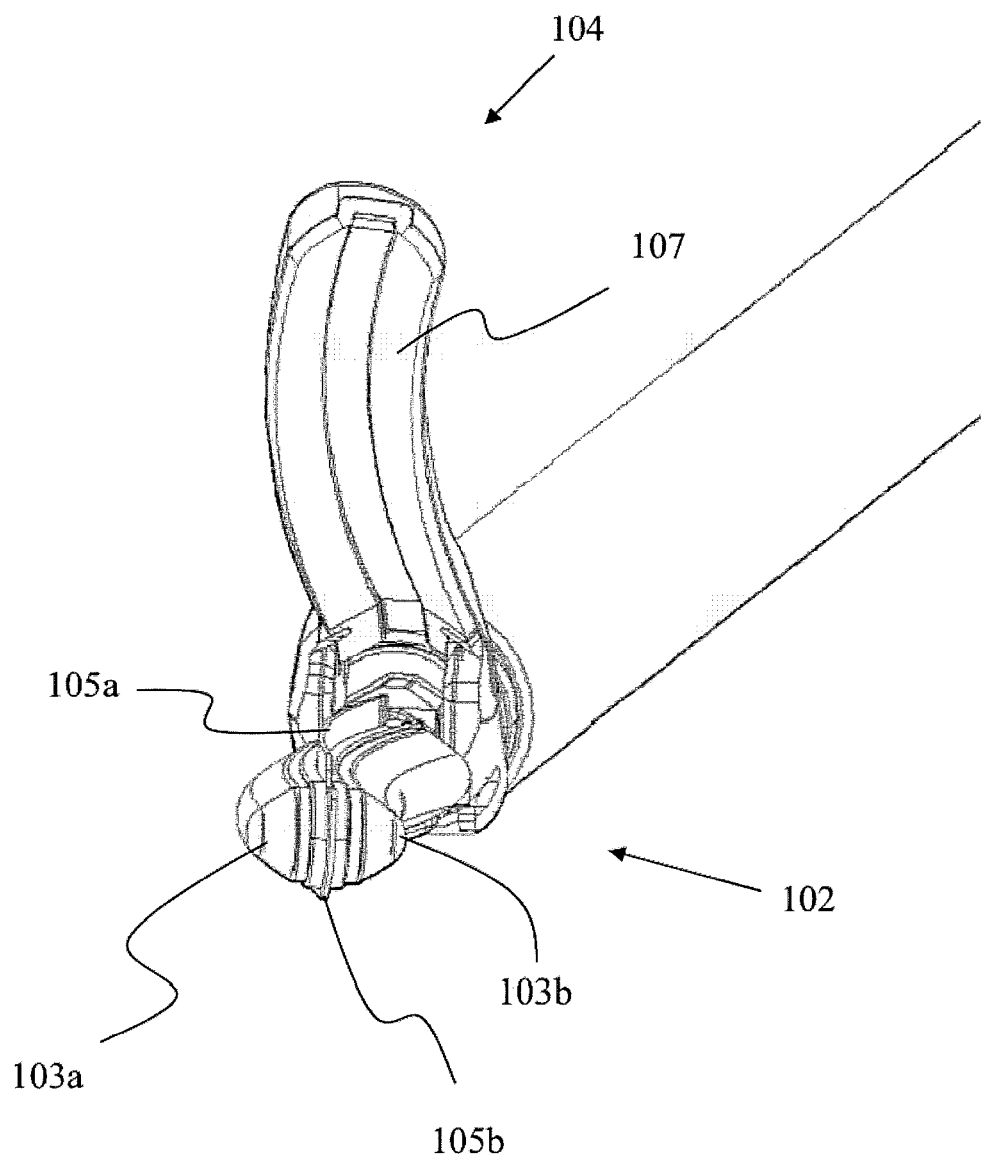
FIG. 10 is a perspective view of jaws of an electrosurgical instrument in accordance with various embodiments of the invention.
Figure 11:
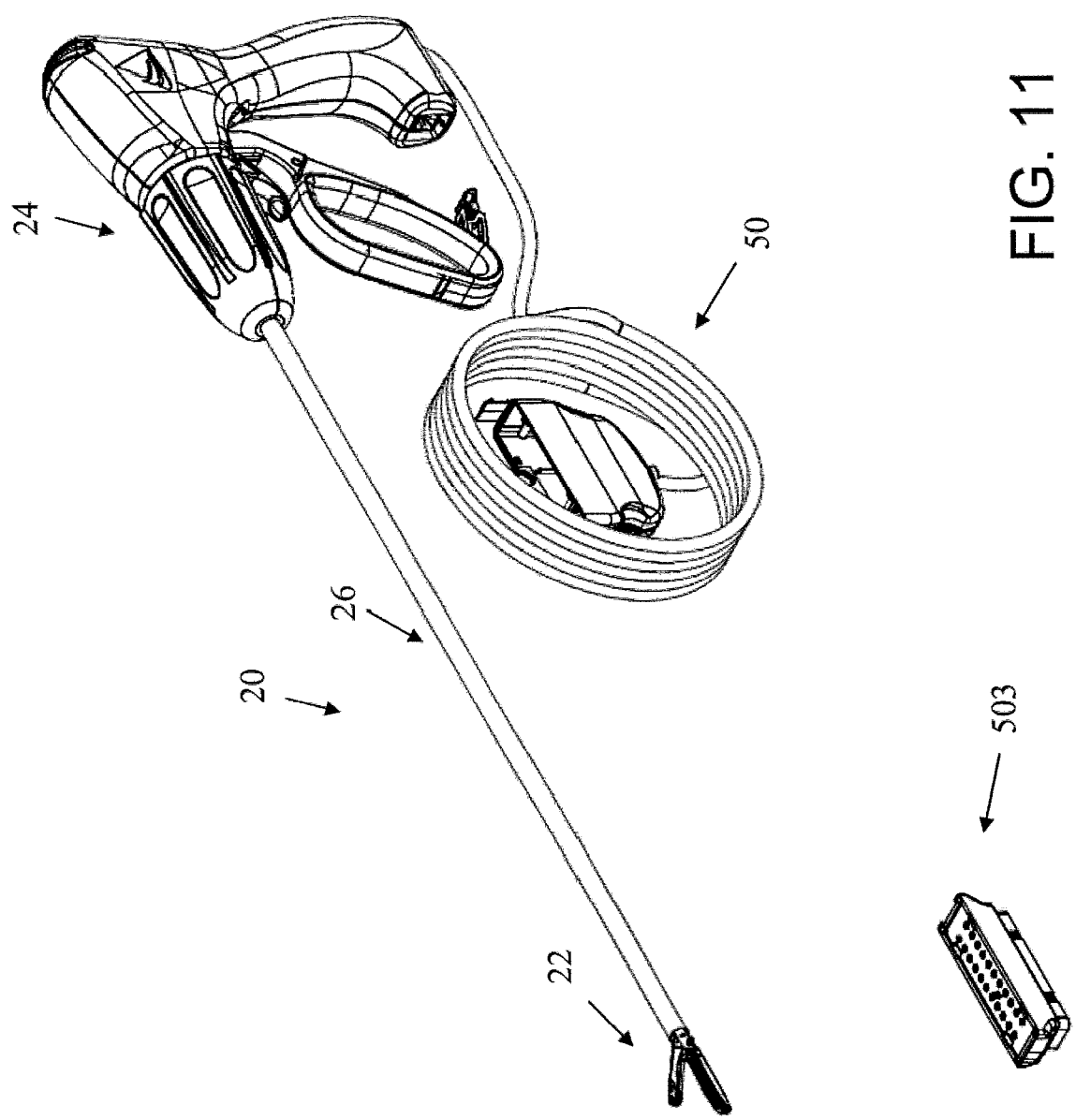
FIG. 11 is a perspective view of an electrosurgical instrument with an associated coupler to connect to an electrosurgical unit in accordance with various embodiments of the invention.
Figure 13A:
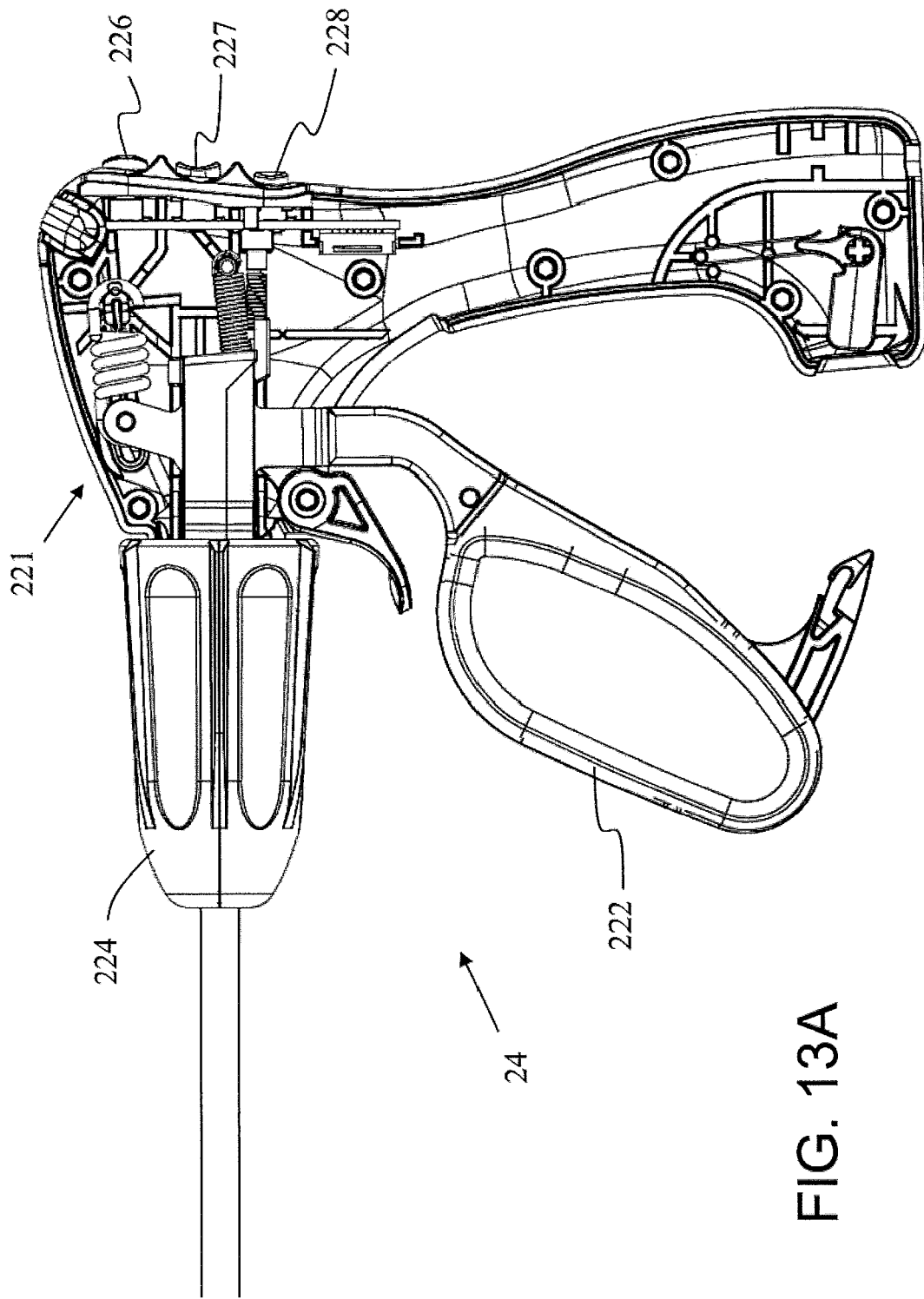
FIG. 13A is a side view of an interior of an actuator of an electrosurgical instrument in accordance with various embodiments of the invention.
Figures 1, 13B:
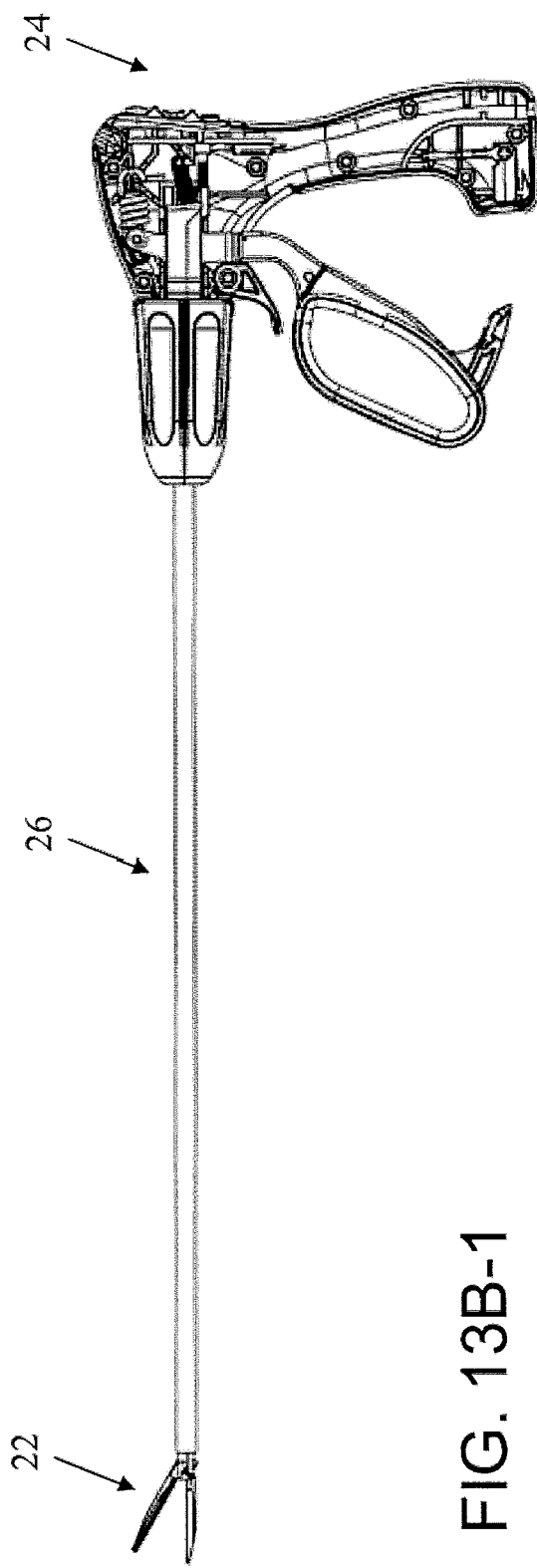
Figures 2, 13B:
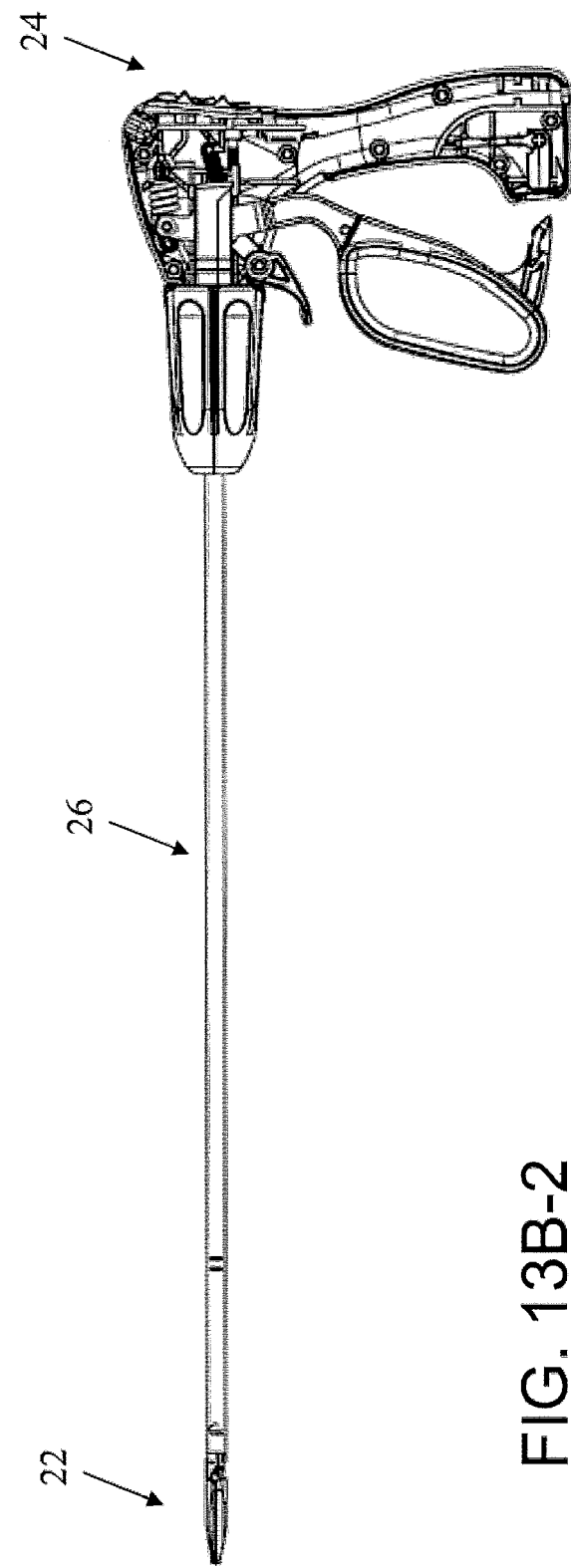
Figures 3, 13B:
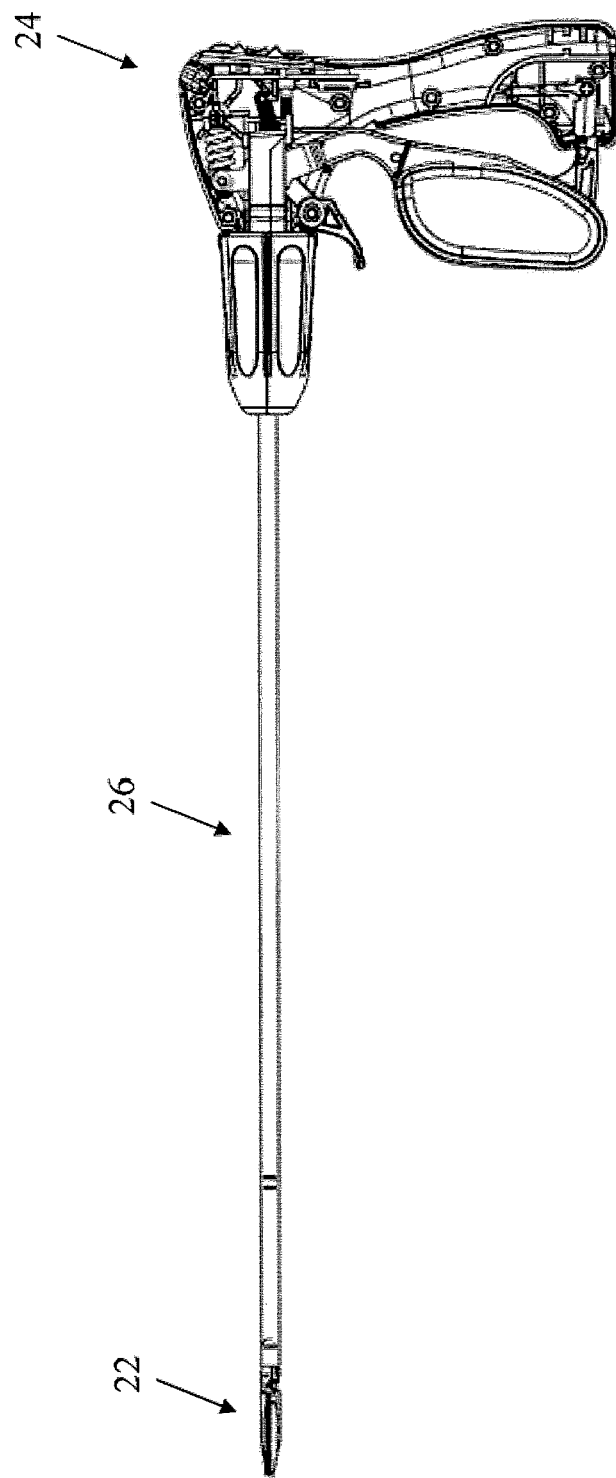
Figures 3, 13C:
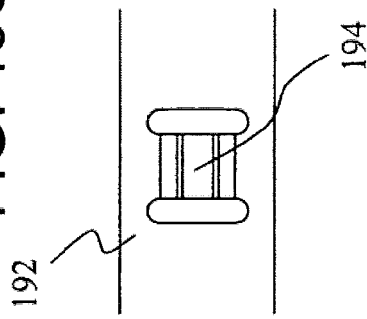
Figures 4, 13C:
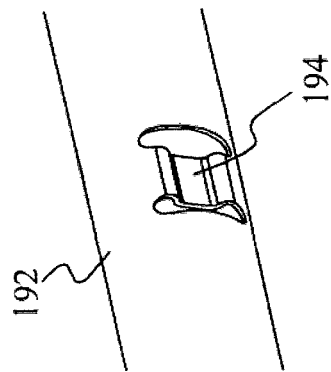
Figures 1, 13C:
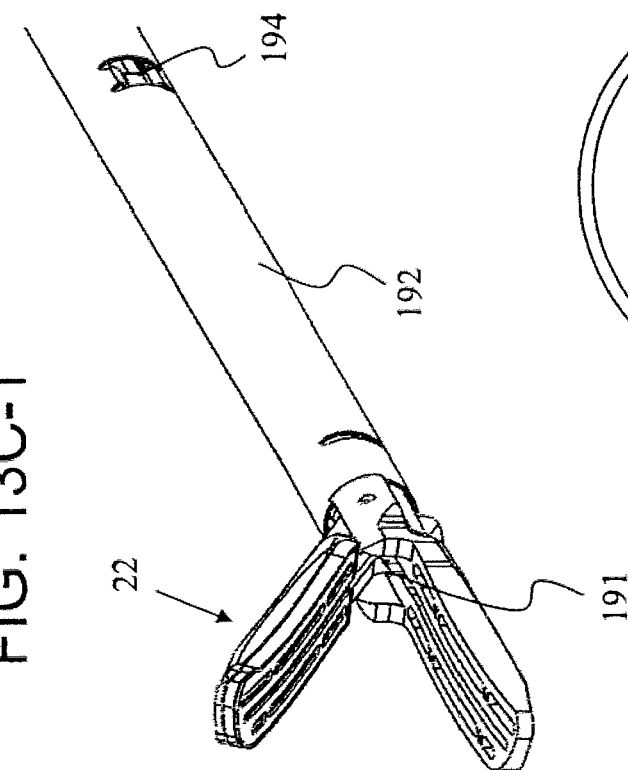
Figures 2, 13C:
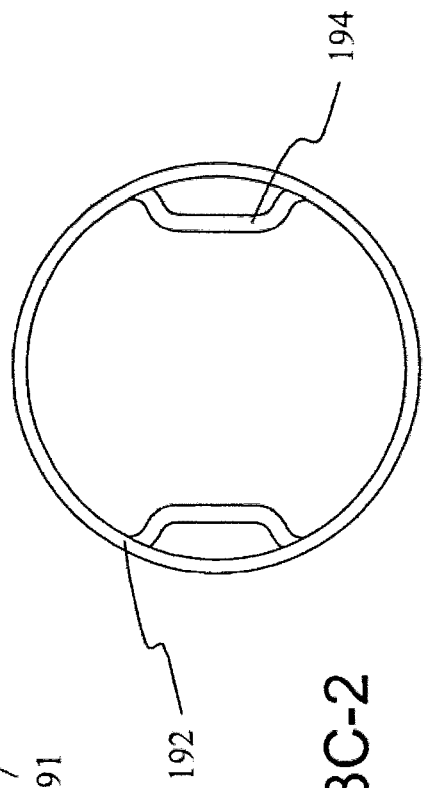
Figure 14:
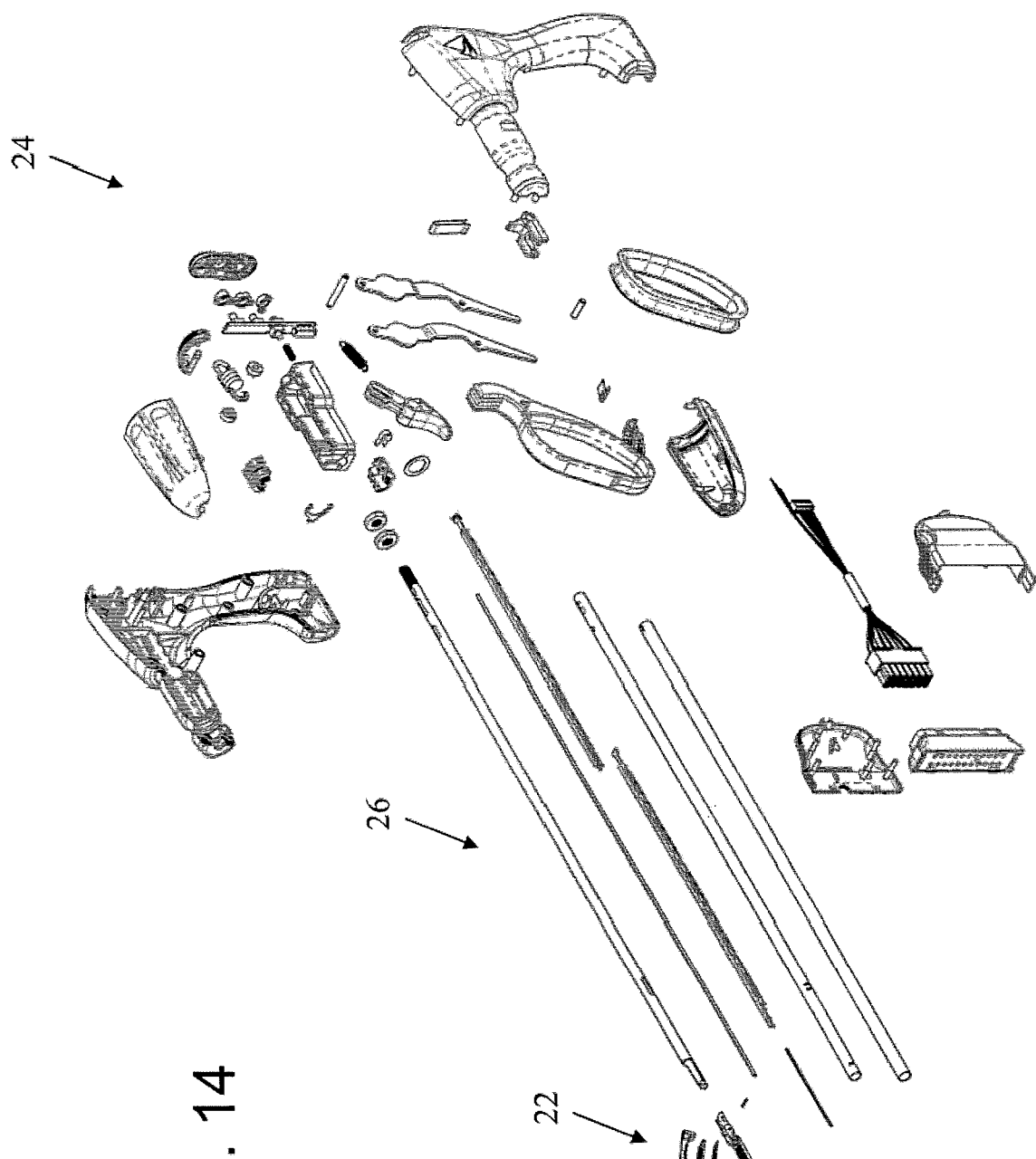
FIG. 14 is a disassembled view of an electrosurgical instrument and coupler in accordance with various embodiments of the invention.
Figure 15A:
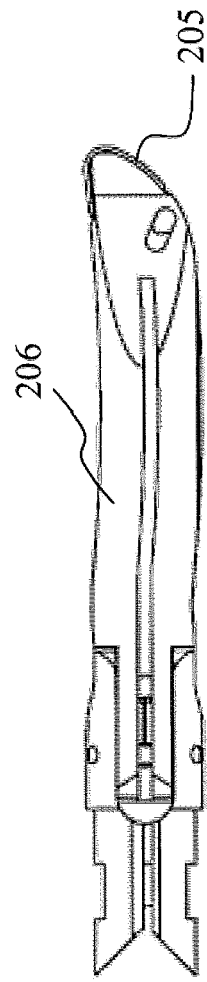
FIG. 15A illustrates a top view of jaws of an electrosurgical instrument in accordance with various embodiments of the invention.
Figure 15B:
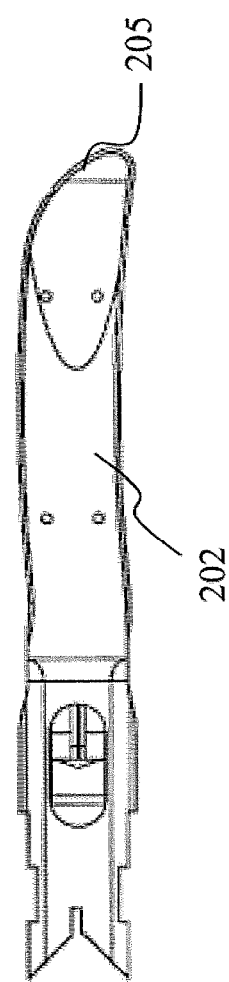
FIG. 15B illustrates a bottom view of jaws of an electrosurgical instrument in accordance with various embodiments of the invention.
Figure 15C:
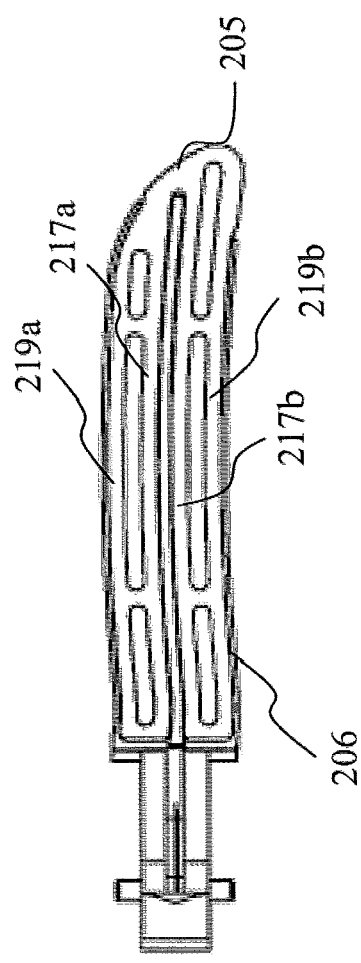
FIG. 15C illustrates a bottom view of one of the jaws of an electrosurgical instrument in accordance with various embodiments of the invention.
Figure 15D:
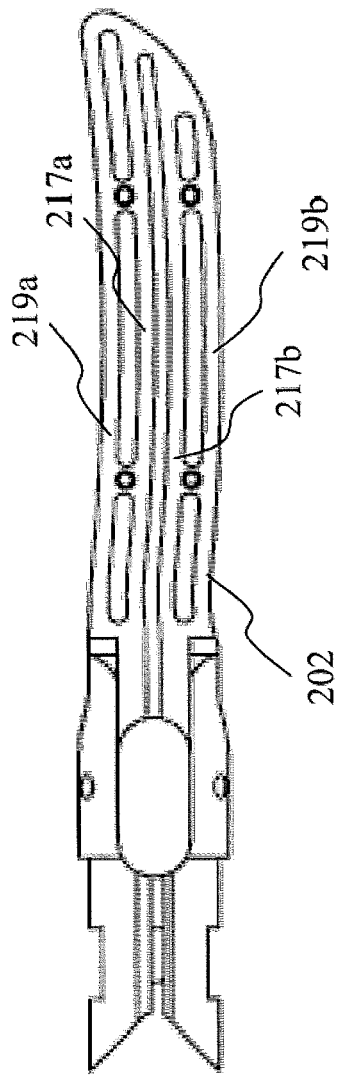
FIG. 15D illustrates a top view of an opposing jaw of an electrosurgical instrument in accordance with various embodiments of the invention.
Figure 15E:
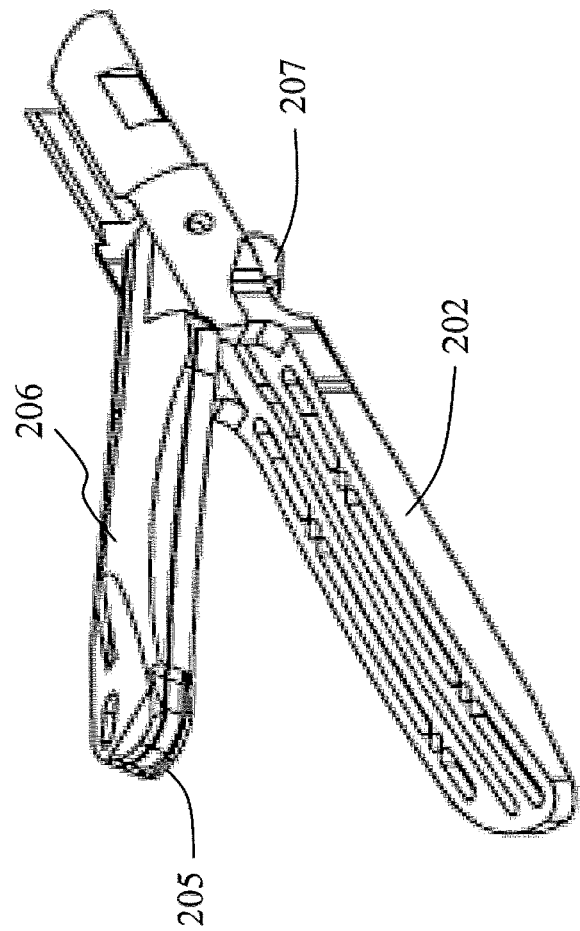
FIG. 15E illustrates a perspective view of jaws of an electrosurgical instrument in accordance with various embodiments of the invention.
Figure 15F:
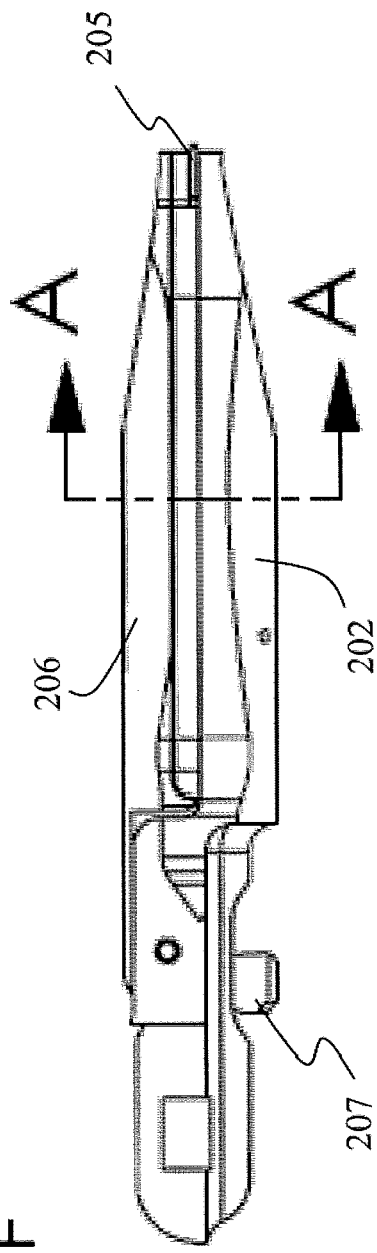
FIG. 15F illustrates a side view of jaws of an electrosurgical instrument in accordance with various embodiments of the invention.
Figure 15G:
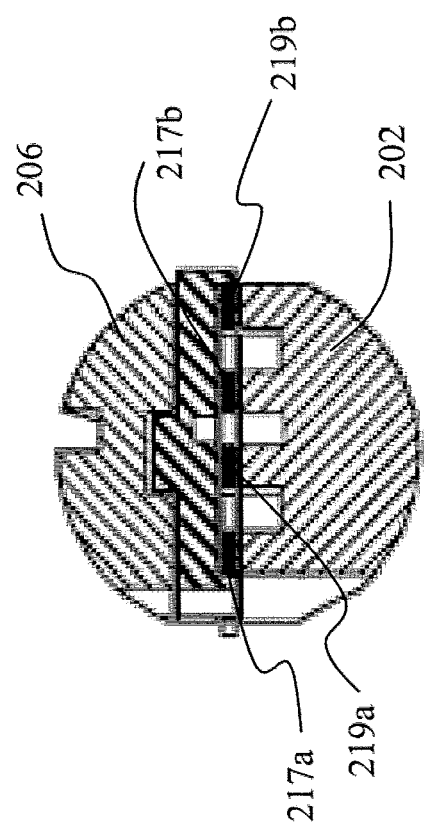
FIG. 15G illustrates a cross-sectional view of jaws of an electrosurgical instrument in accordance with various embodiments of the invention.
Figure 16:
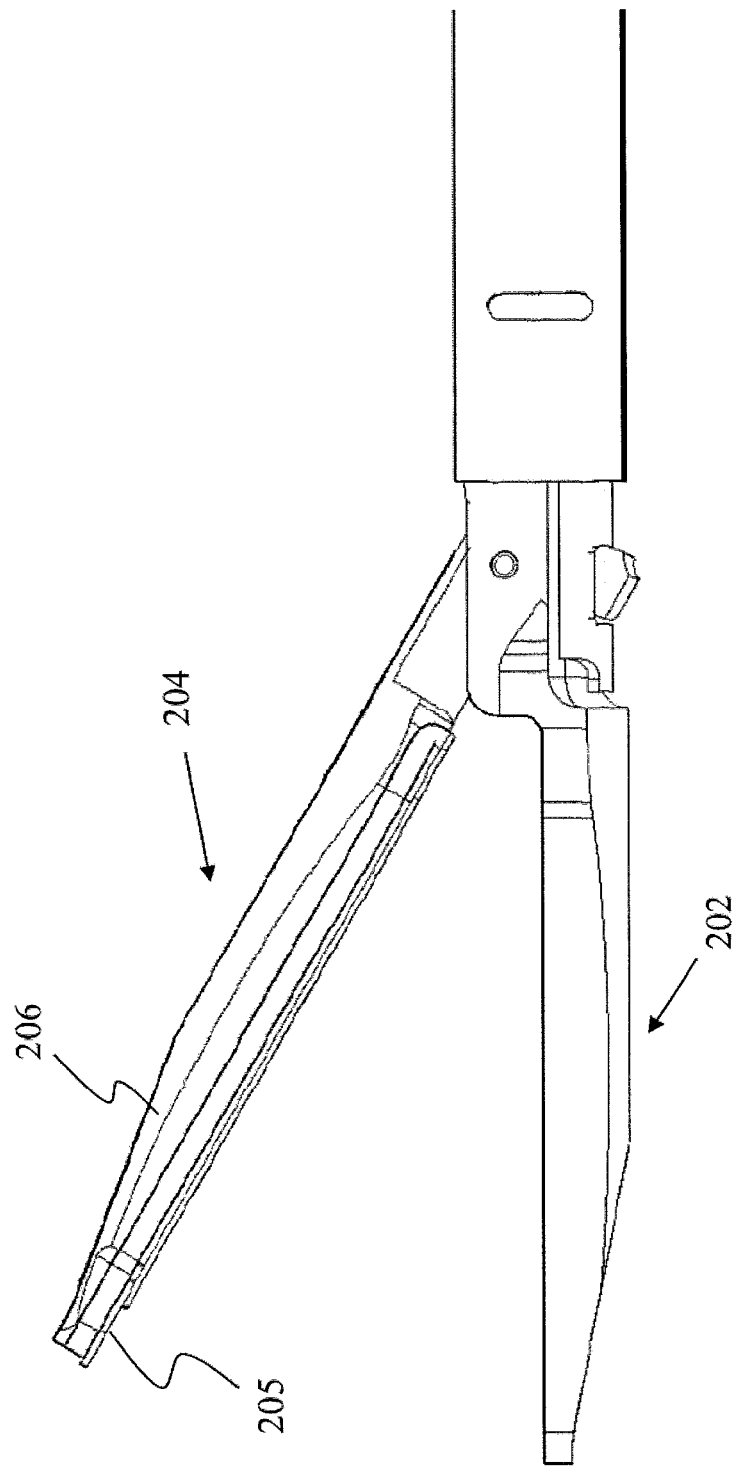
FIG. 16 is a side view of jaws of an electrosurgical instrument in accordance with various embodiments of the invention.
Figure 17:
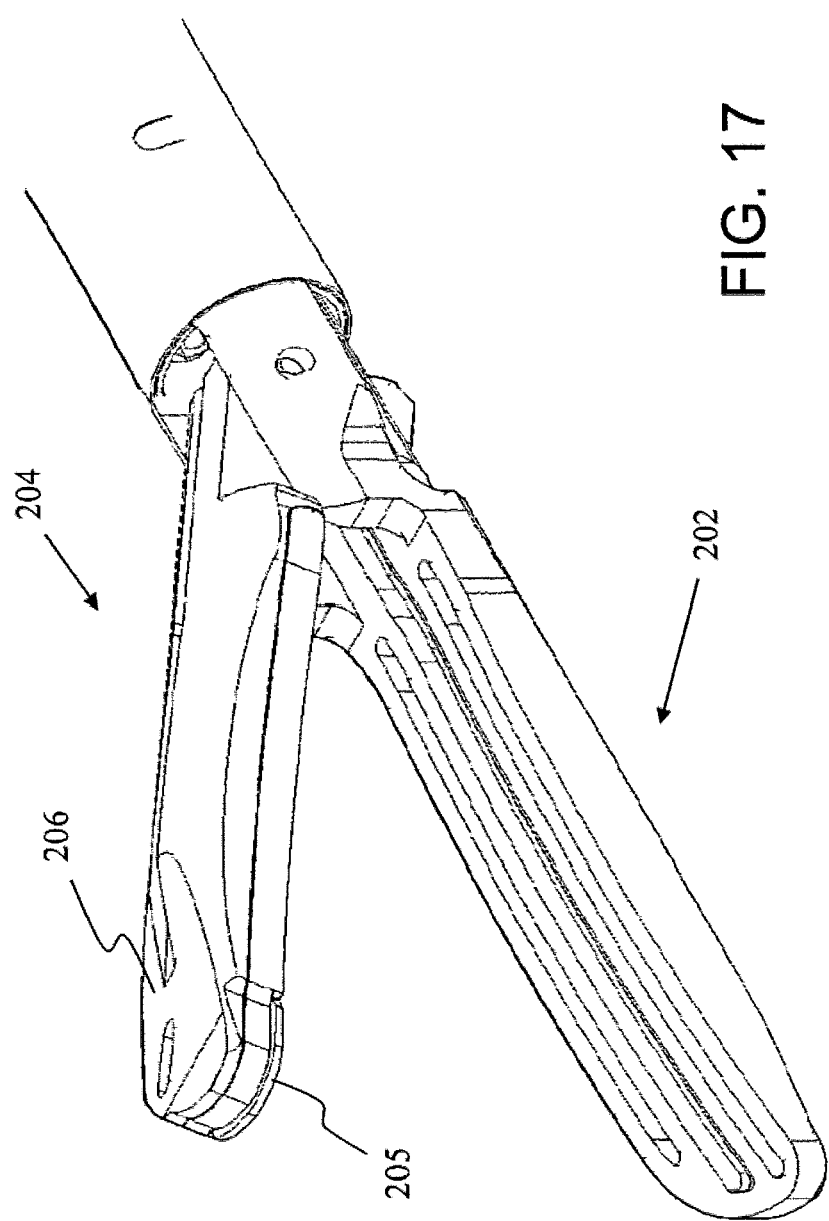
FIG. 17 is a perspective view of jaws of an electrosurgical instrument in accordance with various embodiments of the invention.
Figure 18:
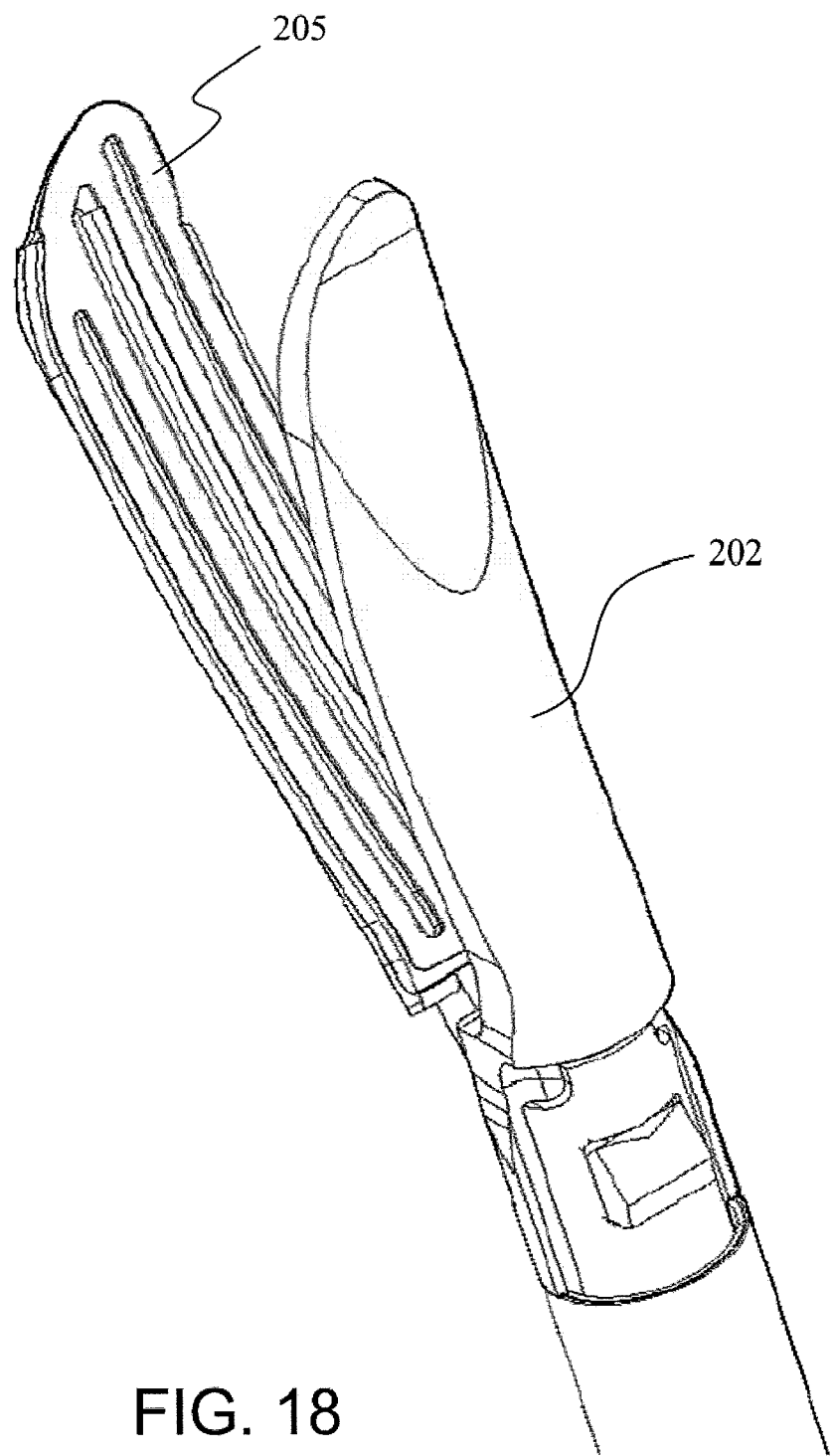
FIG. 18 is a perspective view of jaws of an electrosurgical instrument in accordance with various embodiments of the invention.
Figure 19:
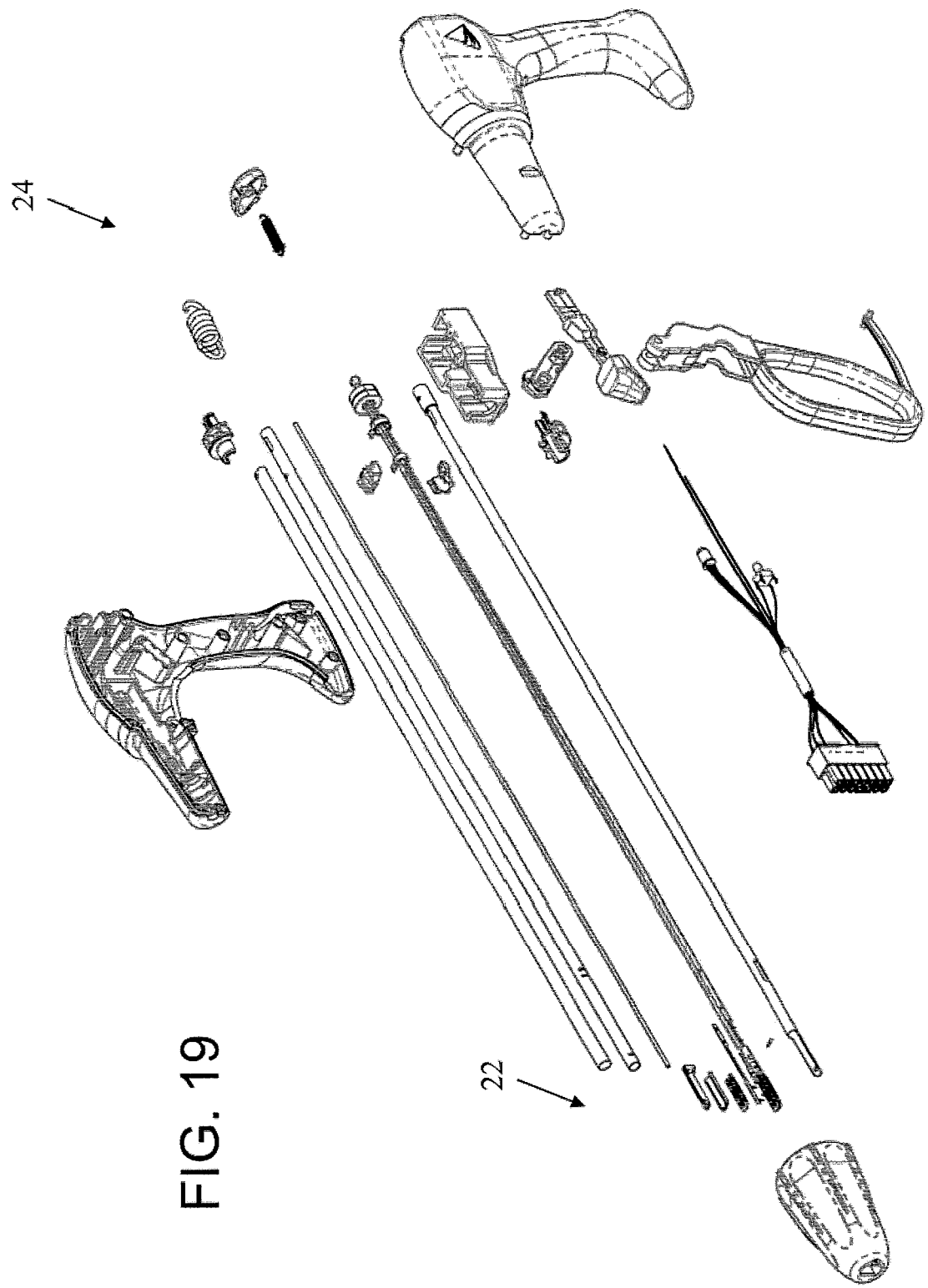
FIG. 19 is a disassembled view of an electrosurgical instrument and coupler in accordance with various embodiments of the invention.
Figure 20:
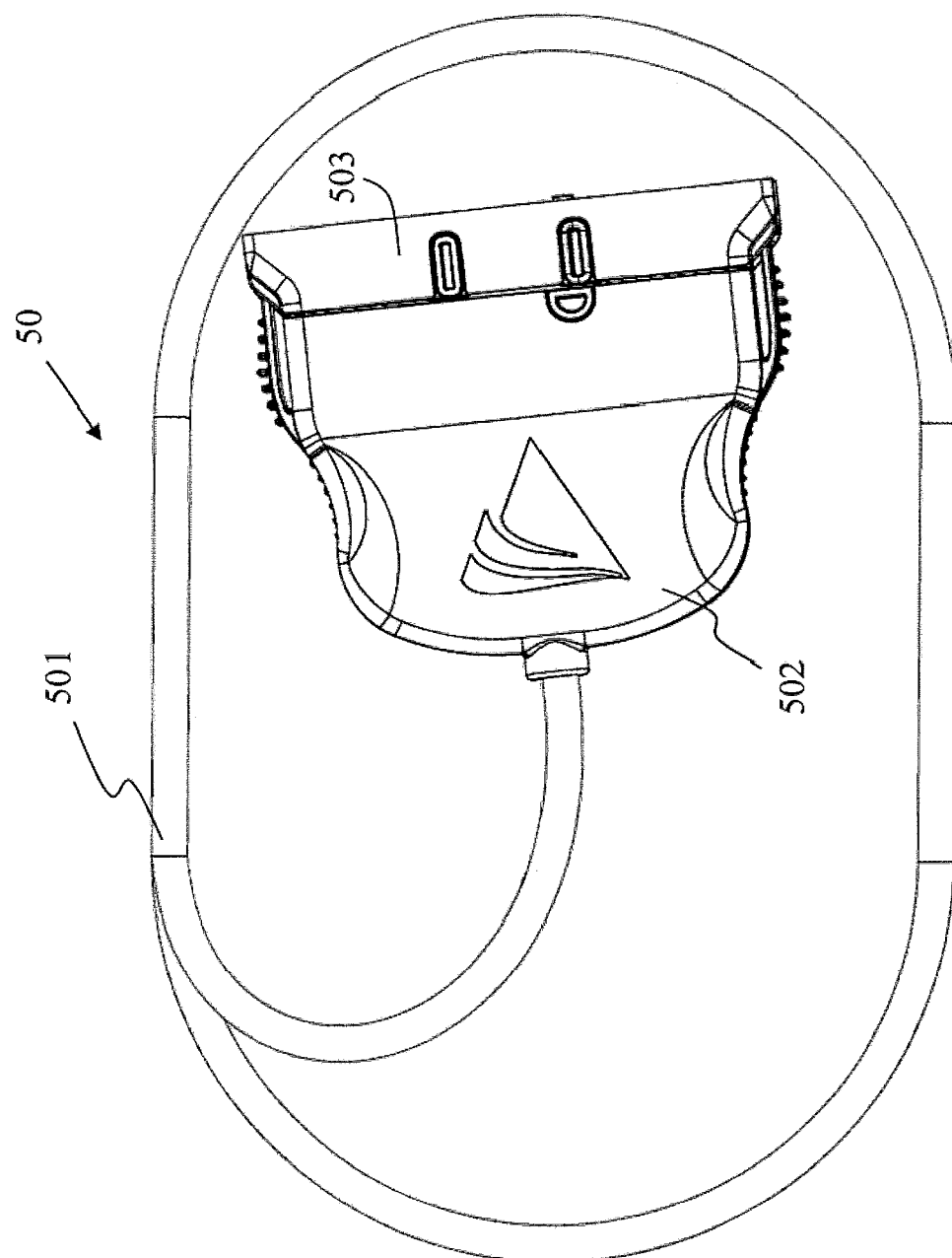
FIG. 20 is a side view of a coupler of an electrosurgical instrument to connect to an electrosurgical unit in accordance with various embodiments of the invention.
Figure 21:
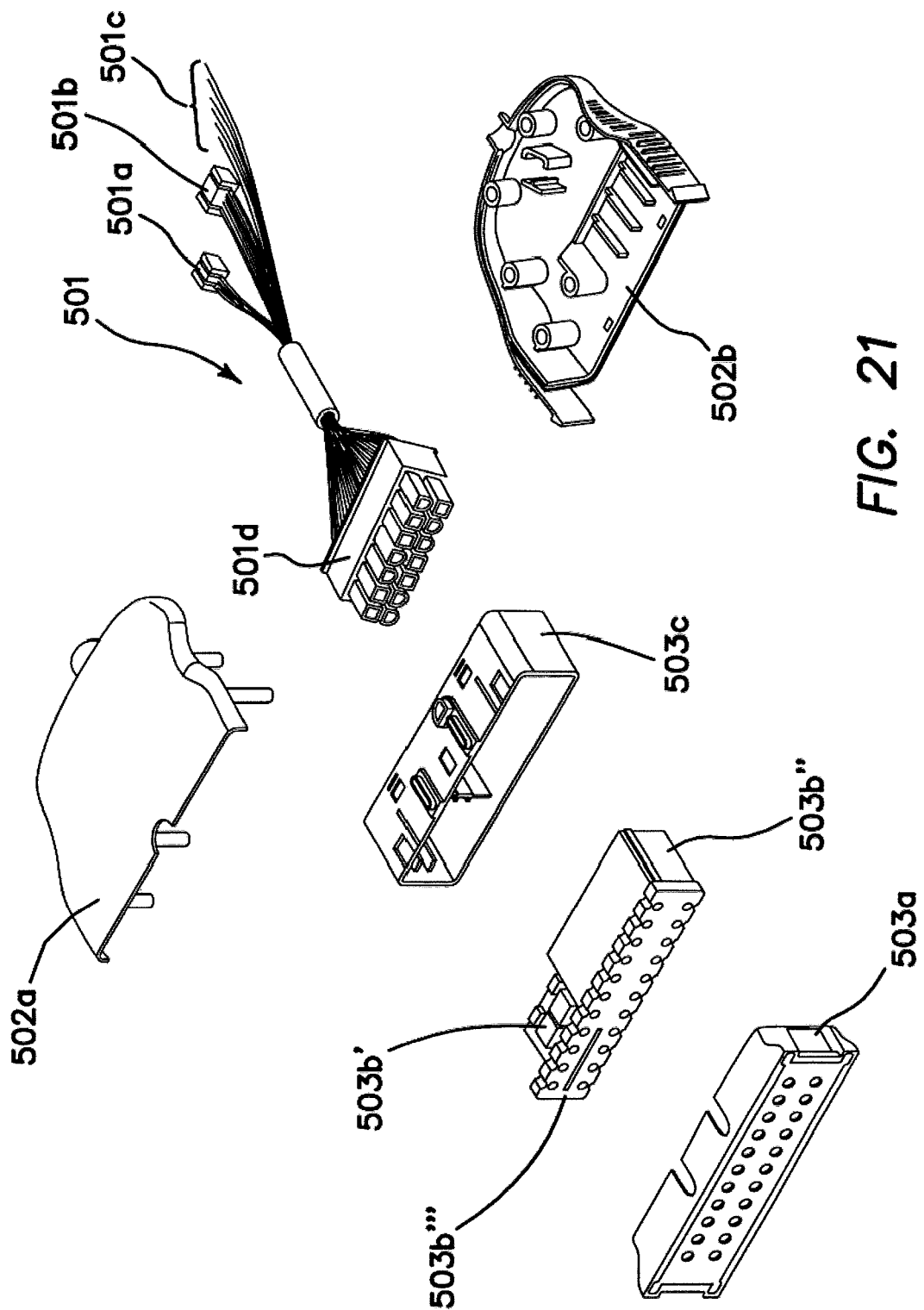
FIG. 21 is a disassembled view of a coupler of an electrosurgical instrument to connect to an electrosurgical unit in accordance with various embodiments of the invention.
Figure 22:
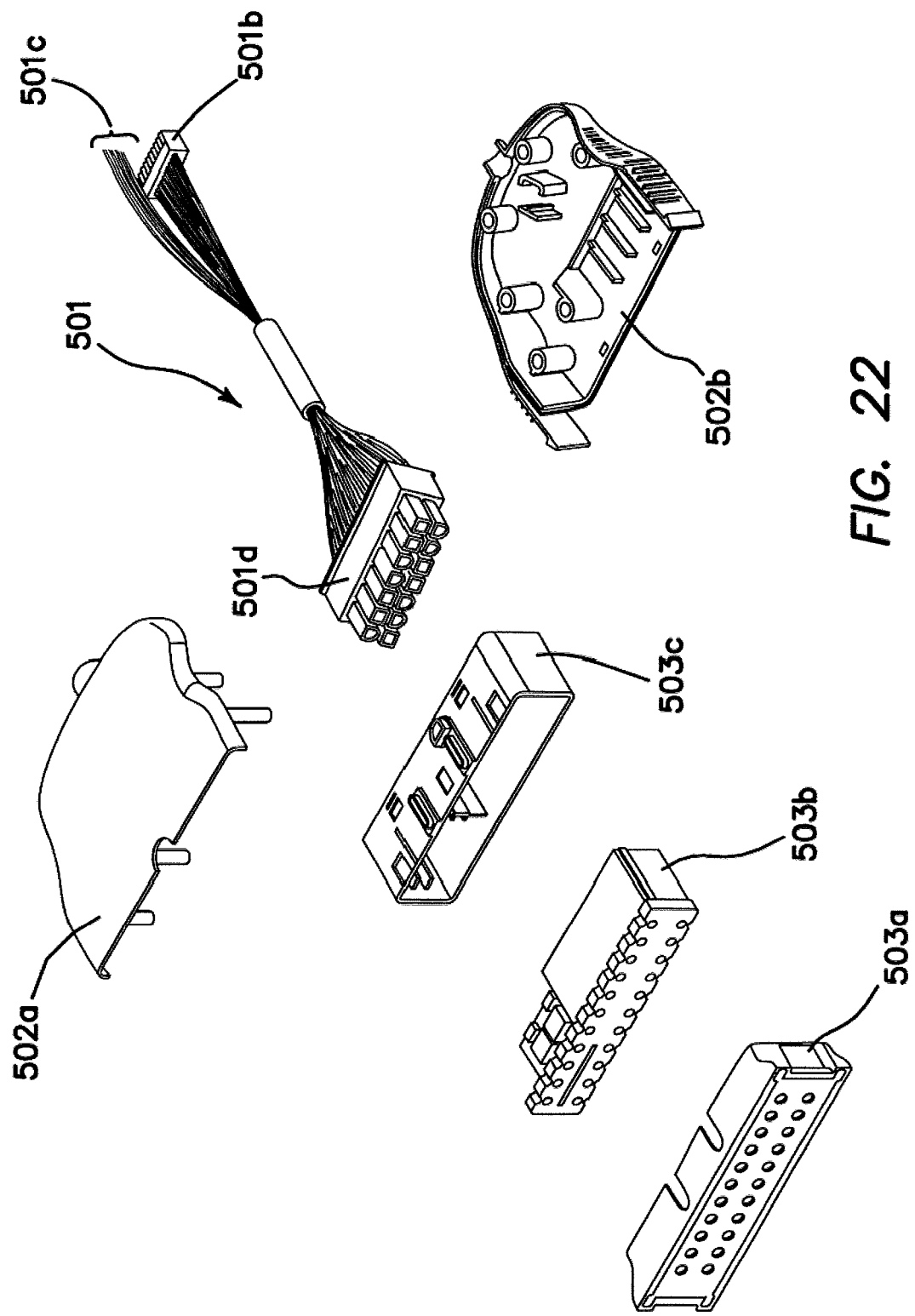
FIG. 22 is a disassembled view of a coupler of an electrosurgical instrument to connect to an electrosurgical unit in accordance with various embodiments of the invention.
Figure 23:
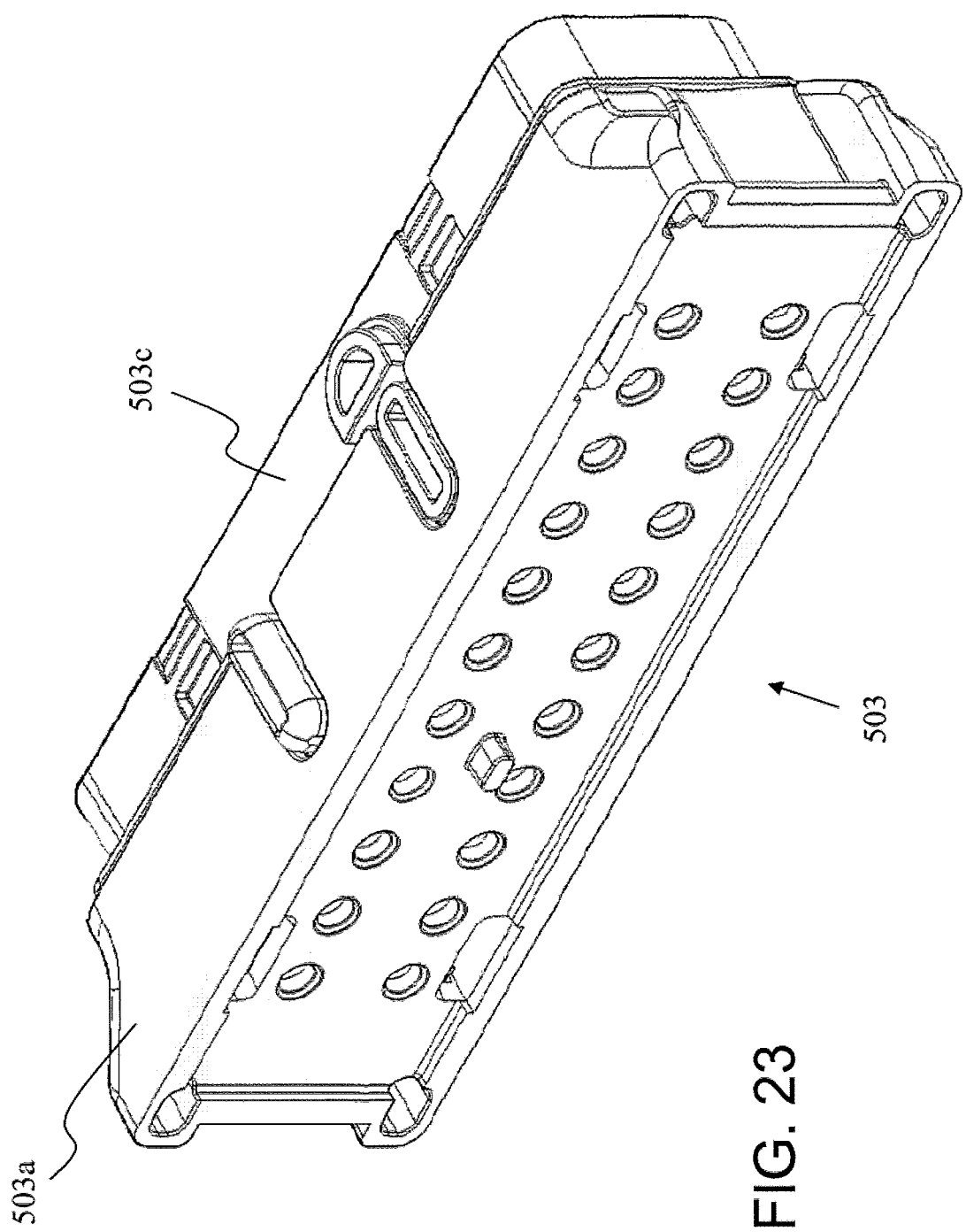
FIG. 23 is a perspective view of a connector in accordance with various embodiments of the invention.
Figure 24:
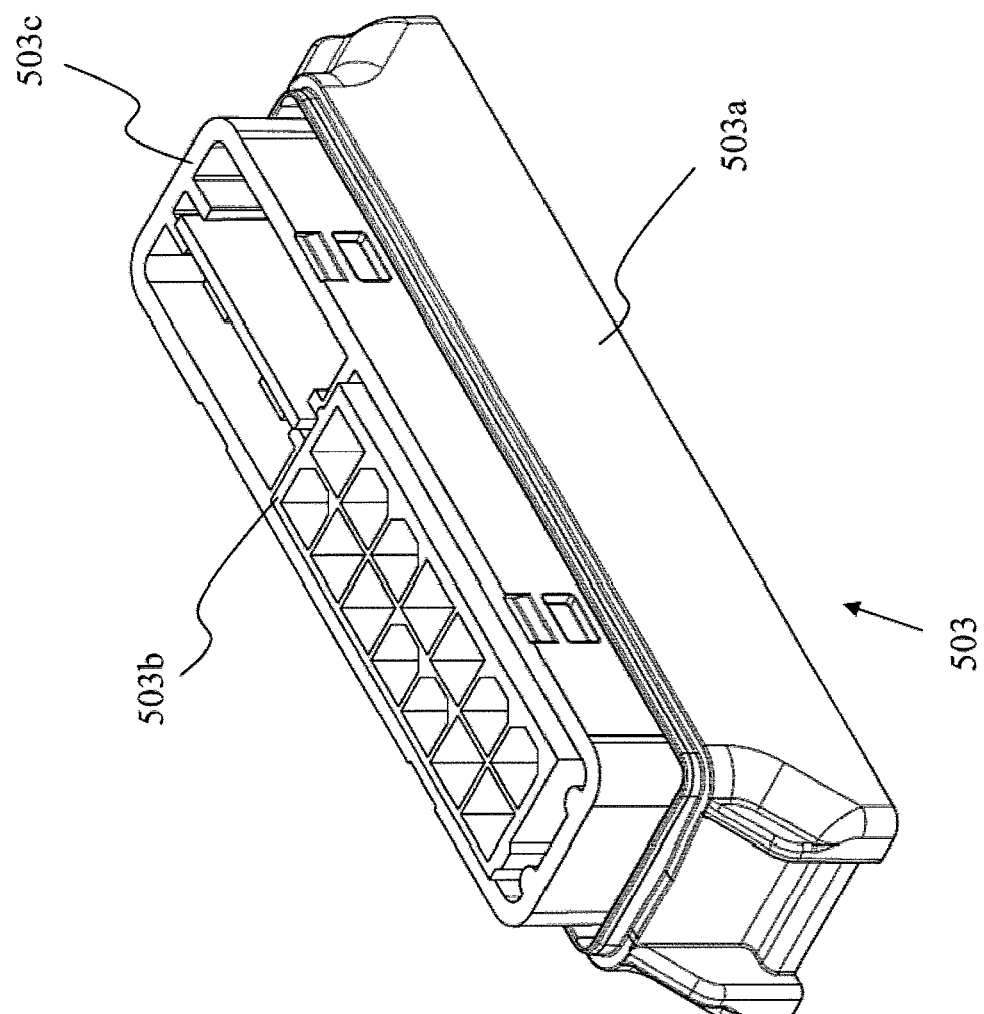
FIG. 24 is a perspective view of connector in accordance with various embodiments of the invention.
Figure 25:
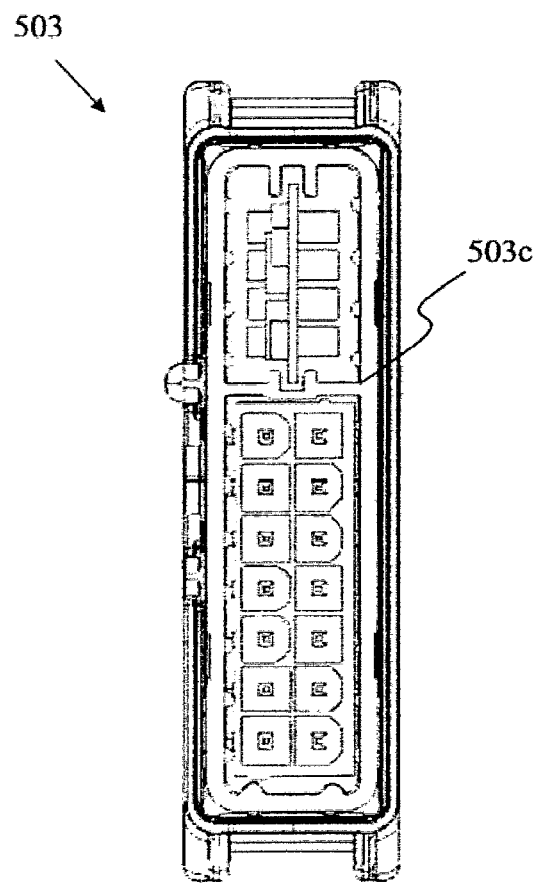
FIG. 25 is a back view of connector in accordance with various embodiments of the invention.
Figure 26:
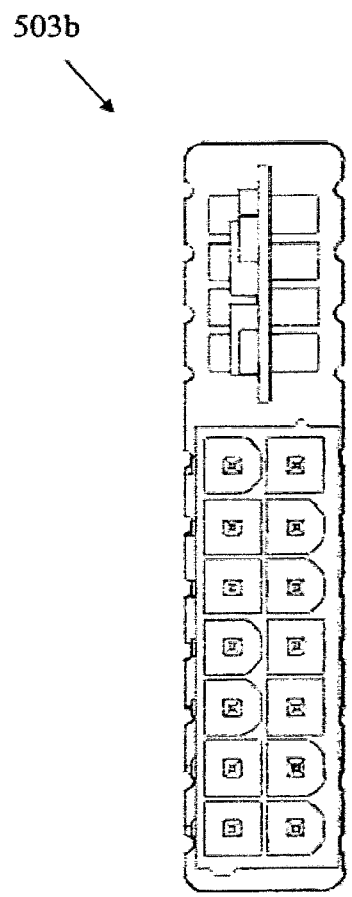
FIG. 26 is a back view of circuitry, memory and pin arrangements of a connector in accordance with various embodiments of the invention.
Figure 27:
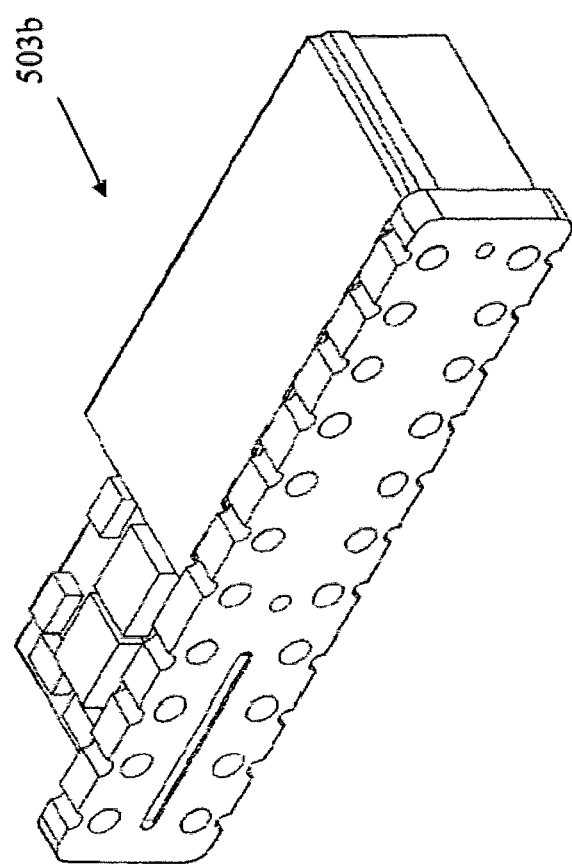
FIG. 27 is a perspective view of circuitry, memory and pin arrangements of a connector in accordance with various embodiments of the invention.
Figure 28:
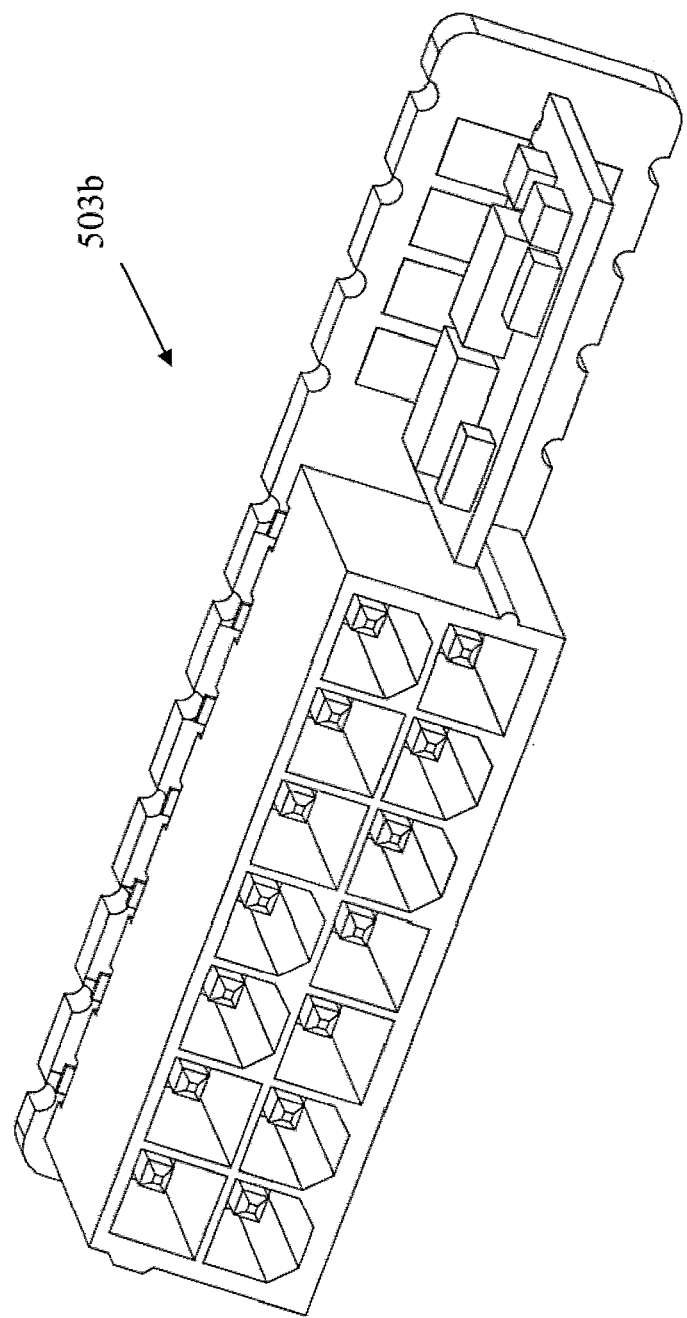
FIG. 28 is a perspective view of circuitry, memory and pin arrangements of a connector in accordance with various embodiments of the invention.
Figure 29:
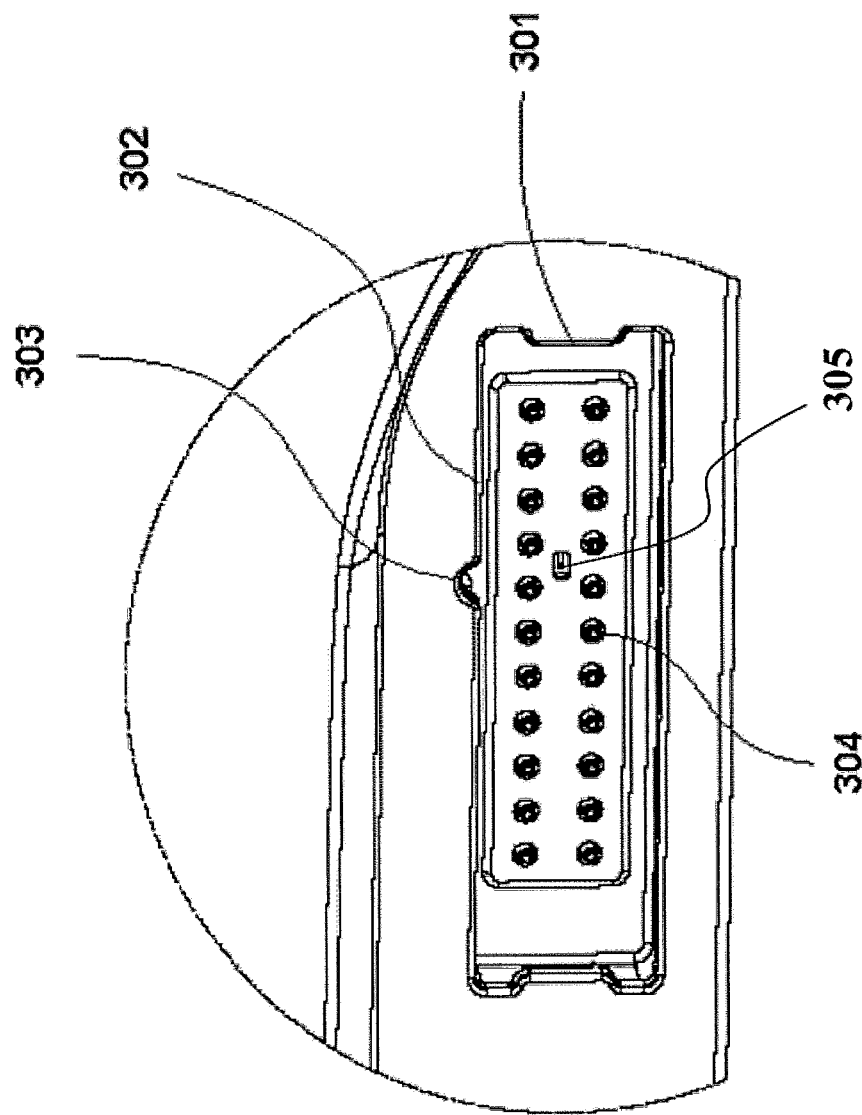
FIG. 29 is a front view of a receptacle of an electrosurgical unit of an electrosurgical unit in accordance with various embodiments of the invention.

The electrosurgical system in one embodiment includes an electrosurgical unit or generator capable of supplying radio frequency energy to one or more removably coupled electrosurgical instruments or tools. Examples of such instruments and connectors between the instrument and the electrosurgical unit are provided in the drawings. Each instrument is particularly designed to accomplish particular clinical and/or technical operations or procedures. Additionally, the coupling or partnership between the electrosurgical unit and instruments are specifically provided to further enhance the operational capabilities of both the electrosurgical unit and instruments such that clinical and/or technical operations are achieved.

One such electrosurgical instrument is shown in FIGS. 1-10 which illustrate a fusion and cutting electrosurgical instrument 10 connectable to an electrosurgical unit in accordance with various embodiments of the invention. As illustrated, the instrument includes jaws 12 for manipulating tissue and the actuator 14 for manipulating the jaws. A shaft 16 connects the jaws to the actuator. In one embodiment, the shaft and jaws are sized and arranged to fit through a cannula to perform a laparoscopic procedure. In one embodiment, the actuator includes a barrel connected to a pivotable trigger 112 for opening and closing of the jaws and to capture and/or compress tissue between the jaws and a rotatable knob 114 and connector providing rotational movement of the jaws. The actuator may also include switches 116, 118 to activate cut, coagulate, seal, fuse or other electrosurgical activities and indicators to identify or highlight the activated or deactivated activity.

The jaws 12 include a first jaw 102 and a second jaw 104. The first jaw is stationary and the second jaw is movable through actuation by the actuator coupled to the second jaw via the shaft and/or components therein. In one embodiment, both jaws may be movable or mobility of the jaws reversed, e.g., the movable jaw is stationary and the stationary jaw is movable. It should also be noted that the first or second jaw being upper or lower jaws is relative as the shaft and the jaws are rotatable and thereby can assume either position. The first jaw includes four electrodes. The first and second electrodes 103a, 103b are substantially hemispherical in shape and cover or occupy a majority of the total surface area of the first jaw. In one embodiment, the hemispherical shape of the electrodes and/or a corresponding mating shape of the second jaw promote tissue after being cut to slide away or otherwise disengage from the jaw. The first and second electrodes are also mirror image of each other and thereby occupy equal halves or side portions along the first jaw 102 as the electrodes extend substantially along the length of the second jaw 104. Disposed between the first and second electrodes are third and fourth electrodes 105a, 105b generally rectangular in shape extending substantially perpendicular relative to the first and second electrodes 103a, 103b and also extending along the length of the first jaw. The edges or the upper portions of the third and fourth electrodes can be beveled or otherwise tapered, slanted, rounded or curved to provide an atraumatic edge to assist in a surgical procedure, e.g., grasping tissue, or alternatively a defined edge to assist for example in cutting tissue.

The third electrode 105a extends towards the second jaw and the fourth electrode 105b extends away from the second jaw. The third electrode 105a extends or has a height somewhat greater than the height or extension of the fourth electrode 105b extending out of the first jaw. The fourth electrode also includes a distal portion 105b' that extends along the tip of the first jaw 102 curving up along the tip. The lengthwise path of the third and fourth electrodes substantially follows the lengthwise shape of the first jaw. Thus, in the illustrated embodiment, the third and fourth electrodes are somewhat curvilinear.

When the first and second jaws 102, 104 are closed, e.g., in a proximate relationship with each other, the third electrode 105a is substantially covered by the second jaw 104 and thereby leaving the third electrode unexposed. The fourth electrode 105b however remains uncovered regardless of the position of the second jaw. Each of the electrodes on the first jaw are electrically insulated or isolated from each other. Additionally, operationally, each electrode can assume a particular electrical polarity. As such, each electrode can assist in accomplishing a particular surgical functionality, e.g., cut, coagulation, fuse, seal, weld, etc. In one embodiment, the second jaw can also include one or more electrodes, e.g., a fifth or sixth electrode, which in conjunction with the electrodes on the first jaw can also assist in accomplishing the desired surgical functionality.

In one embodiment, when the first and second jaws 102, 104 are closed (or not fully opened or partially closed) and a user activates a coagulation operation or condition, the first and second electrodes 103a, 103b assume a particular polarity and a fifth electrode 107 assumes an opposite polarity, through which RF energy is transmitted through clamped tissue between the first and second jaws to coagulate the tissue. Likewise, when the user activates a cut operation and the first and second jaws are closed, the first and second electrodes 103a, 103b assume a particular polarity and the third electrode 105a on the first jaw assumes an opposite polarity to first coagulate the tissue and then to cut tissue between the first and second jaws 102, 104 and in particular at a point or section where the third electrode 105a contacts the tissue between the jaws. In one particular embodiment, in a cut operation with the first and second jaws are closed, the first and second electrodes 103a, 103b assume opposite polarity to coagulate the tissue up to and/or prior to complete coagulation or a predetermined pre-cut condition. After reaching the pre-cut condition based on a predetermined phase value, in one embodiment, the first and second electrodes 103a, 103b assume a polarity opposite to the polarity of the third electrode 105a. In one embodiment, the actuator 14 includes a trigger switch that is inactive or not activated by the position of the trigger positioned away from the switch.

Additionally, when the first and second jaws are not closed (fully opened or partially opened) and a user activates a coagulation operation or condition, the first electrode 103a assumes a particular polarity and the second electrode 103b assumes an opposite polarity, through which RF energy is transmitted through tissue between the first and second electrodes 103a, 103b to coagulate the tissue. Likewise, when the user activates a cut operation and the first and second jaws are not closed, the first and second electrodes assume a particular polarity and the third and fourth electrode 105a, 105b on the first jaw 102 assumes an opposite polarity to first coagulate the tissue and then to cut tissue between the electrodes and in particular at a point or section where the third electrode contacts the tissue between the jaws. It should be appreciated that over or completely coagulating tissue increases the difficulty in cutting the tissue as the tissue's conductivity is substantially reduced. This is contrary to the tendency to "over coagulate" tissue to ensure that blood loss is avoided (i.e., the tissue is sealed).

In one embodiment, a trigger switch 103 of the actuator 14 is activated by the position of the trigger 112 causing contact with the switch. The trigger in the illustrated embodiment includes a flexible arm 101 connected to or incorporated with the trigger utilized to activate or deactivate a trigger switch in the actuator 14. The trigger switch 103 is internal or housed within the actuator and not accessible by a surgeon. The trigger switch however activates or permits the activation or effect of one or more external switches that is accessible by the surgeon. For example, a "cut" button or switch accessible by a surgeon will not operate or cause the application of RF energy to cut tissue even if the button is depressed by the surgeon unless the internal trigger switch is also activated. In one embodiment, the internal trigger switch is only activated depending on the position of the trigger and/or the jaws. The internal trigger switch can also be activated via relays based on commands or programming provided by the electrosurgical unit, the instrument and/or the connector. It should be appreciated that in various embodiments the internal trigger switch does not activate or permit by itself the activation of RF energy and thereby avoids unintended operation of the instrument without active and deliberate participation by the surgeon. Additionally, it should be appreciated that in various embodiments the switches accessible by the surgeon can only activate while the internal trigger switch is also simultaneously active or activated and thereby avoids unintended operation of the instrument without active and deliberate participation by the surgeon and active communication or deliberate programming or commands embedded or provided for the electrosurgical unit, the instrument and/or the connector.

It should thus be appreciated that tissue between the first and second jaws can be cut with the jaws closed or not closed. Additionally, tissue can be cut beneath and/or in front of the first jaw, i.e., tissue not between the first and second jaws, when the first and second jaws are not closed (the cutting occurring to the tissue between the fourth and first electrodes; the fourth and second electrodes; and/or the fourth and first and second electrodes). It should also be appreciated that the electrodes to assume the appropriate polarity or connection for a particular operation, e.g., cut or coagulation, are switched in or connected to the energizing circuitry of the electrosurgical unit to apply the specific RF energy to cut or coagulate tissue. Such switching or control information in one embodiment is provided via script data stored on a memory chip of a plug adapter or coupler connectable to the electrosurgical instrument.

As previously described, in one embodiment, the first jaw 102 is stationary or not movable and includes inner and outer vertical electrodes. Such an electrode configuration provides directed energy delivery based on the position of one jaw relative to the other jaw. For example, the electrode configuration provides cutting at the tip of a jaw and/or along the length of both the outer and inner surfaces of the jaw. Also, with the electrode configuration being located on a jaw that is stationary relative to the other jaw operation when the jaws are open can be performed such that a surgeon can manipulate the direction or path of the cut directly through manipulation of the actuator as the jaw is stationary in relation to the shaft and the actuator. In one embodiment, tissue captured between the jaws can also be cut by the electrodes on both jaws operating together.

It should be appreciated that the addition of multiple electrodes on one or more jaws is not a trivial design choice. Reducing the number electrodes is often desired, especially in the limited confines of laparoscopic procedures, to avoid shorting or undesired thermal spread or modification of tissue, e.g., charring or cutting of tissue, introduced at least by the additional conductive material proximate the active or energized electrodes. Accordingly, the electrodes as provided in various embodiments are specifically arranged, structured and utilized to overcome such challenges.

In one embodiment, an electrosurgical instrument is provided that includes multiple cutting blades or surfaces. Some or all the blades are movable and/or electrically connected. Operationally, the instrument or parts thereof can be energized to fuse or coagulate and cut tissue as needed. In another embodiment, one or more blades are stationary and/or electrically connected.

In one embodiment, wires are welded onto the electrodes in the first jaw 102. The wires are routed around a rotary connector 27 and conductive rings 24a-24d are attached to the rotary connector within the actuator 14. In one embodiment, a rotary lock is installed and holds the conductive rings in place. In one embodiment, conductive ring 24a is coupled to the electrode 103a and conductive ring 24d is coupled to the electrode 103b. The conductive ring 24b is coupled to the electrode 105a and conductive ring 24c is coupled to the electrode 105b. The rotary connector 27 includes one or more slots through which wires from electrodes are threaded or managed through slots. Conductive rings are secured to the rotary connector such that individual corresponding wires for associated electrodes are electrically connected to associated conductive rings. As such, the conductive rings rotate as the rotary connector rotates along with the associated wires extending from the electrodes of the jaws through the shaft and to the rotary connector and thus the wires do not wind around the shaft as the jaws are rotated.

The actuator 14 also includes contact brushes 26a-d are disposed in contact with an associated conductive ring 24a-d. For example, in the illustrated embodiment, contact brush 26a is positioned next conductive ring 24a. Each contact brush is also connected to a wire or similar connections to the connector and ultimately to an electrosurgical unit to provide or communicate RF energy, measurement, diagnostic or similar signals through an associated electrode at the jaws of the electrosurgical instrument. Slots within the handle of the actuator in one embodiment facilitate the wire placement and connection with a contact brush and the electrosurgical unit. As such, the conductive rings provide a conduction or communication surface that is continually in contact with the contact brushes and vice versa regardless of the rotation of the shaft. In one embodiment, the contact brushes are slanted or biased to maintain contact with the conductive rings.

A "U" shaped tube clip 25 within the actuator 14 is welded onto a wire in which the other end of the wire is welded to the second jaw 104. In one embodiment, the second jaw 104 is held in place by a pull tube. The pull tube serves as an electrical connection for the second jaw 104. The conductive rings and clip provides constant electrical conductivity between the electrodes and the electrosurgical unit while simultaneously allowing or not hindering complete 360 degrees of rotation in any direction of the jaws 102, 104. For example, wires coupled to the electrodes to the rings or clip follow the rotational movement of the jaws and the shaft attached thereto and as a result do not get intertwined or tangled within or along the shaft or the actuator thereby limiting rotational movement, disconnecting or dislodging the connections and/or interfering with operation of the actuator.

In one embodiment, individual wires are welded to individual electrodes of the jaws of the electrosurgical instrument. The wires, e.g., wire 29, are threaded along the shaft connected to the jaws through a rotary knob and into slots in a rotary connector 27. In one embodiment, some of the wires are placed on one side of the connector and other wires on an opposing side of the connector. The wires are staggered along the length of the connector to match the staggered placement of the conductive rings. In one embodiment, the staggered placement prevents inadvertent shorting or conduction between rings. Conductive rings are thus in one embodiment slide over the connector and are placed in spaced slots along the connector to mate each conductive ring to an associated staggered wire. Individual wires in one embodiment are also installed into slots in the handle of the actuator and an associated contact brush is installed over the associated wire to mate each wire to an associated contact brush. The rotary connector thus installed into the handle of the actuator mates or sets up an electrical connection or conduction area for each conductive ring with a corresponding contact brush.

Turning now to FIGS. 11-19, a fusion and cutting electrosurgical instrument 20 is shown connectable to an electrosurgical unit in accordance with various embodiments of the invention. The instrument 20 includes jaws 22 connected to a shaft 26 that is connected to an actuator 24 which when manipulated manipulates the jaws 22. In one embodiment, the actuator includes a floating pivot mechanism 221 including a pivot block connected to a trigger 222 for the opening and closing of the jaws and to capture and/or compress tissue between the jaws. The actuator in one embodiment also has a rotary knob 224 and connector providing rotational movement of the jaws and in one embodiment also includes a blade trigger 225 coupled to a push bar or blade shaft coupled to or incorporating a distal cutting element to translate the cutting element through the jaws and to cut tissue between the jaws. The actuator may also include switches 226, 227, 228 to activate cut, coagulate, seal, fuse or other similar electrosurgical activities and indicators to identify or highlight the activated or deactivated activity.

In accordance with various embodiments, a blade or cutter 191 is included in the instrument and is movable relative to the jaws 22 of the instrument. The cutter is displaced substantially orthogonal to surface one or both jaws and is movable along a longitudinal axis of the instrument. In one embodiment, the cutter is positioned horizontally or parallel relative to one or both jaws. The cutter in one embodiment can move outside the confines of the jaws or is placed on the outside or outer surface of one or both jaws. For example, the cutter can act as a retractable electrode or retractable blade placed within one or both jaws and exposed externally or on the outside of a jaw upon manipulation by an actuator coupled to the cutter. The cutter edge can extend along all or some of the cutter and some or all of the edge is sharpened, beveled, energized or otherwise configured to cut tissue.

In the illustrated embodiment, the cutter 191 traverses through a channel within the jaws to cut tissue between the jaws. The channel does not extend beyond the outer periphery of the jaws and thus the cutter remains within the distal confines of the jaws. A blade shaft 196 is connected or incorporated with the cutter as a monolithic structure extends into the actuator. A blade trigger upon actuation moves the cutter through the channel in the jaws. The blade shaft 196 is biased to pull the cutter back to its initial rest position once the trigger is released. In one embodiment, a spring coupled to the blade shaft biases the cutter towards the actuator. Actuation of the blade trigger thus overcomes the spring bias to move the cutter distally through, out or along the inside or outside of one or both jaws.

In one embodiment, one or more stops 195, 197 along the blade shaft limits movement of the blade shaft 196 and thus the cutter 191. In the illustrated embodiment, a stop projection disposed on or within the blade shaft moves with the blade shaft and when moved distally to a predetermined point, e.g., near a distal end of the channel in a jaw, the stop projection interacts with a corresponding stop projection or slot 194 preventing further distal movement of the stop projection beyond the stop slot. In one embodiment, the stop slot is disposed on, from or within a cover tube 192 disposed over the blade shaft and positioned to contact the stop projection on the blade shaft when the cutter is moved distally to a predetermined point.

In one embodiment, a second stop projection 197 is disposed on or within the blade shaft 196 and spaced from a first stop projection 195. The second stop projection is placed closer to the actuator or away from the jaws 22. In the illustrated embodiment, the second stop projection 197 prevents the spring from pulling the blade proximally beyond a predetermined point, e.g., near a proximal end of the channel in a jaw. As such, in various embodiments, the blade stop limits forward and/or reverse travel of the blade or cutter when extended or retraced either towards or away from the distal end of the instrument. The blade stops in one embodiment are crimped or deformed portions 194 in the cover tube 192. The crimped portions interacting with the stop projections of the blade shaft act as a positive stop as the inside dimension of the cover tube is narrower than the overall width of the stop projections on the blade shaft. A pull tube 193 coupled to the jaws to actuate and/or energize one or both jaws is disposed over the blade shaft and in one embodiment includes one or more slots to provide exposure or interaction of the stops of the blade shaft with the stops of the cover tube.

The stops ensure that if force is applied the cutter will not beyond a predetermined point. The cutter could be allowed to continue to move distally or proximally upon actuation and the distal or proximal end of the channel or portions thereof can halt further movement of the cutter. However, if further pressure or bias is applied to move the cutter distally or proximally, the contact with one or both jaws under pressure can damage or dull the cutter. The stop projections prevent such a condition. In one embodiment, the second stop projection prevents further movement of the cutter proximally and thus the spring biasing the cutter towards the proximal direction, the spring can hold the cutter in place. Thus, the cutter can be moved along tissue to cut tissue with the jaws opened or closed without movement of the blade shaft through movement of the instrument along or through tissue. Tissue pressed against the cutter is cut as the pressure or force of the spring along with the interaction of the stop projections holds the cutter in place.

In one embodiment, the jaws 22 include a stationary first jaw 202 and a movable second jaw 204 that moves relative to the first jaw. In one embodiment, both jaws may be movable or the first jaw movable and the second jaw stationary. The first jaw 202 is entirely conductive or includes conductive material. In one embodiment, the first jaw includes an electrode generally planar and covering or extending over an upper surface of the first jaw. The second jaw 204 includes first and second electrodes 205, 206 with an insulator between the electrodes. In one embodiment, the second electrode 206 is on an upper portion of the second jaw 204 distal from the first jaw 202 and the first electrode 205 is on a lower portion of the second jaw 204 proximate to the first jaw 202. The second jaw is pivotally connected to the first jaw or the shaft or other components connected to the first jaw. Through this pivot connection, the first jaw 202 in one embodiment is electrically connected to the second electrode 206 of the second jaw 204. The second electrode 206 is entirely conductive or includes conductive material and is generally shaped like the first jaw. The second electrode 206 in one embodiment is generally hemispherical. The first jaw 202 in one embodiment is generally hemispherical. Tissue however clamped or captured between the first and second jaws 202, 204 is positioned between the first electrode and the second jaw. As such, the second electrode 206 in one embodiment does not participate or is not involved electrically in the cutting or sealing of tissue grasped or captured between the first and second jaws 202, 204. The second electrode 206 when electrically added or switched in, in one embodiment, is involved in the cutting and/or sealing of tissue outside or at least with tissue in contact with the second electrode. In one embodiment, this configuration makes it unnecessary to electrically insulate the first jaw and second jaw and in one embodiment may be commonly connected via a jaw pin. As such, manufacturing is eased and multiple or excessive electrical connections are reduced.

For example, in one embodiment, the first electrode 205 of the second jaw 204 and the first jaw 202 are electrically connected to assume a first and second polarity such that tissue positioned between (clamped or not clamped) and in contact with the first electrode 205 and the first jaw 202 can be sealed when a user activates a sealing operation. As such, RF energy appropriate for sealing tissue is transmitted through the tissue between the first electrode 205 and first jaw 202 to seal the tissue. In one embodiment, a movable cutting blade can be activated by the user to cut the tissue between the first electrode 205 and first jaw 202. The cutting blade in one embodiment is electrically conductive and energized such that RF energy appropriate for cutting tissue is transmitted between the cutting blade and the first jaw 202, second jaw 204, or both. In one embodiment, the cutting blade is stationary. The cutting blade in one embodiment may be relatively blunt or sharp that may or may not depend on the electrical connectivity of the blade. There may also be multiple blades and some or all may be electrically conductive or connected. The cutting blade in one embodiment is positioned generally perpendicular to the first jaw 202 and/or can traverse through the length or a portion thereof of the first or second jaws.

In one embodiment, tissue outside of the first and second jaws 202, 204 can be cut and/or coagulated. In one embodiment, the second electrode 206 and first jaw 202 can be energized to coagulate tissue between the contact point or area of the second electrode to tissue and the contact point or area with the first jaw. As such, jaws are positioned on its side in its opened or closed position and can be dragged or slid across the tissue to coagulate and/or cut tissue. Also, the jaws can be positioned with its front or tips of the jaws (opened or closed) contacting tissue and dragged or slid across the tissue to coagulate and/or cut tissue. In one embodiment, the first electrode 205 of the second jaw 204 and the second electrode 206 of the second jaw 204 are electrically connected to assume a first and second polarity such that tissue positioned between or in contact with the first and second electrodes to be cut and coagulate when a user activates a respective cut or coagulate operation.

As such, RF energy appropriate for cutting or coagulating tissue is transmitted through the tissue between the first electrode 205 and second electrode 206 to respectively cut, coagulate, fuse or weld the tissue. As such, second jaw 204 can be dragged, pushed or slid across tissue to coagulate and/or cut tissue. In one embodiment, cutting or coagulation is only allowed when jaws 202, 204 are partially or fully spaced from each other. In one embodiment, a switch or sensor is activated to indicate the spaced relationship or the lack thereof between the jaws to allow activation of cut or coagulation of the tissue.

In one embodiment, the first electrode 205 extends along an outer portion of the distal end or tip of the second jaw 204. The first and second electrodes 205, 206 can be energized to cut, coagulate, fuse or weld tissue between or in contact with the electrodes. By limiting the first electrode to a specific area or arrangement relative to the second electrode, the focus or applicable energizing area can be limited to the specified portion of the first electrode and the second electrode 205, 206. In one embodiment, the second electrode 206 can also be similarly arranged to extend along a limited portion of the second jaw 204. In the illustrated embodiment, an insulator 207 disposed adjacent the first electrode 205 limits the focus area of the first electrode. In one embodiment, the size, shape and/or orientation of the first electrode, the second electrode and/or an additional provided electrode is limited to provide the appropriate or desired focus area. The first electrode extending along the outer periphery of the second jaw is positioned generally horizontal relative to the second jaw and in one embodiment may be relatively blunt. The orientation, size and location of the first electrode can vary based on the desired surgical operation and there may be additional electrodes similarly positioned.

The first electrode 205, the first jaw 202 and/or the second electrode 206 in one embodiment is a contiguous or monolithic electrode with a contiguous or monolithic seal surface. In one embodiment, the monolithic seal surface includes spaced or interrupted portions to provide a plurality of seal paths or surfaces. For example, first electrode 205 includes first and second seal paths 217a, 217b. The first and second seal paths surround and are adjacent to the blade or cut channel of the jaw through which the blade or cut electrode is situated or traverses therethrough. In the illustrated embodiment, the monolithic seal surface also includes spaces or cavities 215a, 215b and a third and a fourth seal path 219a, 219b positioned near but spaced from the first and second seal paths. The first and second seal paths in one embodiment are inner paths relative to the outer paths of the third and fourth seal paths. The multiple interrupted or spaced seal paths provide redundant seal areas or portions of the tissue being sealed separated by a portion of the tissue not electrically or otherwise treated or manipulated by the jaws. As such, by situating a separated or unaffected tissue between seal paths, the overall tissue seal is enhanced and thermal spread along the tissue and effects thereof are reduced. In the illustrated embodiment, tissue between the first seal path and the fourth seal path remains unaffected by energy being transmitted to the electrode while tissue along the first and third seal paths is electrically sealed. Likewise, tissue between the second seal path and the fourth seal path is electrically sealed and the tissue between the paths or within or along the cavities remains unaffected. Tissue along the cavities is also not compressed or mechanically manipulated as compared to the tissue along the seal paths.

In one embodiment, the first electrode 205 can be activated by the user to cut, coagulate, fuse or weld tissue in contact with or between the first electrode 205 and the first jaw 202 and/or the second electrode 206. In one embodiment, the second electrode 206 and the first jaw 202 share a common electrical contact and/or common polarity such that RF energy can be transmitted between the first electrode 205 and the first jaw 202 and/or between the first electrode 205, the second electrode 206 and the first jaw 202.

In one embodiment, when the jaws are not fully opened or closed, i.e., in a state or condition between being open and being closed, tissue positioned between the jaws 202, 204 can be fused. Automatic disruption of RF energy in one embodiment however is not used, is not activated or is deactivated as the appropriate conditions for automatic disruption of RF energy is not satisfied or cannot be assured. Cutting can also be prevented (mechanically and/or electrically). Identification of the intermediate state in one embodiment is determined based on the activation or lack thereof of a switch and/or sensor within the instrument adjacent the trigger and/or jaws or detecting the position of the trigger or the jaws relative to each other.

In accordance with various embodiments, electrosurgical RF energy to cut and/or coagulate tissue in a bipolar fashion utilizes both an active and a return electrode and can be used for example in general and gynecological laparoscopic procedures. In such configurations, the desired surgical effect (e.g., cut, coagulate, etc.) is based upon the current density ratio between the electrodes, the electrode geometry and the current and voltage supplied to the electrodes. In one embodiment, cutting tissue utilizes a voltage output greater than 200 V and coagulating utilizes a voltage below 200V. Current density is measured as the (Delivered Current)/(Electrode Surface Area). As such, the active and return electrodes can be assessed by the following current density ratio: Active Electrode/Return Electrode=(Large Current Density)/(Small Current Density). It should be appreciated that an electrode can assume or switch between roles as an active electrode or a return electrode relative to another electrode based on current density, electrode geometry and/or current and voltage supplied to the electrodes. Generally, the active and the return electrodes are electrically insulated or isolated from each other.

Various electrode configurations of the jaws of the electrosurgical instrument in accordance with various embodiment of the invention are shown in FIGS. 30-38. In various embodiments, at least one or only one electrode is located on one of the jaws. For example, the electrode in one embodiment is located on the top jaw and horizontally oriented relative to the jaw. It should be appreciated that the electrode could be on an opposite jaw than illustrated and the top and bottom jaws are relative to each other. As such, referral to a top jaw can equally be a referral to a bottom jaw as well as movable jaw to stationary jaw.

Figure 30A:
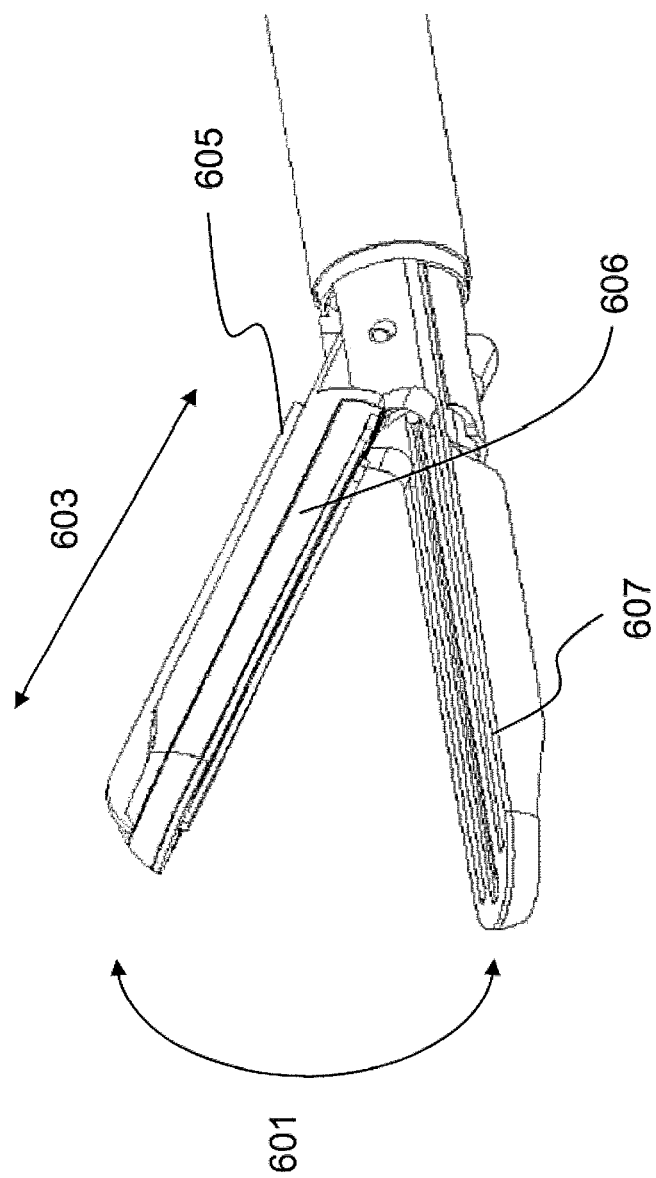
FIGS. 30A-B are perspective views of jaws of an electrosurgical instrument in accordance with various embodiments of the invention.
Figure 30B:
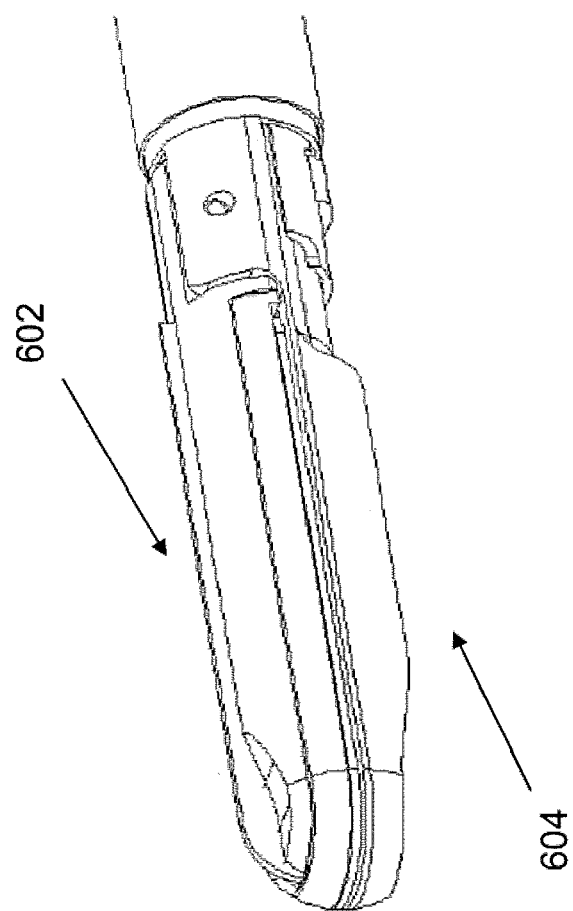

In FIGS. 30A-B, a movable jaw 602 includes an outer vertical electrode 605. This electrode configuration provides cutting at the tip of an articulating or movable jaw and/or along the length of the jaw. In one embodiment, the cutting follows in an articulating manner and/or path relative to the shaft and actuator of the instrument. For example, tissue can be cut as the top jaw opens as the electrode on the jaw is parallel or in-line with the path that the jaw travels (e.g., path 601 and/or 603 (in both or one direction)). In the illustrated embodiment, the electrode 605 in conjunction with a larger conductive portion 606 surrounding the electrode on the jaw or a second electrode 607 conduct RF energy there between to effectuate the cutting path.

In one embodiment, a stationary jaw 704 includes an outer vertical electrode 705 as shown in FIG. 31. This electrode configuration provides cutting at the tip of a stationary jaw 704 and/or along the length of the outer portion of the jaw. The electrode 705 in one embodiment operates in conjunction with either an inner or an outer electrode acting as another electrode to conduct RF energy there between. In one embodiment, a movable jaw 702 does not include an electrode or is otherwise insulated or isolated from the electrode 705. In operation, a surgeon can manipulate the direction or path of the cut directly through the manipulation of the actuator as the jaw remains stationary relative to the shaft of the instrument.

Figure 32:
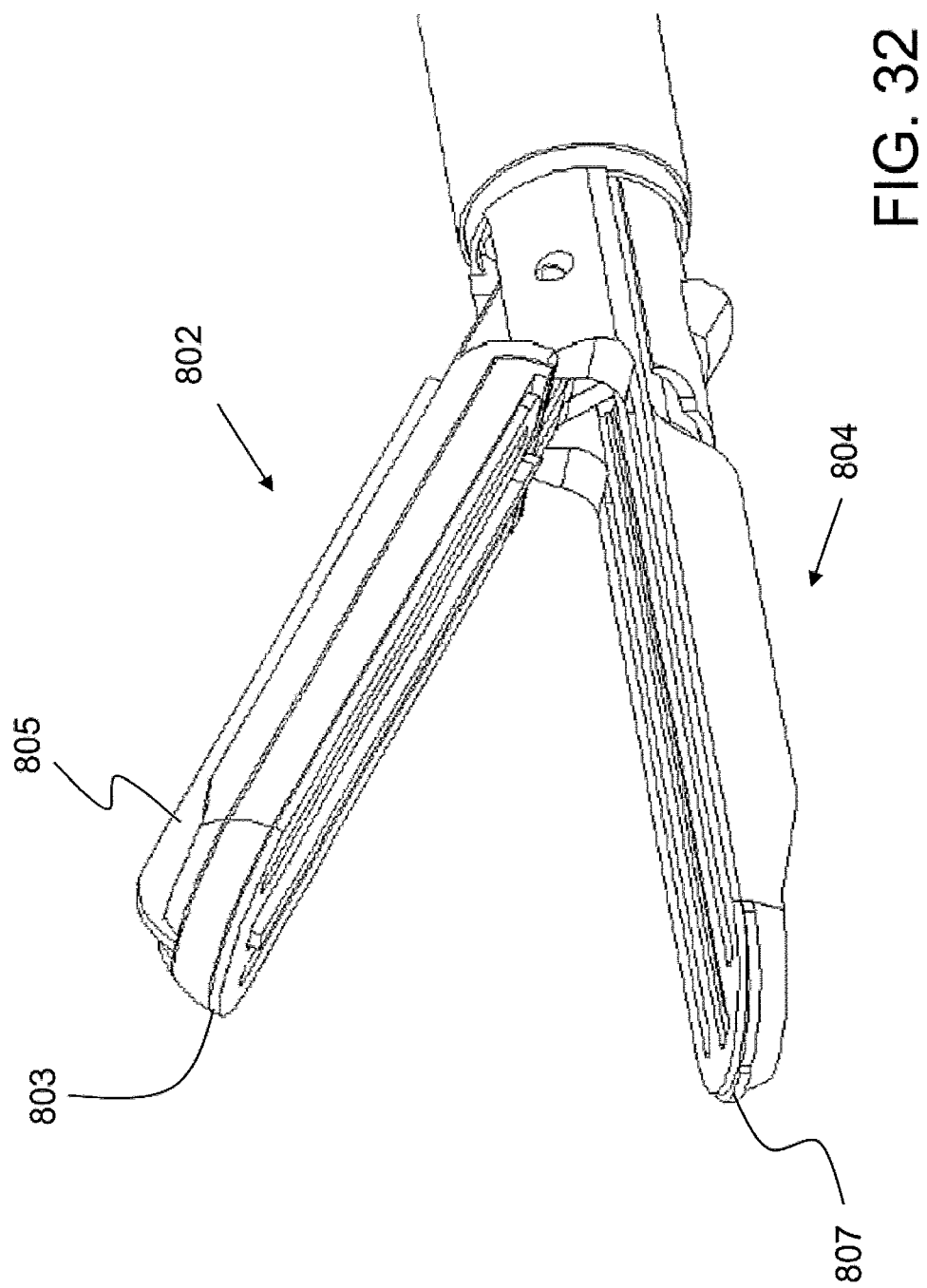
FIG. 32 is a perspective view of jaws of an electrosurgical instrument in accordance with various embodiments of the invention.

Referring now to FIG. 32, in one embodiment, one of the jaws 802 includes a horizontal electrode 803 and a vertical electrode 805. This electrode configuration provides directed energy delivery based on the position of the jaws relative to each other. The configuration also makes it unnecessary to electrically insulate the top jaw actuating member from the lower jaw. While the jaws are closed, the horizontal electrode 807 on the lower jaw 804 can be used to dissect tissue utilizing the lower jaw 804 as a return electrode. While the jaws are open, the vertical electrode 805 can cut tissue at the tip of the top jaw 802 as well as along the length of the top jaw in an articulating manner relative to the shaft and hand-piece of the instrument. Tissue can be cut as the top jaw opens because the active electrode is parallel to the path that the top jaw travels. The active electrode utilizes the top jaw actuating member as the return electrode. The orientation of both electrodes can be switched, e.g., vertical to horizontal and horizontal to vertical, to achieve similar effects.

Figure 33:
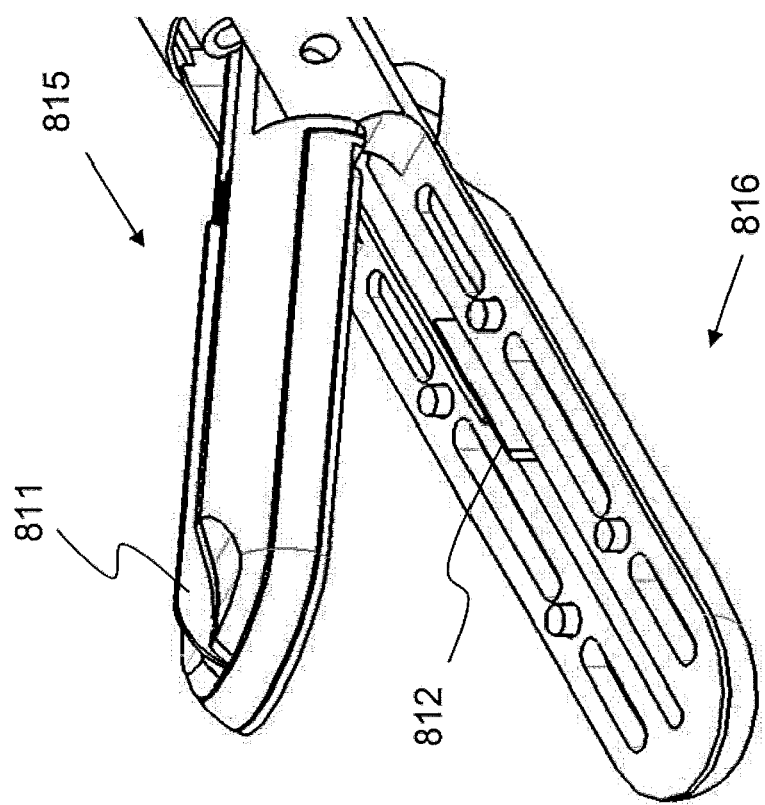
FIG. 33 is a perspective view of jaws of an electrosurgical instrument in accordance with various embodiments of the invention.
Figure 36A:
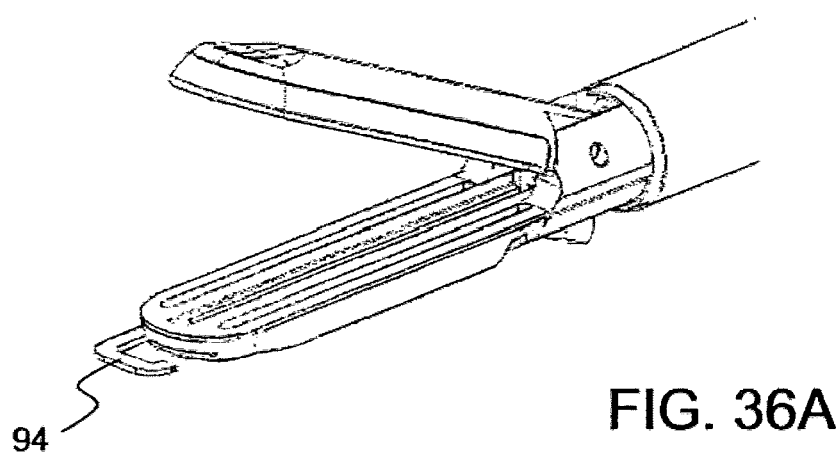
FIGS. 36A-D are perspective views of jaws of an electrosurgical instrument in accordance with various embodiments of the invention.
Figure 36B:
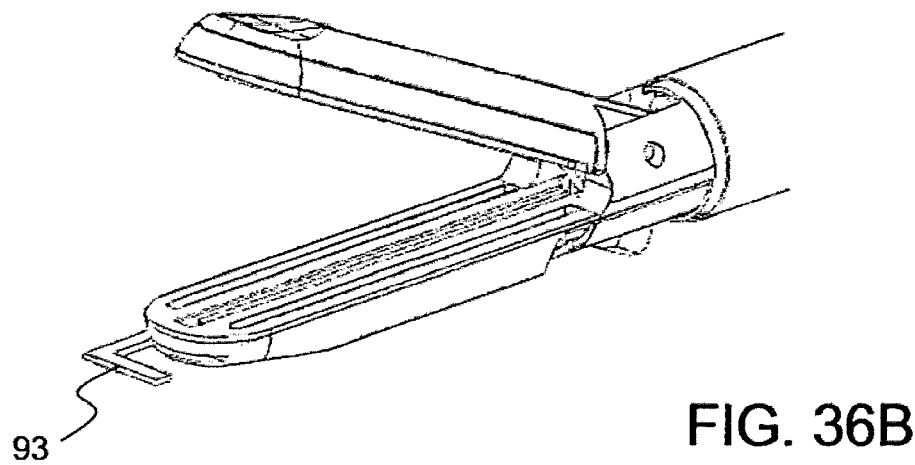
Figure 36C:
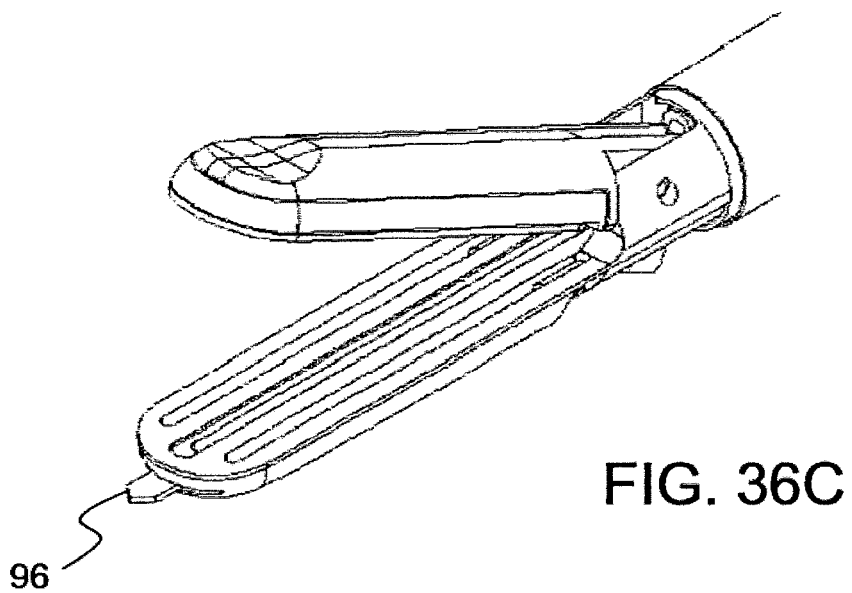
Figure 36D:
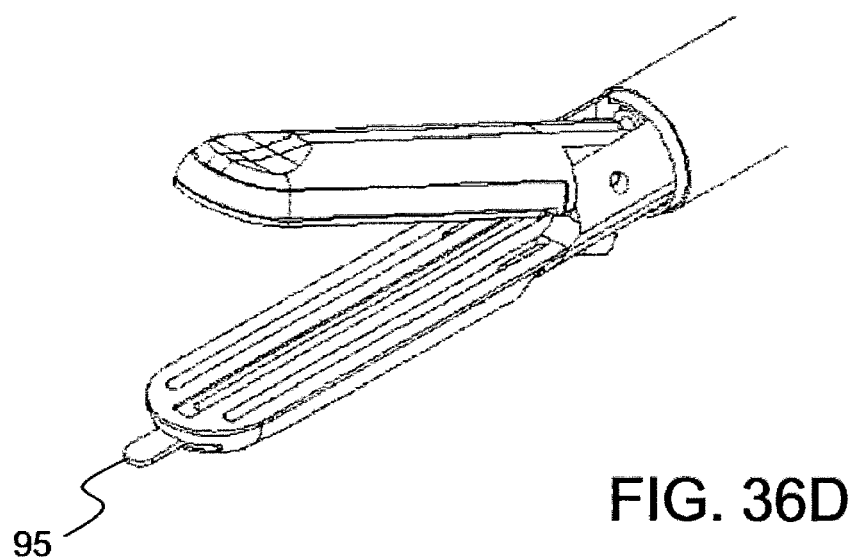

In one embodiment, an electrosurgical cutting electrode 811 can be used to dissect tissue as shown in FIG. 33. A mechanical cutting blade 812 is used to divide tissue captured in the jaws 815, 816 of the instrument along the length of the jaws of the instrument by activation of a lever located on the actuator of the instrument. It should be appreciated that the mechanical blade and electrical electrodes can be reversed. In one embodiment, a first cutting electrode 811 can be used to dissect tissue. A second cutting electrode 812 is used to divide tissue captured in the jaws of the device by using the lower jaw 816 as a return electrode. This second electrode can travel along the length of the jaws of the instrument by activation of a lever located on the actuator of the instrument.

In various embodiments, electrodes (and portions in which they are attached) can be used to probe and/or manipulate tissue in a physical manner when not electrically active. In various embodiments, retractable electrodes provide an atraumatic jaw assembly for tissue contact and for movement through trocar seals. In one embodiment, retraction of a cutting electrode into the body of either jaws of the instrument can facilitate the removing or cleaning eschar that has built up on the electrode.

In one embodiment, the retraction of an electrode 91 can be actuated through movement in relation to the trigger of the actuator (FIGS. 34A-B). For example, the retraction would occur in relation to the movement of the jaws. Such an actuation can indicate which position the electrode can be used to cut tissue. In one embodiment, when the electrode is extended, the electrode can be activated and when retracted inactive. The placement of the retractable electrode can be on either or both jaws. In one embodiment, the retraction of the electrode 91 can occur through a lever or similar actuator separate from the trigger or actuator (FIGS. 35A-B). As such, the electrode can be extended and retracted independently of the jaw position. The electrode can also be activated independently and in an extended position.

The retractable electrodes described above and as shown in FIGS. 36A-D can be rounded 95, pointed 96, L-Hook shaped 93, or J-Hook shaped 94. In various embodiments in which the electrodes are L-Hook shaped, J-Hook shaped or similarly shaped and retractable, such electrodes can be used to capture tissue between the jaws of the instrument and/or the hook portion of the electrode.

In one embodiment, an electrode on one of the jaws may be separated or be two adjacent electrodes (e.g., a distal electrode and a proximal electrode). Each electrode can be energized simultaneously or individually. Also, one of the electrodes can allow a different tissue type to be treated differently from the other electrode (e.g., one cuts and the other coagulates, one treats one type of tissue and the other is used for another type of tissue). The separate electrodes can also provide a comparison of tissue type or phase monitoring to ensure proper treatment (e.g., cut, coagulation, etc.) of the tissue or multiple tissue types in contact with the separate electrodes. The other jaw or other portions of the same jaw in one embodiment can act as an electrode in which RF energy is exchanged between the electrodes and the jaws.

Referring now to FIGS. 20-29, electrosurgical instruments are connectable to an electrosurgical unit through a coupler 50 in accordance with various embodiments of the invention. The coupler 50 includes a plug 502 attached to a cable 501 attached to and extending from the connecting instrument. Attached to the plug 502 is a connector 503 which is connectable to the electrosurgical unit. In one embodiment, the plug 502 is not connectable to the electrosurgical unit without the connector 503.

In one embodiment, the plug 502 is removably attached to a connector 503 that is directly connectable to an electrosurgical unit. The connector 503 provides a conduit such that radio frequency energy is supplied from the electrosurgical unit through the cable to the instrument. Additionally, communication back to the electrosurgical unit is transmitted through the cable and connector from the instrument. For example, the instrument via switches or actuation of the handle or trigger transmits signals or closes circuits to ensure RF energy is delivered as requested by the instrument.

The connector 503 in one embodiment includes memory circuitry 503b' and a pin arrangement 503b''. The pin arrangement 503b'' is specifically arranged to couple to a corresponding pin arrangement 501d of the cable 501 associated with the electrosurgical instrument. On the other end of the cable, contacts 501a, 501b, and 501c are arranged to connect to corresponding contact points for switches, indicators and/or sensors as appropriate for the associated electrosurgical instrument. Accordingly, the pin arrangements can vary to couple the cable to the connector 503 and the contacts 501a, 501b, 501c, 501e, and 501f can vary to couple the cable to the corresponding electrosurgical instrument.

The memory circuitry in one embodiment includes instrument or tool data that outlines the operation of the instrument in conjunction with the electrosurgical unit. The tool data in one embodiment is transmitted from the chip to the electrosurgical unit. The unit in analysis of the tool data recognizes or identifies the electrosurgical instrument to which the connector is attached thereto. Additionally, the tool data includes script information that describes the operational aspects of the attached electrosurgical instrument. For example, the script information can include a total number of electrodes on the electrosurgical instrument and the state or condition in which one or more of the electrodes are utilized or software to be transferred to an electrosurgical unit upon successful electrical connection of the instrument to the electrosurgical unit. The tool data can also include data regarding various electrosurgical procedures to be performed by the instrument and corresponding energy level ranges and durations for these procedures, data regarding electrode configuration of an instrument, and/or data regarding switching between electrodes to perform different the electrosurgical procedures. Similarly, customized data, e.g., settings preferred by a particular surgeon or a surgical procedure to be performed, can also be included in the tool data and utilized for example to set the electrosurgical unit in a mode or particular configuration preferred by the surgeon, e.g., a particular power setting or the user interface's appearance or control.

In one embodiment, the electrosurgical unit has limited capabilities to supply or not supply RF energy. The electrosurgical unit can also incrementally increase or decrease the amount or intensity of the supply of RF energy. However, the control or regulation of the RF energy is not included or incorporated with the electrosurgical unit but instead is located on the memory circuitry as script information. The script information provides the control data that directs the supply of radiofrequency energy such that when a button or switch is activated by the user, RF energy is directed to corresponding electrodes as indicated in the control data. Similarly, the control data also includes information to identify and recognize the button being activated. After initial handshaking between the electrosurgical instrument and the unit when an instrument is connected to the unit, the script information is transferred to the electrosurgical unit. In one embodiment, subsequent or further access or requests to deliver the script information to the unit is not provided or permitted to prevent reuse of the connector 503.

The connector in one embodiment is non-sterile and the cable and the electrosurgical instrument to which the cable is connected are sterile. It should be noted that the non-sterile characteristic of the connector is not typically used in the other electrosurgical systems. However, due to the electrical components, e.g., the memory circuitry, within the connector typical sterilization of the connector is not readily available or usable. Accordingly, embedding or otherwise including such components with an electrosurgical instrument that must be sterile is typically not provided. However, by providing a separate and attachable connector the electrosurgical systems can be customized and/or configured while the sterilization concerns are overcome.

In one embodiment, the connector 503 allows the electrosurgical unit to be customizable and/or configurable to adjust or accommodate various electrosurgical instruments that are connectable to the electrosurgical unit. Accordingly, as an electrosurgical instrument changes or improves over time and/or surgical procedures or operational procedures change, the electrosurgical unit can be supplied the latest or most recent information from the connector specifically tailored or addressed to the electrosurgical instrument attached thereto. Therefore, changes to instrument or tool profiles and periodic tool updates can be rapidly made without downtime to electrosurgical units, as the software for instrument operation can reside with the electrosurgical instrument itself, rather than the electrosurgical unit. Accordingly, updates can be made during instrument production and thereby avoiding the potentially expensive and time prohibited activity of removing or replacing the electrosurgical unit from for example hospital operating rooms to perform updates to the unit.

The connector 503 also ensures a proper connection between an electrosurgical instrument and the electrosurgical unit. In one embodiment, script information stored in the connector is tailored only for the accompanying electrosurgical instrument and no other instrument. For example, if user connects a vessel sealer to the provided connector, the script information stored in the memory circuitry only includes information for that particular vessel sealer. Thus, if a user does connect the same connector to a different instrument, such as an electrosurgical scalpel, (mechanical and electrical features aside that prevent such attachment), the script information to recognize and/or supply power to such an instrument is not available to the electrosurgical unit. As such, even if a user activates the scalpel, the electrosurgical unit without any script information about such an instrument will not supply RF energy to the instrument. In this example, the script information provided is for a vessel sealer. Utilizing this script information the electrosurgical unit is also able to identify that the attached device is not a vessel sealer and in particular not the appropriate instrument for the provided script information. This in one embodiment can also be recognized by initial handshaking of an attached instrument and the electrosurgical unit, the script information thereby also providing a layer of insurance for proper instrument usage.

The connector 503 in one embodiment also provides a uniform configuration for the connection to the electrosurgical unit on one side or end and the plug of the electrosurgical instrument on the other end. The pin or recess arrangement 503a, 503b' provides an uniform and expected mating or coupling to corresponding pin or recess arrangements on the instrument ports of the electrosurgical unit. Similarly, the plug 501d includes a recess or pin arrangement that couples to the corresponding pin or recess arrangement 503b" of the connector 503. Covers 502a, 502b and 503c cover or enclose the associated components of the plug 502 or connector 503. Accordingly, the connector 503 provides a uniform mechanical connection between the electrosurgical unit and the associated electrosurgical instrument. Therefore, manufacturing and operational use are facilitated. However, the circuitry provided with the connector 503 can provide a customized or non-uniform electrical connection between the unit and the instrument and/or script information to the unit for the instrument. Therefore, upgrade flexibility and instrument customization are enhanced.

It should be appreciated that there are various RF electrosurgical units that supply RF energy and likewise various electrosurgical instruments or tools that can connect to such electrosurgical units to receive the supplied RF energy which is operationally used in various surgical procedures. However, particular electrosurgical instruments require or optimally function when supplied RF energy within a particular specification or manner. In some cases, such instruments or electrosurgical units simply do not operate with the electrosurgical units or instruments, thereby leaving a surgical team to wonder if the instrument or electrosurgical unit is defective. As a result, operating devices are improperly discarded or surgical procedures delayed as the source of the problem is investigated and uncovered.

In other cases, the instruments or electrosurgical units do operate together in the sense that the instrument is supplied RF energy by the electrosurgical unit. However, the instrument or electrosurgical unit expecting a particular or specific application of such energy can result in damage to the devices or improper operation of the instrument, e.g., the instrument not cutting a tissue sufficiently or a vessel not sealing after the application of RF energy by the instrument. Therefore, in some cases, particular electrosurgical instruments should not be connected to particular RF electrosurgical units and vice versa.

Additionally, in particular cases, a specific operational quality and performance of an electrosurgical instrument or electrosurgical unit is expected by a surgical team for use in a particular surgical procedure. Such operational performance however results only when the specific electrosurgical instrument is utilized with the specific electrosurgical unit. Accordingly, this pairing of specialized devices is required to provide the expected operational quality and performance. Therefore, there is a need to ensure the proper connection between electrosurgical instruments and electrosurgical units to ensure operational quality and performance and to prevent unexpected and unintended operation failures or damage to the devices.

In one embodiment, systems and methods are provided to ensure the proper connection of specialized or specific electrosurgical instruments to the specialized or corresponding specific receptacles of an electrosurgical unit. Improper connection or connection with a non-specialized electrosurgical instrument with the specialized receptacles is thus prevented. As such, among other things, this ensures that only electrosurgical instruments of a specific quality and performance are used that match the specific quality and performance of the electrosurgical unit.

In one embodiment, the tool connector 503 mates with a tool connector receptacle 302 of a tool port of an electrosurgical unit. An embossment on the connector and an excavation or channel 303 on the tool receptacle ensures proper orientation upon instrument or tool insertion. The embossment on the connector and the excavation on the receptacle also ensures that proper or expected instruments are being plugged in the corresponding instrument port, e.g., DC port versus a dedicated instrument port (and vice versa). Upon insertion, a latching mechanism, in one embodiment, including latch arms on the instrument plug and corresponding latch shelves 301 on the receptacle locks the connection, resulting in an engagement of flat surfaced contact pads on the connector with a series of extending pins 304, e.g., spring-loaded pogo-pins, of the receptacle of the electrosurgical unit. In one embodiment, a series of pins extending from a receptacle of the electrosurgical unit are removably and electrically coupled to flat surface pads on the connector. As such, the flat surface pads do not include any mechanical connectors to interact or interlock the pins with the associated pad. Additionally, in one embodiment, the connector or plug does not include mechanical connections or interlocks to couple the pins from the receptacle to the connector. In the illustrated embodiment, the contact pads are recessed within individual cavities in the plug and the cavities do not interlock with the associated pins extending to contact the associated contact pad when the plug is inserted into the receptacle. In one embodiment, the receptacle also includes a switch 305 recessed within receptacle that is operatively activated by the plug and in particular an interlock pin or projection 504 extending from the plug and being inserted into the receptacle. In one embodiment, the receptacle is circular or similarly shaped along with the corresponding plug that reduces the overall surface or working area along the electrosurgical unit. In one embodiment, the pins extend from the plug or connector while flat surface pads are arrayed along the receptacle of the electrosurgical unit.

In various embodiments, on the other side of the tool connector plug contact pads are shown. In this view, a printed circuit board (PCB) with a circuitry housing an encrypted tool memory chip and a tool connector head that provides connection to the instrument are given. The tool connector head in various embodiments connects the instrument electrodes (up to five), functional instrument switches (cut, coag and fuse), instrument position switches (instrument fully open and instrument fully close), as well as a three-colored LEDs in the electrosurgical instrument to the electrosurgical unit. As such, the pin/receptacle assignment on the instrument receptacles corresponds to the pin/receptacle assignment on the tool connector plug.

In one embodiment, script-based or instrument-specific generator intelligence is stored in a non-volatile memory section of the memory chip in the tool connector that communicates with an electrosurgical unit. A script parser in a central processing unit (CPU) of the electrosurgical unit reads and processes tool script information such as, but not limited to, instrument authentication (ensuring original manufacturer use), single-use assurance, instrument expiration date, instrument recognition, user interface control (electrosurgical unit's display and/or tones), instrument interface settings (e.g., LEDs on instruments), electrode selection and electrosurgical unit settings (voltage and current) which can also be based on position of the jaw elements (fully open or fully clamped), time-out limits to de-activate power based on time, as well as tissue feedback-activated endpoints (e.g., fuse end point based on phase between voltage and current) and switch points (e.g., switching from coag to cut, fuse to cut, based for example on phase between voltage and current).

The memory chip in one embodiment is written by the electrosurgical unit CPU to store procedure-specific data such as, but not limited to, the serial number of the electrosurgical unit used, a time stamp of instrument connection, the number of instrument uses, the power setting used during each use, the tissue feedback data before, during and after a instrument use, the nature of the instrument use (cut, coag, fuse), the duration of the instrument use, the nature of the shut off point (auto stop, fault, manual stop, etc.), as well as the event and nature of any faults (instrument short, expired or unrecognized instrument, etc.).

An embodiment of a pin-assignment for the dedicated RF instrument receptacles provides pin contacts numbered 1 through 8 are reserved for to the tool memory circuitry, pins 9 through 17 for the instrument switches and LEDs (cut, coag, fuse, instrument open, instrument close, red, blue, green LED and return), and pins 18 through 22 for five instrument electrodes. In another embodiment a pin-assignment for the dedicated DC instrument receptacle provides pin contacts numbered 1 through 8 are reserved for to the memory circuitry, pins 9 through 17 for the instrument switches and LED (onl, on2, on3, instrument position 1, instrument position 2, red, blue, green LED and return), and pins 20 and 21 for provision of DC power.

Electrosurgical systems and processes in various embodiments apply monopolar or bipolar high-frequency electrical energy to a patient during surgery. Such systems and processes are particularly adapted for laparoscopic and endoscopic surgeries, where spatially limited access and visibility call for simple handling, and are used to fuse blood vessels and weld other biological tissue and in one aspect to cut, dissect and separate tissue/vessels. In particular embodiments, the systems and processes include the application of RF energy to mechanically compressed tissue to thereby fuse, weld, coagulate, seal or cut the tissue. In various embodiments, the determination of the end-point of the electrosurgical process is given by monitoring or identifying the phase shift of voltage and current during the process. In one embodiment, unlike impedance, the phase shift changes are more pronounced at times where the tissue desiccates and the fusion process completes, and hence offers a more sensitive control value than the impedance. Accordingly, the application of RF energy via an electrosurgical unit in conjunction with the measuring or monitoring of phase shift via an electrosurgical controller are provided to fuse, weld, coagulate, seal, cut or otherwise electrically modify or affect vessels and tissue in accordance with various embodiments of electrosurgical system.

In one embodiment, measurement of the dielectric properties of the tissue and control and feedback of the phase difference allows for a precise control and feedback mechanism for various tissue types, regardless of the tissue size. For example, a controller of the electrosurgical unit is configured to determine the product of dielectric constant and conductivity, as well as the phase difference between the applied voltage and current to monitor and control the tissue electrosurgical process. In particular, control and feedback circuitry of the controller determines when the phase difference reaches a phase shift value determined by the results of dielectric and/or conductivity measurements. When such a threshold or derived threshold is reached, the electrosurgical process is terminated or another operation is commenced or condition activated. An indicator, e.g., visual or audible, is provided to signal the termination or state/operation change and in one aspect the controller restricts (completely, nearly completely or to a predetermined minimum) further delivery of electrical energy through the electrodes. In one embodiment, the electrosurgical instrument in conjunction with the controller thereby provides atraumatic contact to the connecting tissue and provides enough burst pressure, tensile strength, or breaking strength within the tissue.

In one embodiment, instead of the tissue quickly reaching a pre-determined phase (e.g., ranging from 40 to 60 degrees, depending on type of tissue), the measured phase shift approaches the cut-off threshold asymptotically. Such an asymptotic approach can require an extended amount of time to reach a final phase threshold. As such, instead of depending on the phase value to reach a definite value alone, additionally the derivate of the phase can be used to avoid asymptotic approaches to a finalized phase value. Additionally, the determined phase value can be overshot without being detected or before the processor is able to recognize that a final phase stop has been reached. As such, instead of solely relying on the phase value to reach a definite value alone, the derivate of the phase is also used.

As previously described and described throughout the application, the electrosurgical unit ultimately supplies RF energy to a connected electrosurgical instrument. The electrosurgical unit ensures that the supplied RF energy does not exceed specified parameters and detects faults or error conditions. In various embodiments, however, an electrosurgical instrument provides the commands or logic used to appropriately apply RF energy for a surgical procedure. An electrosurgical instrument includes memory having commands and parameters that dictate the operation of the instrument in conjunction with the electrosurgical unit. For example, in a simple case, the electrosurgical unit can supply the RF energy but the connected instrument decides how much energy is applied. The electrosurgical unit however does not allow the supply of RF energy to exceed a set threshold even if directed to by the connected instrument thereby providing a check or assurance against a faulty instrument or tool command.

Figure 37A:
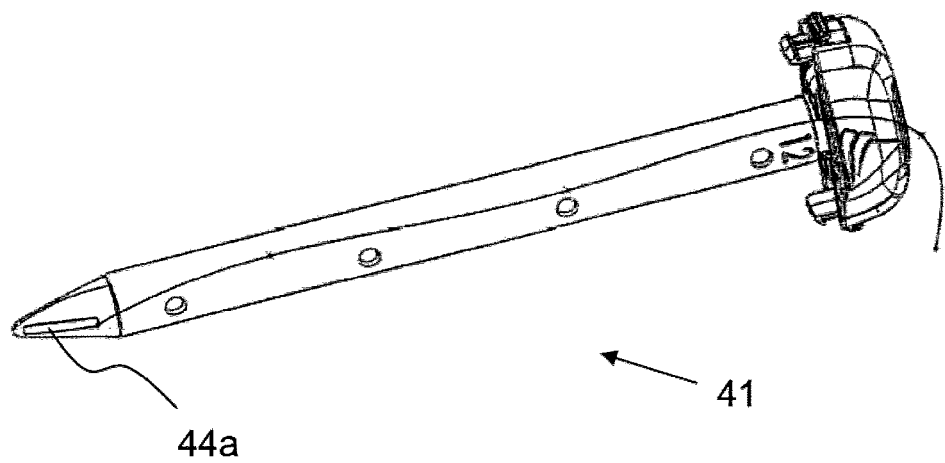
FIGS. 37A-B are perspective views of an electrosurgical instrument in accordance with various embodiments of the invention.
Figure 37B:
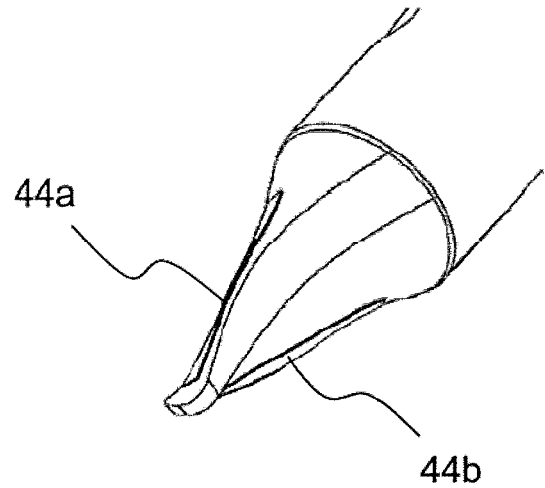

In accordance with various embodiments, continuous and/or periodically monitoring the phase value of the tissue being contacted can be correlated to a transition from one tissue condition or type to the next or from one tissue condition or type to no contact. In one illustrated embodiment, an obturator 41 includes two electrodes 44a, 44b used to monitor the phase of the tissue being contacted (FIGS. 37A-B). As the obturator is inserted into the abdominal cavity, the phase value can be used to indicate the point at which the tip of the obturator is inside or through the abdominal wall at which point the surgeon can begin insufflation. This entry point can be indicated with a visual, audible or tactile alert. It should be appreciated that an insufflation needle, a probe or similar instruments can likewise be configured as the obturator to ensure that a specific entry point or condition is identified as appropriate for a specific surgical procedure. Similar applications can also be applied to the placement of stents, ensuring proper contacts of grounding pads and the like. Additionally, utilizing phase value, tissue identification or condition can assist in replacing or removing the need for tactile feedback. For example, in robotic surgical operations and instruments used therein phase/tissue identification monitoring can remove the need to "feel" that tissue is being cut, sealed or grasped or to exert a particular pressure to perform such operations.

In various embodiments, continuous and/or periodically monitoring of the phase value of the tissue being treated can be correlated to either a change in tissue type or a change in the tissue properties due to delivery of energy. In one embodiment, based on the monitoring of the phase value of tissue, the output current and voltage to the instrument can be modified (e.g., increased or decreased based on the desired tissue effect (Cut, Coag, or Fuse)), electrodes can be activated or deactivated, and delivery of energy to the active accessory can begin or end.

Electrosurgical modality transitions based on the phase value of the tissue for electrosurgical instruments in accordance with various embodiments of the invention can be characterized as:
1. Coagulate to Cut
2. Coagulate to Cut to Coagulate (Automatic shut-off—RF energy shut off when a phase value is reached or exceeded)
3. Coagulate to Cut to Coagulate (User shut-off—RF energy shut off when the surgeon releases the delivery of energy)
4. Cut to Coagulate (Automatic shut-off)
5. Cut to Coagulate (User shut-off)

In one embodiment, when coming into contact with tissue of specific phase values, the modalities (Cut, Coag, and Fuse) of the active instrument could be rendered active or inactive. In another embodiment, when coming into contact with tissue of specific phase values, an instrument can automatically provide energy to the tissue (cut, coagulate, fuse, weld or any combination thereof and/or the above noted modalities) until a predetermined phase value is reached.

In one embodiment, a visual, audible, and/or tactile indication can be used to indicate a tissue type that the active instrument is in contact with and thereby the electrosurgical instrument can probe for a specific tissue type. When used in combination with multiple electrodes of the active electrosurgical instrument, combinations of tissue type could be indicated visually, audibly, and/or tactilely and specific electrodes can be activated to provide energy to a portion of the device as desired to perform a specific surgical operation and based on the specific tissue.

In one embodiment, in order to cut tissue using bipolar RF energy, the tissue being treated cannot be desiccated or dehydrated to a point in which the collagen seal is all that remains. At this point the "seal" is unable to conduct electricity in the manner necessary or safely cut the tissue utilizing bipolar energy delivery (e.g., tissue resistance is too high). Likewise, at this point, cutting the seal or the tissue around the seal utilizing a mechanical (non-energized) blade or cutting instrument can also be difficult due to for example the tissue calcifying. Therefore, when utilizing phase values to identify the transitions of "pre-cut" or "partial seal", the tissue can be coagulated to known phase value less than the predetermined phase value indicated for complete tissue coagulation. Subsequently, cutting is performed (either mechanically or electrically). After cutting, energy delivery can be continued until a predetermined phase values indicated for complete tissue sealing is reached.

It should be appreciated that the tissue to be cut should have minimal thermal damage or desiccation to ensure that the tissue is still conductive to be electrically cut. In one embodiment, the electrosurgical instrument provides that about 1-2 mm of lateral thermal damage outside of the jaws of the device at a phase shift of 45°. The spacing between the coagulating electrodes electrosurgical instrument is about 0.040" or 1 mm such that at a phase shift beyond 45° the tissue is desiccated too much to be cut effectively. As such, in one embodiment, the larger the spacing between electrodes, the higher a pre-cut transition point or condition can be set and a lower pre-cut transition supports closer electrode spacing. The lower pre-cut transition represents the phase value in which less coagulation occurs versus complete tissue coagulation. Additionally, applying RF energy, e.g., voltage faster or at a high or steep rate, is provided to support closer electrodes as the pre-cut transition is lower than a pre-cut transition with larger spacing between electrodes. Likewise, applying RF energy at a slower or less steep rate can be provided for larger spaced electrodes. Additionally, with the tissue being enclosed in between jaws, tissue within the confines of the jaw subjected to higher temperatures than on the outside edges of the jaw. As such, tissue less confined or subject to lower temperatures can have reduced thermal damage and thereby a higher pre-cut transition point can be used.

Figure 40:
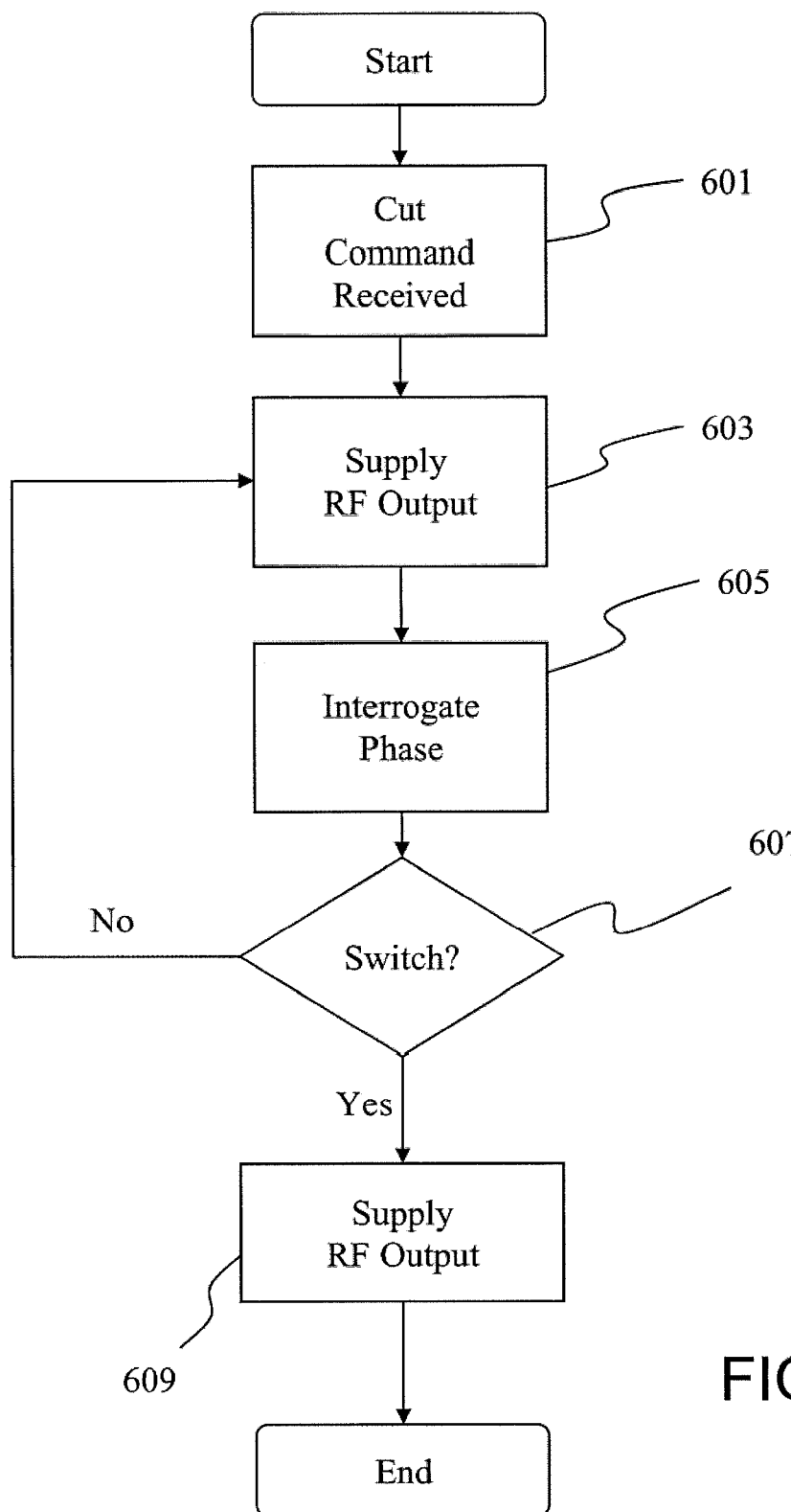
FIG. 40 is a flow chart illustrating a pre-cut process for an electrosurgical instrument in accordance with various embodiments of the invention.
Figure 41:
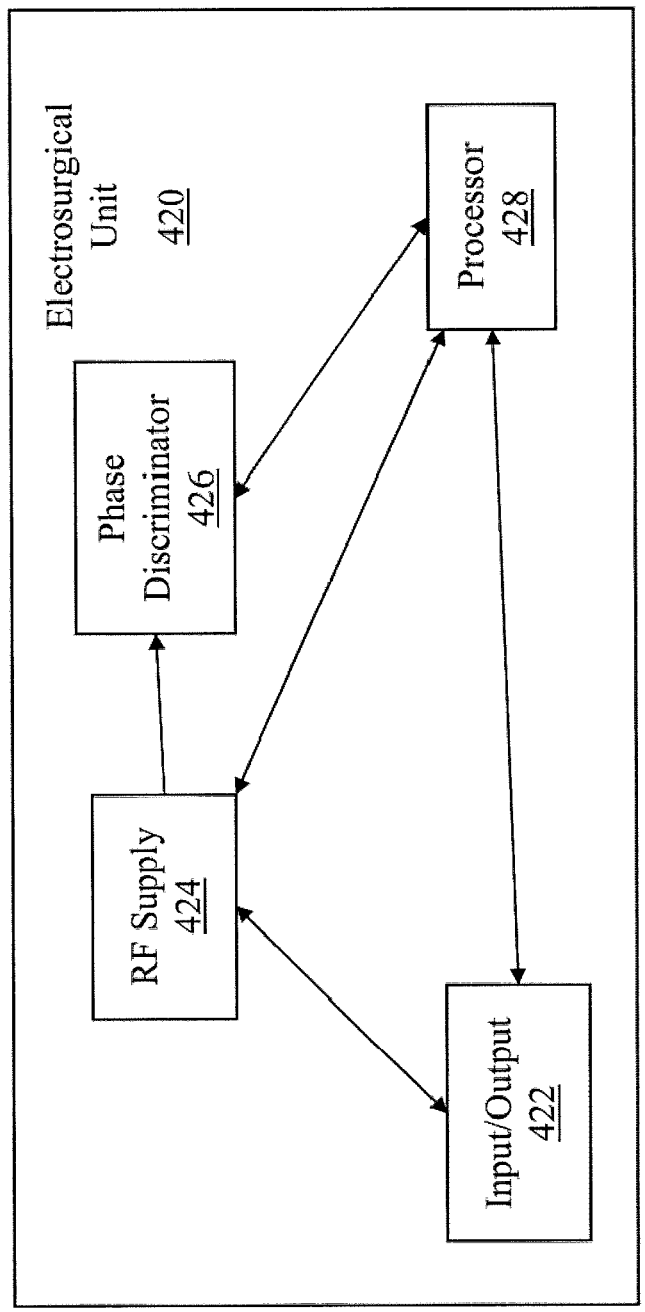
FIG. 41 is a block diagram of an electrosurgical unit in accordance with various embodiments of the invention.
Figure 42:
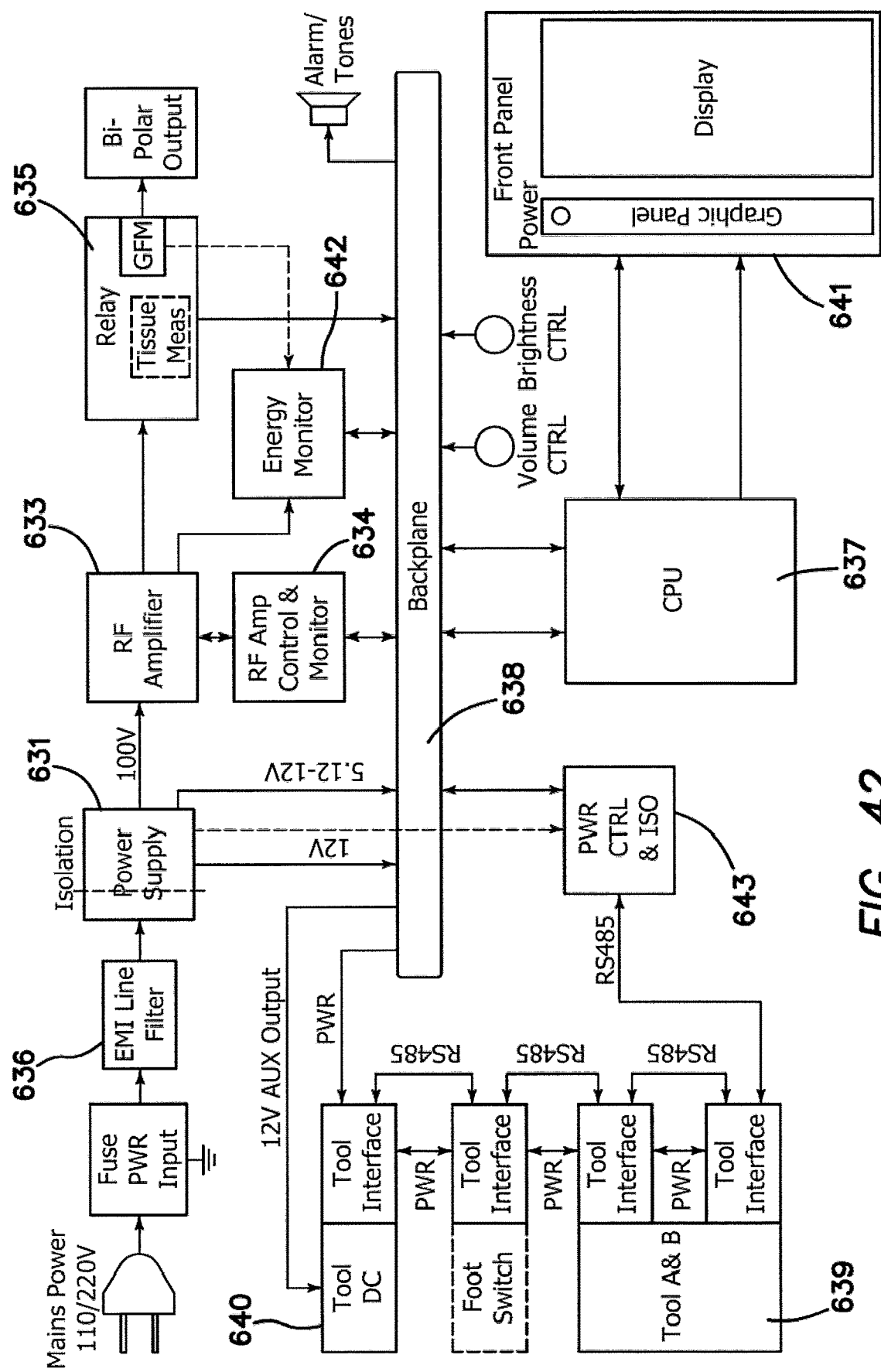
FIG. 42 is semi-schematic diagram of an electrosurgical unit in accordance with various embodiments of the invention.

Referring to FIGS. 40-42, in one embodiment, a pre-cut process is shown which initially starts for example by the receipt of a cut command (601) from the activation of a button or switch on the actuator. The activation of the cut button is communicated or recognized by the electrosurgical unit coupled to the electrosurgical instrument. In one embodiment, a processor within the electrosurgical unit instructs or initiates the output or supply of RF energy (603) to the electrosurgical instrument. However, the RF energy supplied is not energy sufficient to cut tissue disposed at the jaws of the electrosurgical instrument. Instead the RF energy supplied is used for coagulation which is lower than the energy sufficient to cut tissue. The processor monitors the phase between the current and voltage of the RF energy being supplied to the tissue (605). In one embodiment, through current and voltage monitoring circuitry and filters, the phase between the current and voltage of the RF energy is monitored. A comparison is made to a pre-cut phase condition or switch (607). In one embodiment, the pre-cut phase condition is a predetermined value or range of values that is specific for the particular electrosurgical instrument and the type of tissue indicated to be used or specifically used or to be treated by the instrument. In other embodiments, the pre-cut phase condition is determined dynamically based or relative to initial or periodic determinations about the tissue type via for example tissue permittivity and/or conductivity measurements to identify different predetermined values or range of values for a given tissue type. For example, an initial determination of a tissue type is used to lookup or compare to a table of values, e.g., pre-cut phase values, that are experimentally or otherwise predetermined to be the optimal or specific phase value to identify a pre-cut phase condition.

As previously described, the pre-cut phase condition is identified as a point or condition in which the tissue being applied with RF energy is nearly coagulation but less than or not up to the point of complete coagulation, e.g., near complete desiccated, dehydrated and/or calcification of the tissue. If it is not determined that the pre-cut phase switch is reached or exceeded, the process continues as the RF energy continues to be supplied and the phase monitored. Once it is determined that the pre-cut phase condition has been met, cutting of the tissue then proceeds. In one embodiment, the processor commands or initiates the raising or initiation of the RF energy suitable for cutting tissue at the jaws of the electrosurgical instrument (609). In one embodiment, the application of RF energy to pre-cut and then cut tissue is quick such that the rate at which the electrosurgical unit reaches or provides the maximum output voltage is accelerated. If there is a long ramp-up cycle or step function for the voltage to follow, the tissue intended to be cut will be only coagulated. As such, by the time the electrosurgical unit reaches the cut voltage levels the tissue will be too dessicated to properly cut.

In one embodiment, the process continues as phase between applied current and voltage is measured and/or monitored to determine or ensure that the tissue is properly cut. Additionally, in one embodiment, after the tissue is cut, complete coagulation of the tissue can be performed or initiated as RF energy for coagulation is supplied again to the tissue and a determination is made that the tissue has been coagulated.

The tissue pre-cut and then cut is the same or nearly the same, but it should be noted that the tissue can refer to surrounding tissue first being coagulated to a pre-cut condition and tissue between the nearly coagulated tissue is then cut. The application of the coagulation RF energy and/or cut RF energy is also dependent on the electrodes supplying the associated RF energy. As such, the tissue affected can also be based on the location or application of the RF energy from the electrode locations to be pre-cut and then a cut using different sets of electrodes. For example, when a cut command is initiated, one or more electrodes can be energized to apply RF energy to coagulate tissue in contact with the one or more electrodes and once a pre-cut condition is reached, one or more different electrodes are energized to apply RF energy to cut tissue in contact with these different electrodes. Thus, in one embodiment, when a cut button is activated on the electrosurgical instrument, tissue in one area may be supplied RF energy for coagulation to a pre-cut condition and a different tissue in a different are may be subsequently supplied RF energy to cut the different tissue. In one embodiment, one or more electrodes are used in transmitting RF energy for coagulation and one or more electrodes different from the other electrode used for coagulation are used in transmitting RF energy for cutting. Additionally, one or more electrodes can be used as a common or shared electrode utilized to accommodate both the transmission of RF energy for coagulation and cutting.

In one embodiment, an electrosurgical unit 420 can comprise input/output circuitry 422, RF supply circuitry 424, a phase discriminator 426 and a processor 428. One or more circuitry may be incorporated into an associated circuitry. For example, the RF supply circuitry may be included with the input/output circuitry and vice versa. The input/output circuitry receives and transmits RF energy from the RF supply circuitry and out of the electrosurgical unit and to a connected electrosurgical instrument (not shown). The input/output circuitry also receives tool data and/or tissue data from the electrosurgical instrument and/or through a connector therebetween. In one embodiment, the phase discriminator calculates a phase difference between the applied voltage and current from the RF supply circuitry. In one embodiment, the applied voltage and current are rectified and compared or combined, e.g., through an XOR logic gate, to generate a pulse width modulated signal. The duty cycle of the generated signal mirrors or represents the phase difference between the applied voltage and current. The determined phase difference is then supplied to a processor that compares to a predetermined phase threshold based on a particular tissue in contact with the electrosurgical instrument. In one embodiment, the processor provides the above described process of determining a pre-cut condition to completing a cut.

In one embodiment, an electrosurgical generator includes an RF amplifier 633, RF amplifier control and monitor 634, energy monitor 642 and relay and tissue measurement 635. The electrosurgical generator is coupled to a 120 Hz Voltage main input. The main input is isolated with a low leakage isolation transformer of a power supply 631. The power supply provides operational voltages for the control processor 637 and the RF amplifier 633. Additionally, the power supply includes two 50 VDC output modules connected in series to provide a total output of 100 VDC and 8 Amps. RF power is generated by the RF amplifier, e.g., a switched mode low impedance RF generator that produces the RF output voltage. In one embodiment, a 500 peak cut voltage for cutting and 7 Amp current for coagulation/fusing is generated.

Fusing tissue in one embodiment involves applying RF current to a relatively large piece of tissue. Because of the potentially large tool contact area tissue impedance is very low. Accordingly, to deliver an effective amount of RF power, the current capability of the RF amplifier is large. As such, where a typical generator might be capable of 2 to 3 amps of current, the RF amplifier of the generator can supply more than 5 Amps RMS into low impedance loads. This results in rapid tissue fusion with minimal damage to adjacent tissue.

The RF amplifier circuitry has redundant voltage and current monitoring. One set of voltage and current sensors are connected to the RF amplifier control and monitor and are used for servo control. The voltage and current can also be read by the processor 637 using an analog to digital converter (ADC) located on the RF amplifier control and monitor. The RF amplifier control and monitor also has an analog multiplier, which calculates power by computing the product of the voltage and current. The RF amplifier control and monitor uses the average value of voltage and current and does not include a phase angle and thus is actually calculating Volt Amps Reactive (VAR) rather than actual power. A second set of voltage and current sensors are also connected to the energy monitor 642. The signals are connected to an ADC for redundant monitoring of the voltage and current. The processor multiplies the voltage and current readings to verity that power output does not exceed 400 Watts. The energy monitor has monitoring circuits that are completely independent of the RF amplifier control and monitor. This includes the ADC, which has an independent voltage reference.

The RF amplifier in one embodiment is a switching class D push pull circuitry. As such, the amplifier can generate large RF voltages into a high tissue impedance, as well as large RF currents into low tissue impedance. The output level of the RF amplifier is controlled by Pulse Width Modulation (PWM). This high voltage PWM output signal is turned into a sine wave by a low pass filter on the RF amplifier. The output of the filter is the coagulation output of the RF amplifier. The output is also stepped up in voltage by an output transformer resulting in the cut output of the RF amplifier. Only one output is connected to the control servo on the RF amplifier control and monitor at a time and only one output is selected for use at a time.

Coupled to the RF amplifier is the RF amplifier control and monitor 634. The RF amplifier control and monitor 634 in one embodiment receives voltage and current set points, which are input by the user through a user interface, to set the output level of the RF amplifier. The user sets points are translated into the operating levels by digital to analog converters of the RF amplifier control and monitor. The user sets points are translated into the operating levels by digital to analog converters of the RF amplifier control and monitor. The set points in one embodiment include a maximum voltage output, maximum current output, maximum power output, and a phase stop. The servo circuit of the RF amplifier control and monitor controls the RF output based on the three set points. The servo circuit as such controls the output voltage of the RF amplifier so that the voltage, current, and power set points are not exceeded. For example, the output of the ESG is restricted to be less than 400 watts. The individual voltage and current set point can be set to exceed 400 watts depending on the tissue impedance. The power servo however limits the power output to less than 400 watts.

The RF output voltage and current are regulated by a feedback control system. The output voltage and current are compared to set point values and the output voltage is adjusted to maintain the commanded output. The RF output is limited to 400 Watts. Two tool connections are supported by using relays 635 to multiplex the RF output and control signals. The EMI line filter 636 limits the RF leakage current by the use of an RF isolation transformer and coupling capacitors.

The cut and coagulation output voltages of the RF amplifier are connected to the relay and tissue measurement circuitry 635. The relay and tissue measurement circuitry in one embodiment contains a relay matrix, which steers the RF amplifiers output to one of the three output ports of the electrosurgical unit. The relay matrix also selects the configuration of the tool electrodes. The RF output is always switched off before relays are switched to prevent damage to the relay contacts. To mitigate against stuck relays steering RF to an idle output port each output port has a leakage current sensor. The sensor looks for unbalanced RF currents, such as a current leaving one tool port and returning through another tool port. The current sensors on are located on the Relay PCB, and the detectors and ADC are on the energy monitor PCB. The CPU monitors the ADC for leakage currents. Any fault detected results in an alarm condition that turns off RF power.

The relay and tissue measurement circuitry also contains a low voltage network analyzer circuit used to measure tool impedance before RF power is turned on. The circuit measures impedance and tissue phase angle and in one embodiment using a 10V signal operating at 100 Hz. The processor 637 uses the impedance measurement to see if the tool is short-circuited. If a Tool A or B output is shorted the system warns the user and will not turn on RF power. The RF amplifier is fully protected against short circuits. Depending on the servo settings the system can operate normally into a short circuit, and not cause a fault condition. In one embodiment, initial impedance and/or phase measurements can determine if the jaws are open and/or having no tissue in contact with the jaws and/or the jaws are dirty, e.g., excessive or interfering eschar build-up.

Voltage and current feedback is provided using isolation transformers to insure low leakage current. The processor 637 computes the power output of the RF amplifier and compares it to the power set point, which in one embodiment is input by the user. The processor also monitors the phase lag or difference between current and voltage. Additionally, in one embodiment, the processor matches the different phase settings, which depend on tissue types to the monitored phase difference. The processor as such measures a phase shift of tissue prior to any application of RF energy. As will be described in greater detail below, the phase measurement is proportional to tissue permeability and conductivity that uniquely identifies the tissue type. Once the tissue type is identified, the phase angle associated with an end point determination of that tissue type can be determined. The generator in one embodiment has three RF output ports (Tool A, Tool B and generic bipolar). The tool A and B ports 639 are used to connect smart tools, while the generic bipolar port 640 supports standard electro surgical tools. Audible tones are produced when the RF output is active or an alarm condition exists.

The hand and foot controls are also isolated to limit leakage current. The control processor checks the inputs for valid selections before enabling the RF output. When two control inputs from the switches are simultaneously activated the RF output is turned off and an alarm is generated. Digital to analog converters are used to translate control outputs into signals useable by the Analog Servo Control. The control set points are output voltage and current. The analog to digital converter is used to process the analog phase angle measurement. Voltage RMS, current RMS, and power RMS information from the controller is also converted into a form usable for presentation to the user. The digital I/O bus interface 638 provides digital communication between the user, controller and hand/foot switches. Isolation circuitry is used to eliminate a possible leakage path from the electrosurgical generator. It also provides communication between the user and the generator though a data channel protocol.

In one embodiment, there are four tool Interface circuits in the unit. These circuits are used to electrically isolate the user input switches from mains power inside the system. The four tool interface circuits are identical and have an on board microprocessor to read the user switch inputs as well as the tool crypto memory and script memories. The switch closure resistance is measured with an ADC to eliminate a contaminated switch contact being read as a closure. Switch closures below 300 Ohms are valid, while any reading above 1000 Ohms is open. Readings between 300 and 1000 Ohms are considered to be faulty inputs.

The four tool interface circuits communicate with the processor using an RS485 network. Each tool interface circuit has jumpers to select its address and location in the unit. The RS485 interface is isolated to eliminate any potential leakage current paths. One tool interface circuit is connected to each of the Tool A and B ports. A third tool interface circuit is connected to the DC output port, and the fourth circuit is connected to the rear panel foot switch inputs. The processor is the network master and each of the four circuits is a network slave. The processor polls each circuit for input. The tool interface circuitry can only reply to commands. This makes the network deterministic and prevents any kind of dead lock. Each Tool Interface circuit is connected to a System OK logic signal. If a system error is detected by a Tool Interface circuit, this signal is asserted. The processor monitors this signal and indicates a fault. This signal also has a hardware connection to the RF amplifier control and monitor and will disable the RF amplifier when asserted. A system error could be two input switches activated at the same time, or a loss of communication with the processor. The Tool A & B ports as well as the DC port have a micro switch that detects when a tool is plugged into the receptacle. Until this switch is depressed the Tool Interface circuit front panel connections are configured off to prevent any leakage current flowing from front panel connections. Once the switch is depressed the Tool Interface allows the processor to initiate reads and writes to the tool crypto memory and script memory. Once a tool is detected a window opens in the user interface display showing the type of tool connected and status. The generic bipolar port supports legacy tools, which do not have any configuration memory. The tissue measurement circuitry is used to monitor the bipolar connection contacts. When a bipolar tool is connected the tool capacitance is detected and the processor opens the bipolar tool window on the user interface display and shows status for the bipolar tool. The DC port is used to interface with 12 Volt DC powered custom surgical tools. When a tool is plugged into this port a window opens in the user interface display showing the type of tool connected and status. When the DC tool script commands power on, the processor closes a relay on the Power Control and Isolation circuitry 643 turning on the isolated 12 Volt tool power.

The power control and isolation circuitry 643 has two other features. It controls the 100 Volt power supply that drives the RF amplifier. This power supply is turned on by a relay controlled from the RF amplifier control and monitor. The processor commands this power supply on via the RF amplifier control and monitor. If the RF amplifier control and monitor is reset or detects a fault condition, the relay will not operate leaving the 100 Volt power supply off Also located on the power control and isolation circuitry is a RS485 isolation circuit that adds an extra layer of isolation.

The front panel interface circuitry 641 is used to connect the front panel control switches and LCD display to the processor. The front panel interface circuitry also contains a microprocessor, which is powered by an isolated standby power supply, which is on whenever the main power switch is on. When the front panel power switch is pressed, the microprocessor uses a relay on the Power Control and Isolation circuitry to turn on the main logic power supply. When the button is pressed to turn power off, the microprocessor signals a power off request to the processor. When the processor is ready for power to be turned off it signals the microprocessor to turn off power. The power control relay is then opened, turning off the main power supply.

In one embodiment, the generator accepts only single switch input commands. With no RF active, e.g., RF energy applied, multiple switch closures, either from a footswitch, tool, or a combination of footswitch and tool are ignored. With RF active, dual closures shall cause an alarm and RF shall be terminated. The footswitch in one embodiment includes momentary switches providing activation of the application of RF energy. The switches for example when manipulated initiates activation of the RF energy for coagulation, for cutting and/or sequenced coagulation or cutting. A two-position pushbutton on the foot pedal switch allows toggling between different tools. The active port is indicated on the display of the generator and an LED on the hand tool.

In one embodiment, all RF activation results in a RF ON Tone. Activation tone volume is adjustable, between 40 dBA (minimum) and 65 dB (maximum) with a rear panel mounted control knob. The volume control however does not affect audio volume for alarms. Also, in one embodiment, a universal input power supply is coupled to the generator and operates over the input voltage and frequency range without the use of switches or settings. A programming port in one embodiment is used to download code to the generator and is used to upload operational data.

The generator in one embodiment provides output power has a 12V DC at 3 Amps. Examples of such tools that use DC power are, but are not limited to, a suction/irrigation pump, stapler, and a morcellator (tool for dividing into small pieces and removing, such as a tumor, etc.). The DC connector has intuitive one-way connection. Similar to the other tool receptacles, a non-sterile electronic chip module is imparted into the connector of the appropriate DC-powered hand tool by a one-time, one-way locking mechanism. Tool-specific engravings on both the connector and chip module ensure that the chip module fits only to the type of tool for which it has been programmed. The chip connector allows tool recognition and the storage of data on tool utilization. The DC connector is also configured to prevent improper insertion. The generator is also configured to recognize the attached DC-powered tool. The generator reads configuration data from the tool connector, allowing tool recognition and the storage of tool utilization data.

In one embodiment, phase measurement is a relative measurement between two sinusoidal signals. One signal is used as a reference, and the phase shift is measured relative to that reference. Since the signals are time varying, the measurement cannot be done instantaneously. The signals must be monitored long enough so that difference between them can be determined. Typically the time difference between two know points (sine wave cross through zero) are measured to determine the phase angle. In the case of the phase controller, the device makes the output sine wave with a precise crystal controlled clock. That exact same clock is use to read the input samples with the analog to digital converter. In this way the output of the phased controller is exactly in phase with the input of the phase controller. The phase controller in one embodiment compares the input sine wave signal to a reference sine wave to determine the amount of phase shift.

The phase controller does this comparison using a mathematical process known as a Discreet Fourier Transform (DFT). In this particular case 1024 samples of the input signal are correlated point by point with both a sine function, and a cosine function. By convention the cosine part is called real, and the sine part is called imaginary. If the input signal has no phase shift the result of the DFT is 100% real. If the input signal has a 90-degree phase shift the result of the DFT is 100% imaginary. If the result of the DFT has both a real and imaginary component, the phase angle can be calculated as the arctangent of ratio of the imaginary and real values.

It should be appreciated that the phase angle calculation is independent of units of the real and imaginary numbers. Only the ratio matters. The phase results of the phase controller are also independent of gain and no calculation of impedance is made in the process of calculating the phase angle. By performing a DFT, the phase controller encodes the phase measurement as a pair of numbers.

In accordance with various embodiments, precise knowledge of the phase endpoint prior to energy delivery allows for tighter control, and for delivery of more current than other electrosurgical units (7A, 400 W). In accordance with various embodiments, the memory capability of the instrument key portion of each instrument connector allows the reading and writing of information between the electrosurgical unit and the instrument key or connector. The information can include recording treatment data (energy profile, tissue types, etc.) or data to prevent device reuse. In one embodiment, the use-before-date (UBD), number of uses, device serial number and expiration after first use values are encrypted to prevent reprocessing and reuse of the instrument key. In one example, to assist in managing inventory, the information may include the serial number of the electrosurgical unit that can be retrieved and stored into the memory upon connection of the instrument to the unit. The serial number or similar information is then used in parallel with lot and sales data to locate the electrosurgical unit and/or track electrosurgical unit's movements. Likewise, locators or trackers using GPS, RFID, IP addresses, Cellular Triangulation can be incorporated in the instruments and/or electrosurgical unit to locate and track electrosurgical units or instruments.

In one embodiment, the information may include metrics such as recording tissue types encountered during a procedure and/or tracking performance of an instrument or electrosurgical unit (how often used, number of procedures, and so on). Pre-customized surgeon settings can also be included in which the device output parameters (e.g., voltage, current, and power) stored in the connector or instrument key and read into the electrosurgical unit when connected. The specific settings can be programmed or stored prior to shipment of the instrument/connector. Diagnostic information on instrument/electrosurgical unit can also be included. For example, calibration and output verification information can be stored on the electrosurgical unit and then downloaded to the instrument key when connected. In one embodiment, software upgrades can also be delivered via the memory and the instrument ports on the electrosurgical unit.

In one embodiment, the electrosurgical generator or unit can automatically sense or identify a standard bipolar instrument insertion/connection. In one embodiment, the electrosurgical unit can compensate for or enhance a standard bipolar instrument to phase monitor and/or identify tissue or its condition. For example, a tissue measurement circuitry could be included in the electrosurgical unit or as an intermediate connector between the instrument and electrosurgical unit. The circuitry and/or program could include phase monitoring and/or tissue type or condition identification functionality. The tissue measurement circuitry in one embodiment can include a phase measurement adjustment circuit or program to account for impedance in the circuitry and cables that run between the tissue and the tool port. The circuitry may also include temperature correction as an actual change in phase value due to the instrument may be less than potential changes due to temperature fluctuations.

Using the phase difference between voltage and current as a control value in a fusion or welding process, instead of the impedance, can be further shown when characterizing the tissue electrically. When considering vessels and tissue to be a time-dependant ohmic resistor R and capacitor C in parallel (both of which depend on the tissue size and type) the phase difference can be obtained with $$R = \frac{\rho \cdot d}{A},$$

where R is the ohmic resistance, $\rho$ the specific resistance, A the area, and d the thickness of the fused tissue, $$X_C = \frac{1}{\omega \cdot C},$$

where $X_C$ is the capacitive impedance, $\omega_0$ the frequency, and C the capacity of the tissue, and $$C = \frac{\varepsilon \cdot \varepsilon_0 \cdot A}{d},$$

where $\varepsilon$ and $\varepsilon_0$ are the relative and absolute permittivity.

The phase difference $\varphi$ can then be expressed as $$\varphi = \arctan\left(\frac{X_C}{R}\right) = \arctan\left[(\omega \cdot \varepsilon \cdot \varepsilon_0 \cdot \rho)^{-1}\right],$$

where $\rho$ is equal to (1/conductivity).

As such, the difference between monitoring the phase difference $\varphi$ as opposed to the (ohmic) resistance R is that $\varphi$ depends on the applied frequency $\omega$ and material properties only (namely, the dielectric constant $\varepsilon$ and the conductivity), but not on tissue dimensions (namely the compressed tissue area A and tissue thickness d). Furthermore, the relative change in phase difference is much larger at the end of the fusion process than the change in tissue resistance, allowing for easier and more precise measurement.

In addition, with measurement of the initial dielectric properties of the tissue (dielectric constant $\varepsilon$ and conductivity) at a certain frequency, the type of tissue can be determined. The dielectric properties for various types of biological tissue, arranged by increasing values of the product of dielectric constant $\varepsilon$ and conductivity) are given in FIG. 30 at a frequency of 350 kHz (which is in the frequency range of a typical electrosurgical generator). By measurement of the product of dielectric constant $\varepsilon$ and conductivity of the tissue (which are material characteristics and independent of tissue dimensions) before the actual tissue fusion or welding process, the phase shift required to adequately fuse or seal the specific biological tissue can be determined. The phase shift required to reliably fuse or seal the respective type of tissue is measured as function of the product of dielectric constant $\varepsilon$ and conductivity of the tissue. Additionally, endpoint determination can be represented as a function of an initial phase reading of the tissue determination and likewise end point determination can be represented as a function of tissue properties (conductivity times relative permittivity).

As a result, (a) measurement of the dielectric properties of the tissue and (b) control and feedback of the phase difference allows for a precise control and feedback mechanism for various tissue types, regardless of the tissue size and allows employing standard electrosurgical power supplies (which individually run in a very close range of frequencies). It should be noted that however that specific frequency of the tissue properties measurement is performed can be the same or different from the specific frequency of the phase. If the tissue measurement is based on the driving frequency of the generator, and various generators are used (all of which run in a close range of frequencies) though, the end points will be different. Hence, for such a case, it can be desirable to (1) use an external measurement signal (which is at the same frequency), or (b) utilize a stand-alone generator.

As such, the controller is configured to determine the product of dielectric constant and conductivity, as well as the phase difference between the applied voltage and current to monitor and control the tissue fusion or welding process. In particular, control and feedback circuitry of the controller determines when the phase difference reaches the phase shift value determined by the result of the dielectric and conductivity measurements. When this threshold is reached, the fusion or welding process is terminated. An indicator, e.g., visual or audible, is provided to signal the termination and in one aspect the controller restricts (completely, nearly completely or to a predetermined minimum) further delivery of electrical energy through the electrodes. As such, the tool generating the seal, weld or connection of the tissue provides atraumatic contact to the connecting tissue and provides enough burst pressure, tensile strength, or breaking strength within the tissue.

Figures 1, 39A:
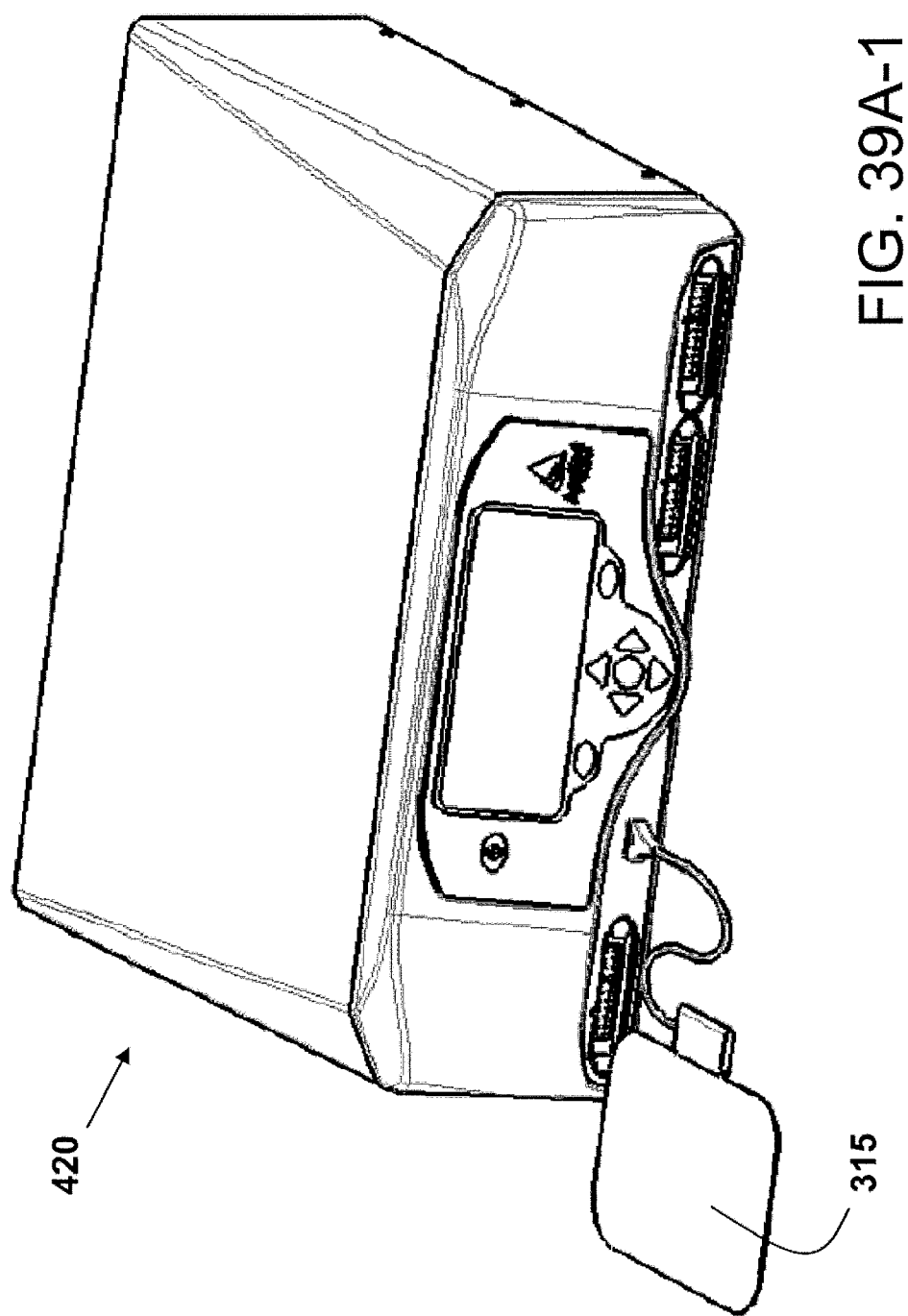
Figures 2, 39A:
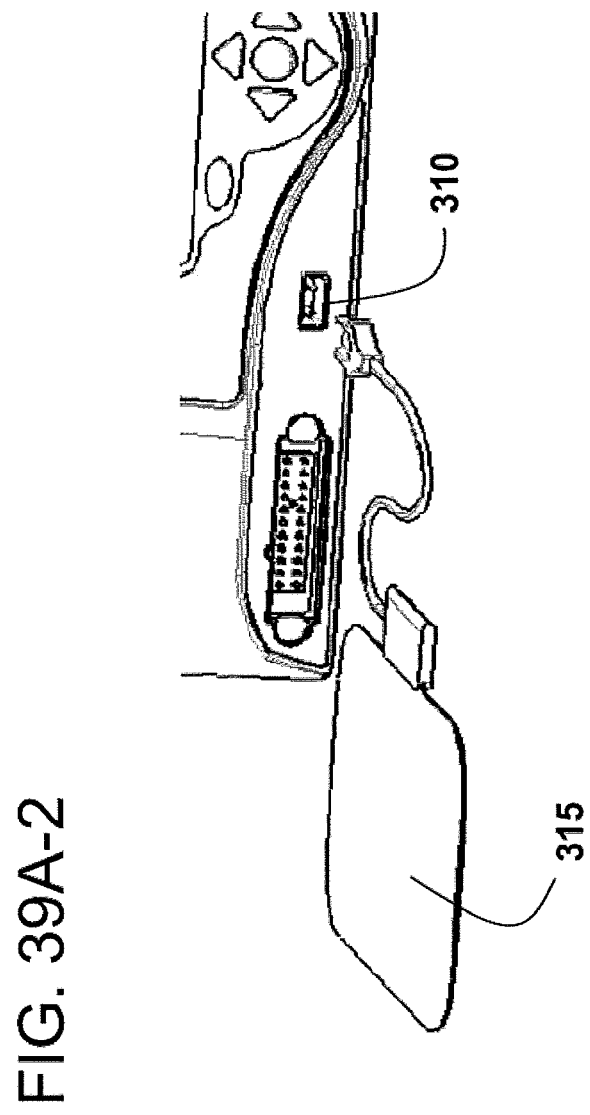
Figure 39B:
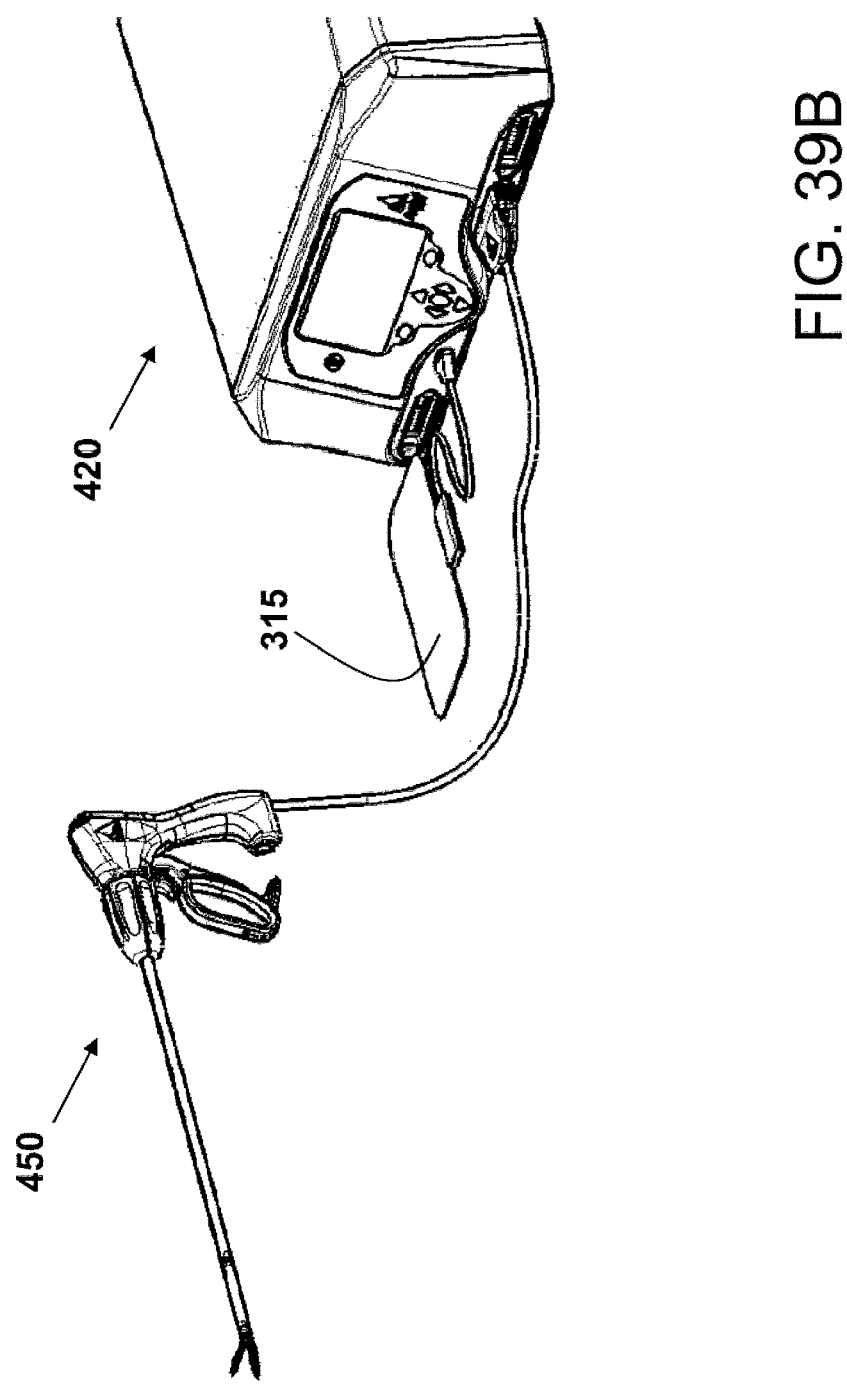
FIG. 39B is a perspective view of a monopolar pad, a monopolar and/or bipolar electrosurgical instrument, and an electrosurgical unit in accordance with various embodiments of the invention.

In one embodiment, a bipolar/monopolar single connector plug is provided to allow the connection of monopolar instruments to the electrosurgical unit. In one embodiment, the connector includes a grounding pad port 310 that acts as another electrode (e.g., a $6^{th}$ electrode (F)) that the electrosurgical unit 420 turns on and off through internal relays in the electrosurgical unit (FIGS. 38-39). Based on the programming of the relay/electrode configuration or pattern on the instruments (e.g., stored in memory of the connector), an electrosurgical instrument 450 can cut and coagulate in either a bipolar manner, monopolar manner of both. In one embodiment, in bipolar mode, the electrosurgical unit 420 utilizes two or more electrodes, e.g., electrodes designated "B" and "C", to create active and return paths and in monopolar mode, the electrosurgical unit utilizes one or more of the electrodes as active, e.g., electrodes designated "A" through "E", and only an electrode where the grounding pad 315 would be designated or used as the return only electrode 310, e.g., electrode designated "F". In one embodiment, switches internally or externally on the electrosurgical instrument, the connector and/or the port can be used to identify or notify the electrosurgical unit that a monopolar operation is being used. Additionally, in one embodiment phase measurements of applied RF energy can be used to identify if the monopolar pad is removed, not providing sufficient contact with the patient and/or electrical conductivity to the electrosurgical instrument.

Further examples of the electrosurgical unit, instruments and connections there between and operations and/or functionalities thereof are described in U.S. patent application Ser. No. 12/416,668, filed Apr. 1, 2009, entitled "Electrosurgical System"; U.S. patent application Ser. No. 12/416,751, filed Apr. 1, 2009, entitled "Electrosurgical System"; U.S. patent application Ser. No. 12/416,695, filed Apr. 1, 2009, entitled "Electrosurgical System"; U.S. patent application Ser. No. 12/416,765, filed Apr. 1, 2009, entitled "Electrosurgical System"; and U.S. patent application Ser. No. 12/416,128, filed Mar. 31, 2009, entitled "Electrosurgical System"; the entire disclosures of which are hereby incorporated by reference as if set in full herein.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the following claims.

The invention claimed is:

1. An electrosurgical system comprising
an electrosurgical instrument comprising:
an elongate shaft having a proximal end, a distal end and a longitudinal axis extending from the proximal end to the distal end;
a first jaw connected to the elongate shaft, aligned with the longitudinal axis of the elongate shaft and being stationary relative to the elongate shaft, the first jaw having a cut channel extending lengthwise along and through the first jaw, and the first jaw comprising a monolithic seal surface surrounding the cut channel;
a second jaw coupled to the elongate shaft, the second jaw comprising a first electrode, a second electrode and an insulator positioned between the first and second electrodes, the second electrode being on an upper portion of the second jaw and distal from the first jaw, and the first electrode being on a lower portion of the second jaw proximate to the first jaw; and
a cutting blade connected to a blade shaft disposed within the elongate shaft, the cutting blade arranged to fit within the cut channel of the first jaw, the blade shaft comprising a distal stop and a proximal stop, the distal stop arranged to interact with a first corresponding stop disposed along the elongate shaft and arranged to prevent distal movement of the blade shaft beyond a distal interaction point of the first corresponding stop of the elongate shaft interacting with the distal stop of the blade shaft when the blade shaft is moved distally and the proximal stop arranged to interact with a second corresponding stop disposed along the elongate shaft and arranged to prevent proximal movement of the blade shaft beyond a proximal interaction point of the second corresponding stop of the elongate shaft interacting with the proximal stop of the blade shaft when the blade shaft is moved proximally;
and an electrosurgical generator arranged to supply radiofrequency (RF) energy to the electrosurgical instrument removably coupled to the electrosurgical generator; wherein the generator is arranged to determine a phase value of the supplied RF energy between the first electrode and the first jaw and to determine when the determined phase value of the supplied RF energy equals or exceeds a predetermined phase value; wherein the generator, after determining the determined phase value of the supplied RF energy equals or has exceeded the predetermined phase value, is arranged to supply RF energy between the first jaw and the cutting blade instead of the first electrode and the first jaw; wherein the generator is arranged to determine a phase value of the supplied RF energy between the first jaw and the cutting blade to determine when the determined phase value of the supplied RF energy equals or exceeds a second predetermined phase value; wherein the generator, after determining the determined phase value of the supplied RF energy equals or has exceeded the second predetermined phase value, is arranged to supply RF energy between the first electrode and the first jaw; and wherein the generator is arranged to not determine when the determined phase value of the supplied RF energy equals or exceeds a predetermined phase value when the first and second jaws are in the intermediate state.

2. The system of claim 1 wherein the generator is arranged to supply RF energy between the first jaw and the second electrode to coagulate tissue in front of the second jaw and tissue on at least one side of the second jaw.

3. The system of claim 2 wherein the second electrode and the first jaw share a common electrical contact in that the generator supplies RF energy between the first electrode and the first jaw and between the first electrode, the second electrode and the first jaw.

4. The system of claim 3 between the open and closed position, wherein the intermediate state comprises a position of the first and second jaws between an open position and a closed position, the first electrode and the first jaw are electrically connected to assume a first and second polarity with the first and second jaws being in the intermediate state in that tissue positioned between and in contact with the first electrode and the first jaw are fused when a fusing operation is activated and cutting by the cutting blade is prevented.

5. The system of claim 4 wherein the instrument further comprises an actuator connected to the elongate shaft, the actuator further comprises a blade trigger, a stationary handle and a movable trigger, the blade trigger being connected to the blade shaft and the movable trigger being movable towards the stationary handle to close the first and second jaws and movable away from the stationary handle to open the first and second jaws.

6. The system of claim 5 wherein the instrument further comprises a spring connected to the blade shaft and biasing the blade shaft proximally and wherein the proximal stop and the second corresponding stop are arranged to prevent the spring from pulling the cutting blade proximally beyond the proximal interaction point and the spring, the proximal stop and the second corresponding stop arranged to hold the cutting blade stationary at the proximal interaction point.

7. The system of claim 6 wherein the elongate shaft comprises a cover tube and the first and second corresponding stops are deformed portions on the cover tube, the deformed portions interacting with the distal and proximal stops of the blade shaft.

8. The system of claim 7 wherein the instrument further comprises:
  an internal switch disposed within the stationary handle and not externally accessible, the internal switch being activated by a flexible arm extending from the movable trigger and contacting with the internal switch when the movable trigger is moved towards the stationary handle; and
  at least one external switch disposed on the actuator and an electrical connection being established with the at least one external switch and the internal switch being both activated;
  wherein the generator is arranged to supply RF energy to the first jaw and the cutting blade with the internal switch being activated.

9. The system of claim 8 wherein the at least one external switch further comprises a first external switch to activate an electrosurgical activity and a second external switch to activate a different electrosurgical activity, the first external switch disposed proximate the second external switch.

10. The system of claim 9 wherein the generator, after the at least one external switch is deactivated, is arranged to supply RF energy between the first electrode and the first jaw instead of the cutting blade and the first jaw.

11. An electrosurgical system comprising:
  an electrosurgical instrument comprising:
    an elongate shaft having a proximal end, a distal end and a longitudinal axis extending from the proximal end to the distal end;
    a first jaw connected to the elongate shaft, aligned with the longitudinal axis of the elongate shaft and being stationary relative to the elongate shaft, the first jaw being conductive and having a cut channel extending lengthwise along and through the first jaw;
    a second jaw connected to the elongate shaft, the second jaw comprising a first electrode, a second electrode and a cut channel extending along the second jaw, the second electrode being shaped like the first jaw and being on an upper portion of the second jaw and distal from the first jaw, and the first electrode being on a lower portion of the second jaw proximate to the first jaw and extending along an outer portion of a distal end of the second jaw, the first electrode being parallel with the second electrode;
    a cutting blade connected to a blade shaft disposed within the elongate shaft, the cutting blade arranged to fit within and traverse through the cut channel of the first jaw and the cut channel of the second jaw, and the blade shaft having a plurality of stops arranged to limit movement of the blade shaft and the cutting blade; and
    an actuator connected to the elongate shaft, the actuator comprises a blade trigger, a stationary handle and a movable trigger, the movable trigger being movable towards the stationary handle to close the first and second jaws and movable away from the stationary handle to open the first and second jaws, the blade trigger being connected to the blade shaft, and the cutting blade connected to the blade shaft being movable proximally and distally lengthwise through the first and second jaws and within the cut channel of the first jaw and the second jaw;
  an electrosurgical unit arranged to supply radiofrequency (RF) energy to the electrosurgical instrument removably coupled to the electrosurgical unit, the electrosurgical unit being arranged to supply RF energy between the first electrode and the first jaw to seal tissue in contact with the first electrode and the first jaw and to supply RF energy between the first electrode and the second electrode to cut tissue in contact with the first electrode and the second electrode; wherein the generator is arranged to determine a phase value of the supplied RF energy between the first electrode and the first jaw and to determine when the determined phase value of the supplied RF energy equals or exceeds a predetermined phase value;
  wherein the generator, after determining the determined phase value of the supplied RF energy equals or has exceeded the predetermined phase value, is arranged to supply RF energy between the first jaw and the cutting blade; and
  wherein the generator is arranged to determine a phase value of the supplied RF energy between the first jaw and the cutting blade to determine when the determined phase value of the supplied RF energy equals or exceeds a second predetermined phase value; wherein the generator, after determining the determined phase value of the supplied RF energy equals or has exceeded the second predetermined phase value, is arranged to supply RF energy between the first electrode and the first jaw.

12. The system of claim 11 wherein the plurality of stops comprises a first stop projection movable with the blade shaft and when moved distally near a distal end of the cut channel of the first jaw, the first stop projection interacts with a corresponding stop projection or slot preventing further distal movement of the first stop projection and the blade shaft.

13. The system of claim 12 wherein the plurality of stops further comprises a second stop projection on the blade shaft and spaced from the first stop projection, the second stop projection preventing proximal movement of the blade shaft beyond a predetermined point.

14. The system of claim 13 wherein the instrument further comprises a spring connected to the blade shaft and biasing the blade shaft proximally and wherein the second stop projection is arranged to prevent the spring from pulling the cutting blade proximally beyond the predetermined point and the spring and the second stop projection being arranged to hold the cutting blade in place at the predetermined point, the predetermined point being near a proximal end of the cut channel of the first jaw.

15. The system of claim 14 wherein the instrument further comprises a cable having a proximal end and a distal end, the distal end of the cable being attached to and extending from the stationary handle, a plug having one end connected to the proximal end of the cable and another end attached to a connector; and wherein the generator further comprises a tool connector receptacle; and wherein the connector of the instrument is removably attached to the tool connector receptacle and the connector comprises memory circuitry configured to be utilized by the generator.

16. The system of claim 15 wherein the tool connector receptacle includes a switch recessed within the tool connector receptacle that is operatively activated by the connector being inserted into the tool connector receptacle.

17. The system of claim 16 wherein the first jaw further comprises a seal surface comprising a plurality of seal paths surrounding the cut channel of the first jaw and a plurality of non-filled-in cavities positioned near and spaced from the plurality of seal paths and wherein the instrument further comprises a third electrode connected to the first jaw and extendable from a first position within the first jaw to a second position outside the first jaw and past a distal most end of the first jaw; and wherein the generator is arranged to supply RF energy between the third electrode and the first jaw.

18. The system of claim 16 wherein the first and second jaws are arranged to be positioned in an open position, a closed position and an intermediate state between the open and closed position, the instrument further comprises a sensor adjacent to the movable trigger and arranged to detect a position of the movable trigger to identify the intermediate state, and the electrosurgical unit is arranged to supply RF energy between the first electrode and the second electrode to cut tissue with the first and second jaws being in the intermediate state.

* * * * *